United States Patent
Wilson et al.

(10) Patent No.: US 11,167,122 B2
(45) Date of Patent: Nov. 9, 2021

(54) FORCE TRANSDUCTING IMPLANT SYSTEM FOR THE MITIGATION OF ATRIOVENTRICULAR PRESSURE GRADIENT LOSS AND THE RESTORATION OF HEALTHY VENTRICULAR GEOMETRY

(71) Applicant: Harmony Development Group, Inc., Cornelius, NC (US)

(72) Inventors: John Wilson, Cornelius, NC (US); Christopher Seguin, Norton, MA (US)

(73) Assignee: Harmony Development Group, Inc., Cornelius, NC (US)

( * ) Notice: Subject to any disclaimer, the term of this patent is extended or adjusted under 35 U.S.C. 154(b) by 142 days.

(21) Appl. No.: 16/293,474

(22) Filed: Mar. 5, 2019

(65) Prior Publication Data

US 2019/0269839 A1    Sep. 5, 2019

Related U.S. Application Data

(60) Provisional application No. 62/638,833, filed on Mar. 5, 2018.

(51) Int. Cl.
*A61M 1/10* (2006.01)
*A61M 60/148* (2021.01)
*A61F 2/24* (2006.01)
*A61M 60/896* (2021.01)

(52) U.S. Cl.
CPC .......... *A61M 60/148* (2021.01); *A61F 2/246* (2013.01); *A61F 2/2418* (2013.01); *A61M 60/896* (2021.01); *A61F 2/2412* (2013.01); *A61F 2/2451* (2013.01); *A61F 2/2475* (2013.01);

(Continued)

(58) Field of Classification Search
CPC .......... A61M 1/10; A61M 1/12; A61M 1/122
See application file for complete search history.

(56) References Cited

U.S. PATENT DOCUMENTS

| 6,406,422 B1 | 6/2002 | Landesberg |
| 6,827,682 B2 | 12/2004 | Bugge et al. |
| 7,435,257 B2 | 10/2008 | Lashinski et al. |

(Continued)

FOREIGN PATENT DOCUMENTS

| CN | 1399531 A | 2/2003 |
| CN | 101484093 A | 7/2009 |

(Continued)

OTHER PUBLICATIONS

International Search Report and Written Opinion for International Application No. 2018/034174 dated Jul. 27, 2018.

(Continued)

*Primary Examiner* — Matthew W Schall
(74) *Attorney, Agent, or Firm* — Stephen J. Kenny; Robert Piston; Foley Hoag LLP

(57) ABSTRACT

An implant system for restoring and improving physiological intracardiac flow in a human heart is provided including a force transducting, structurally stabilizing, and functionally assisting ventricular inflatable cardiac implant within a human heart for restoring and improving physiologic intracardiac flow, restoring the ventricular vortex, preventing atrioventricular pressure gradient loss, mitigating valvular regurgitation, and utilizing native energy and force, via force transduction, to restore geometric elliptical proportion and function to the atria, the ventricles and ventricular walls, and the valvular apparatus itself.

20 Claims, 49 Drawing Sheets

(52) U.S. Cl.
CPC .............. *A61F 2230/0052* (2013.01); *A61F 2230/0093* (2013.01)

(56) References Cited

U.S. PATENT DOCUMENTS

| | | | |
|---|---|---|---|
| 7,854,762 | B2 | 12/2010 | Speziali et al. |
| 8,092,525 | B2 | 1/2012 | Eliasen et al. |
| 8,778,017 | B2 | 7/2014 | Eliasen et al. |
| 9,050,189 | B2 | 6/2015 | Padala et al. |
| 9,078,660 | B2 | 7/2015 | Boutillette et al. |
| 9,486,306 | B2 | 11/2016 | Tegels et al. |
| 9,498,330 | B2 | 11/2016 | Solem |
| 10,806,571 | B2 | 10/2020 | Wilson et al. |
| 10,806,581 | B2 | 10/2020 | Wilson et al. |
| 10,813,747 | B2 | 10/2020 | Wilson et al. |
| 10,813,761 | B2 | 10/2020 | Wilson et al. |
| 10,940,002 | B2 | 3/2021 | Wilson et al. |
| 2003/0032855 | A1 | 2/2003 | Shahinpoor |
| 2006/0058871 | A1 | 3/2006 | Zakay et al. |
| 2006/0241745 | A1 | 10/2006 | Solem |
| 2007/0093890 | A1 | 4/2007 | Eliasen et al. |
| 2007/0198082 | A1 | 8/2007 | Kapadia et al. |
| 2007/0265490 | A1 | 11/2007 | Smith et al. |
| 2007/0270943 | A1 | 11/2007 | Solem et al. |
| 2007/0282157 | A1 | 12/2007 | Rottenberg et al. |
| 2008/0064917 | A1 | 3/2008 | Bar et al. |
| 2008/0243245 | A1 | 10/2008 | Thambar et al. |
| 2008/0294251 | A1 | 11/2008 | Annest et al. |
| 2008/0306328 | A1 | 12/2008 | Ercolani et al. |
| 2009/0048668 | A1 | 2/2009 | Wilson et al. |
| 2009/0131849 | A1 | 5/2009 | Maurer et al. |
| 2009/0177028 | A1 | 7/2009 | White |
| 2009/0254195 | A1 | 10/2009 | Khairkhahan et al. |
| 2009/0287040 | A1 | 11/2009 | Khairkhahan et al. |
| 2011/0022164 | A1 | 1/2011 | Quinn et al. |
| 2011/0196483 | A1 | 8/2011 | Forsell |
| 2011/0224655 | A1 | 9/2011 | Asirvatham et al. |
| 2012/0143320 | A1 | 6/2012 | Eliasen et al. |
| 2013/0030519 | A1 | 1/2013 | Tran et al. |
| 2013/0172978 | A1 | 7/2013 | Vidlund et al. |
| 2013/0325110 | A1 | 12/2013 | Khalil et al. |
| 2013/0338763 | A1 | 12/2013 | Rowe et al. |
| 2014/0277404 | A1 | 9/2014 | Wilson et al. |
| 2014/0309732 | A1 | 10/2014 | Solem |
| 2014/0336751 | A1 | 11/2014 | Kramer |
| 2014/0371789 | A1 | 12/2014 | Hariton et al. |
| 2014/0371843 | A1 | 12/2014 | Wilson et al. |
| 2014/0371846 | A1 | 12/2014 | Wilson et al. |
| 2015/0073539 | A1 | 3/2015 | Geiger et al. |
| 2015/0112429 | A1 | 4/2015 | Khairkhahan et al. |
| 2015/0223934 | A1 | 8/2015 | Vidlund et al. |
| 2015/0245934 | A1 | 9/2015 | Lombardi et al. |
| 2016/0089234 | A1 | 3/2016 | Gifford, III |
| 2016/0089237 | A1 | 3/2016 | Wilson et al. |
| 2016/0113765 | A1 | 4/2016 | Ganesan et al. |
| 2016/0199181 | A1 | 7/2016 | Kramer |
| 2016/0242909 | A1 | 8/2016 | Ketai et al. |
| 2016/0317290 | A1 | 11/2016 | Chau et al. |
| 2017/0000935 | A1 | 1/2017 | Vasilyev et al. |
| 2017/0136162 | A1 | 5/2017 | van Dort et al. |
| 2017/0172737 | A1 | 6/2017 | Kuetting et al. |
| 2018/0015141 | A1 | 1/2018 | Jay et al. |
| 2018/0185145 | A1 | 7/2018 | Wilson et al. |
| 2018/0318071 | A1 | 11/2018 | Lozonschi et al. |
| 2018/0344461 | A1 | 12/2018 | Wilson et al. |

FOREIGN PATENT DOCUMENTS

| | | |
|---|---|---|
| CN | 104042300 A | 9/2014 |
| CN | 204169959 U | 2/2015 |
| CN | 205198210 U | 5/2016 |
| CN | 105726072 A | 7/2016 |
| CN | 106214289 A | 12/2016 |
| WO | WO-2012/130052 A1 | 10/2012 |
| WO | WO-2018/129312 A1 | 7/2018 |
| WO | WO-2018/129320 A1 | 7/2018 |
| WO | WO-2018/222894 A1 | 12/2018 |
| WO | WO-2019/006152 A1 | 1/2019 |
| WO | WO-2019/173385 A1 | 9/2019 |

OTHER PUBLICATIONS

International Search Report and Written Opinion for International Application No. PCT/US/2018035427 dated Jul. 27, 2018.
International Search Report and Written Opinion for International Application No. PCT/US2018/034177 dated Jul. 20, 2018.
International Search Report and Written Opinion for International Application No. PCT/US2018/040066 dated Sep. 12, 2018.
International Search Report and Written Opinion for PCT/US2018/012586, dated Mar. 20, 2018.
International Search Report and Written Opinion of the International Searching Authority from parent application PCT/US2018/12578 dated Mar. 28, 2018.
Extended European Search Report for EP Application No. 18736494.8 dated Aug. 28, 2020.
Extended European Search Report for EP Application No. 18736566.3 dated Aug. 20, 2020.
International Search Report and Written Opinion for International Application No. PCT/US19/20816 dated Jul. 9, 2019.

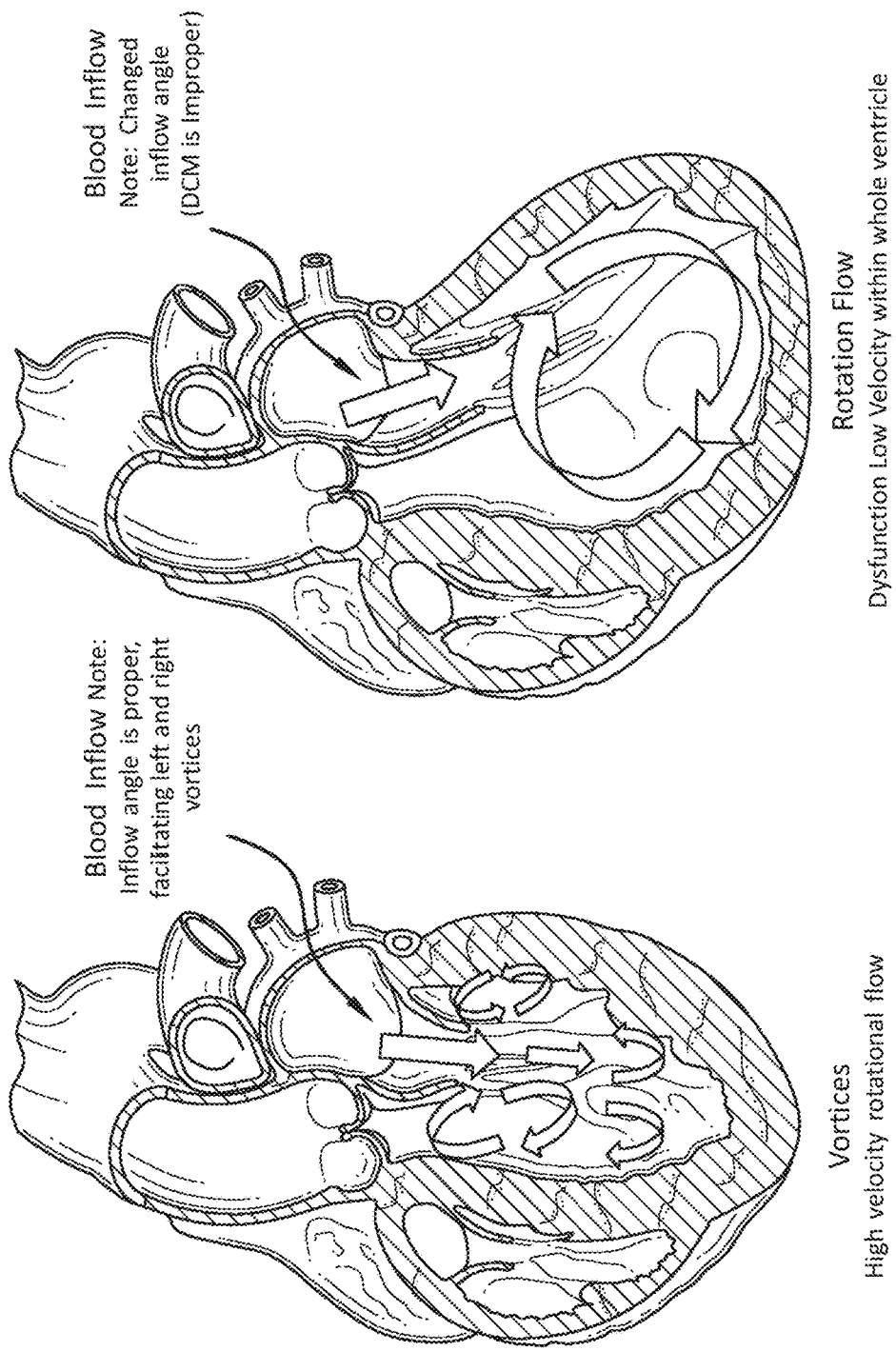

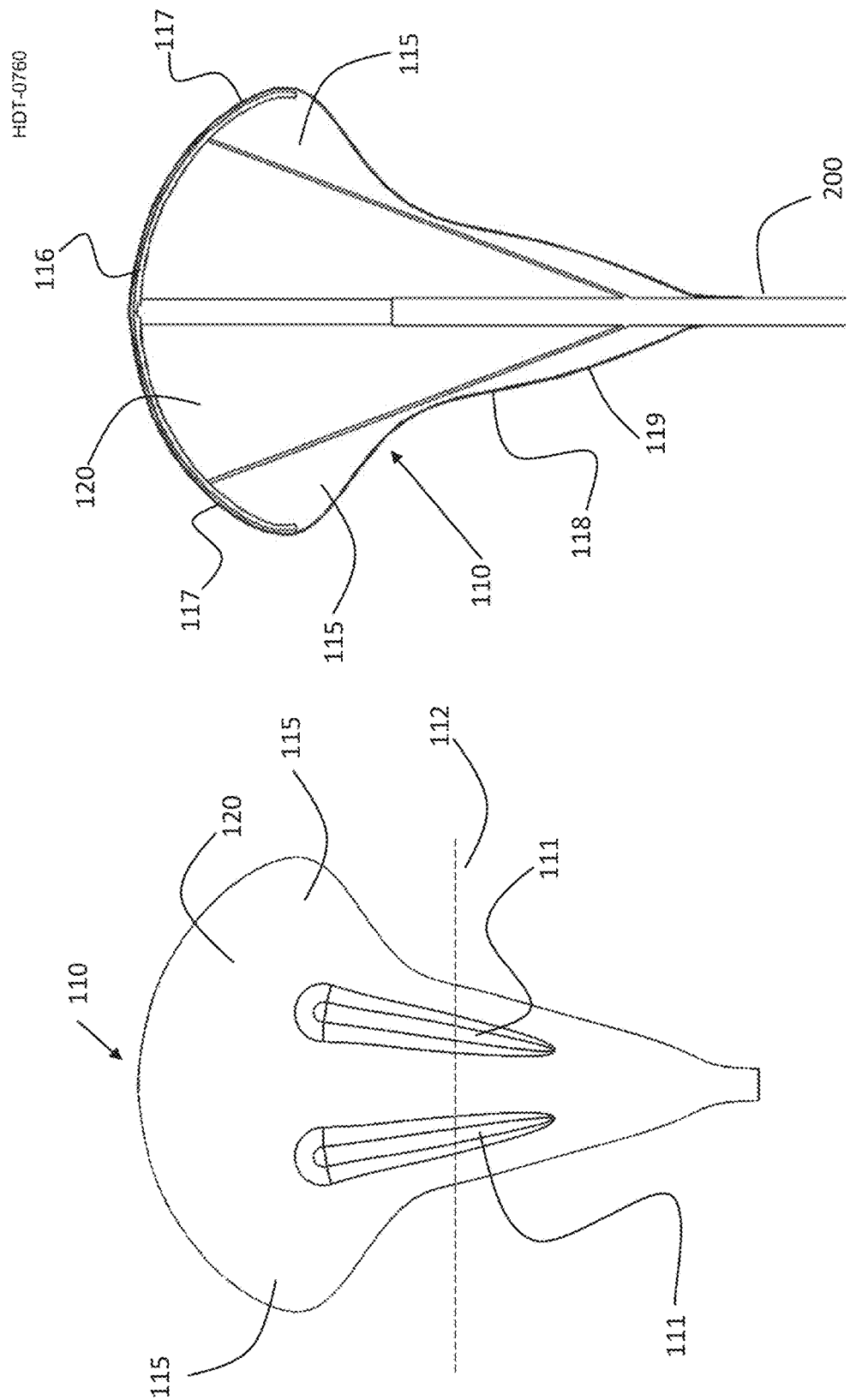

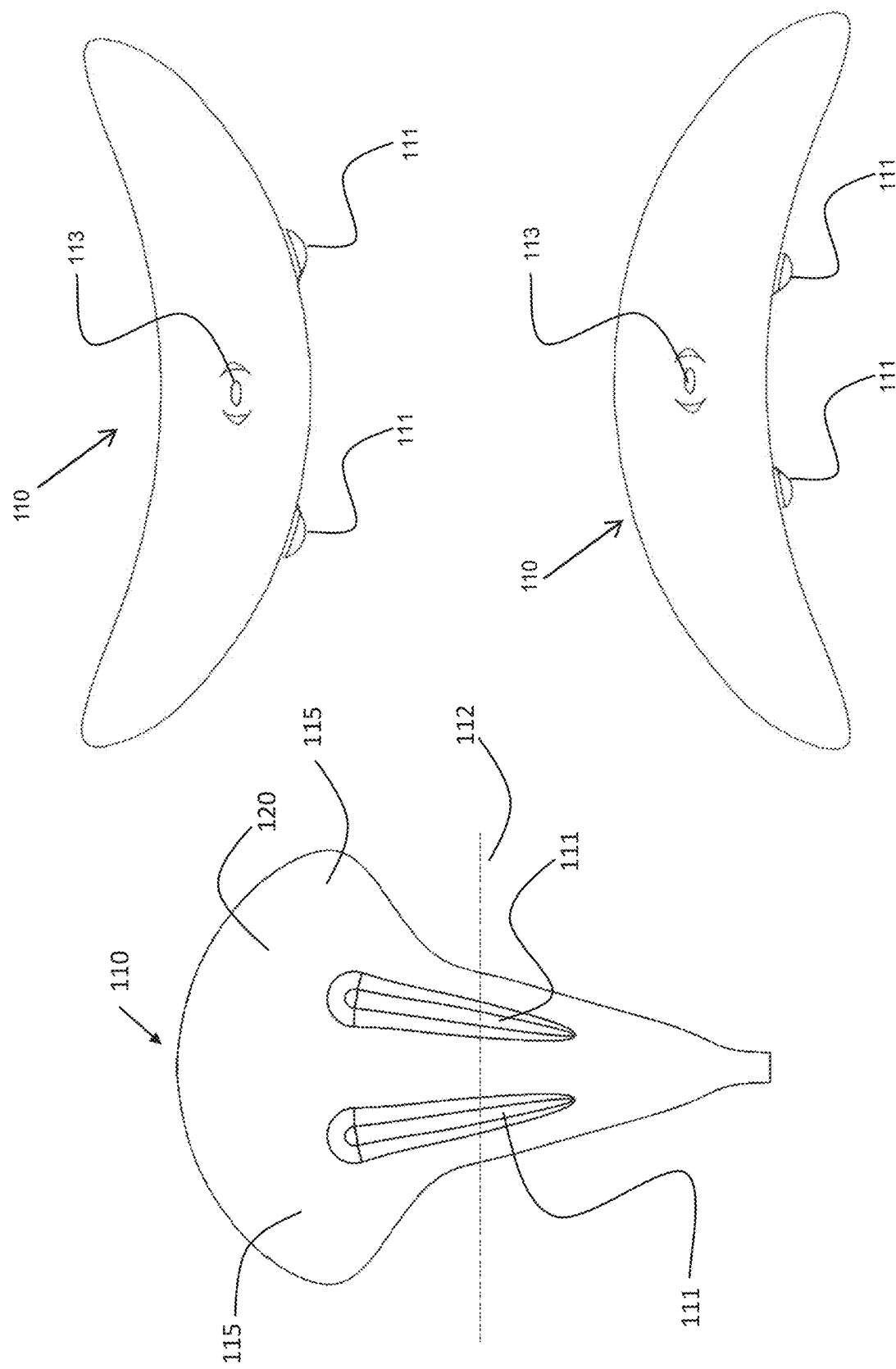

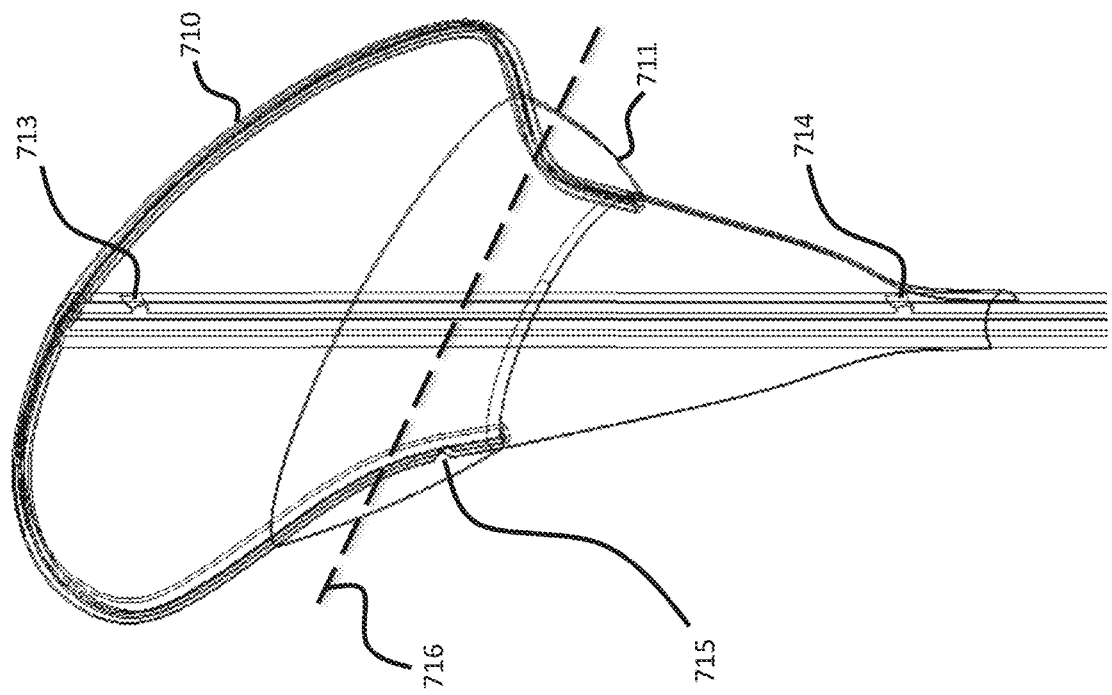
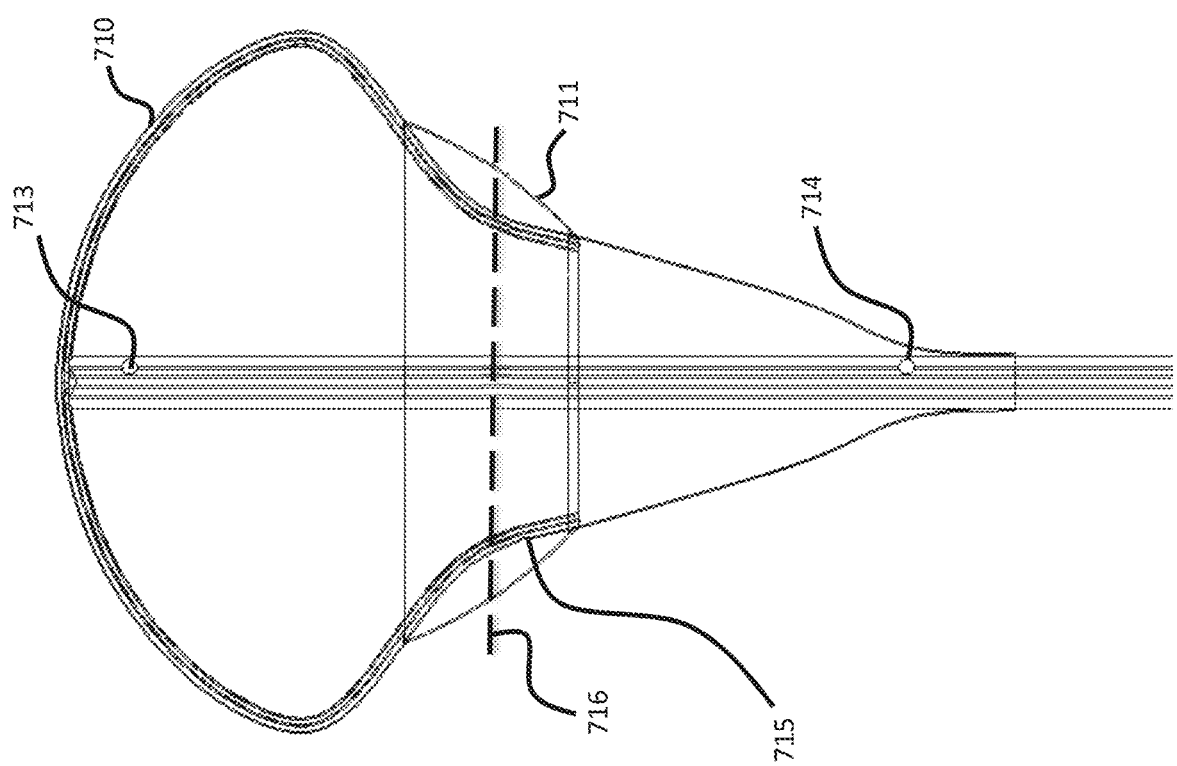
FIG. 22

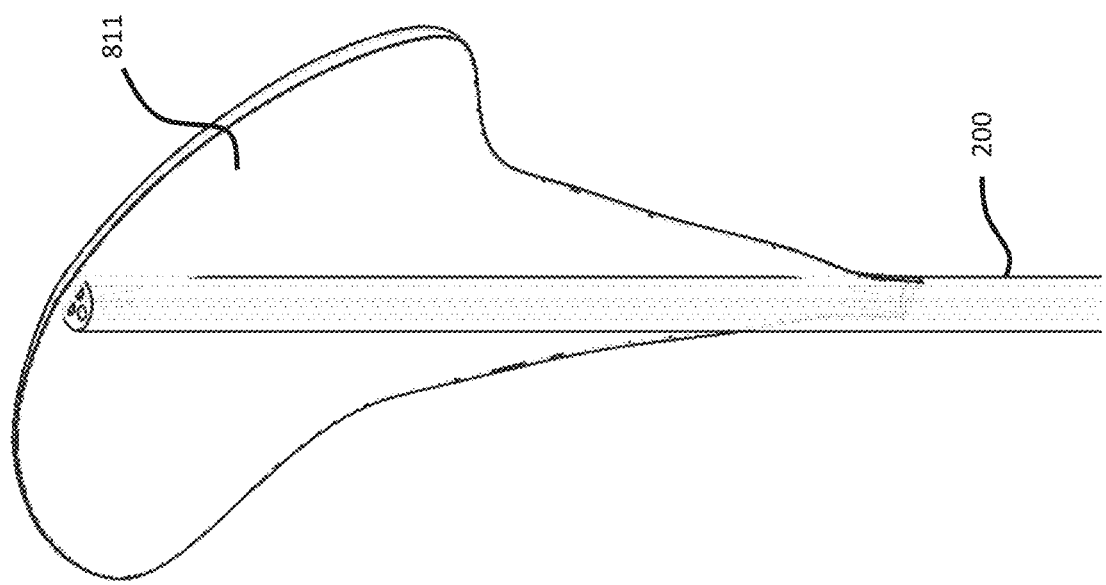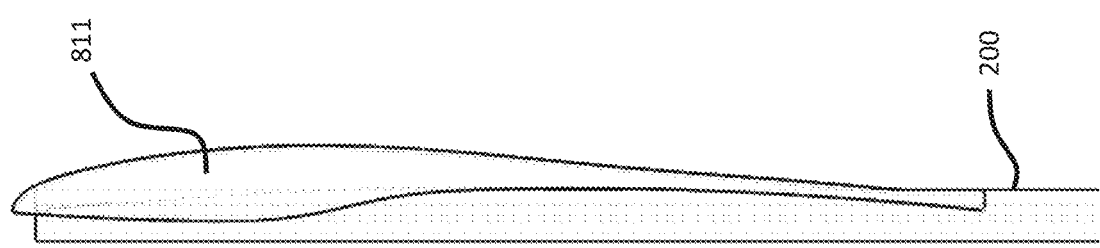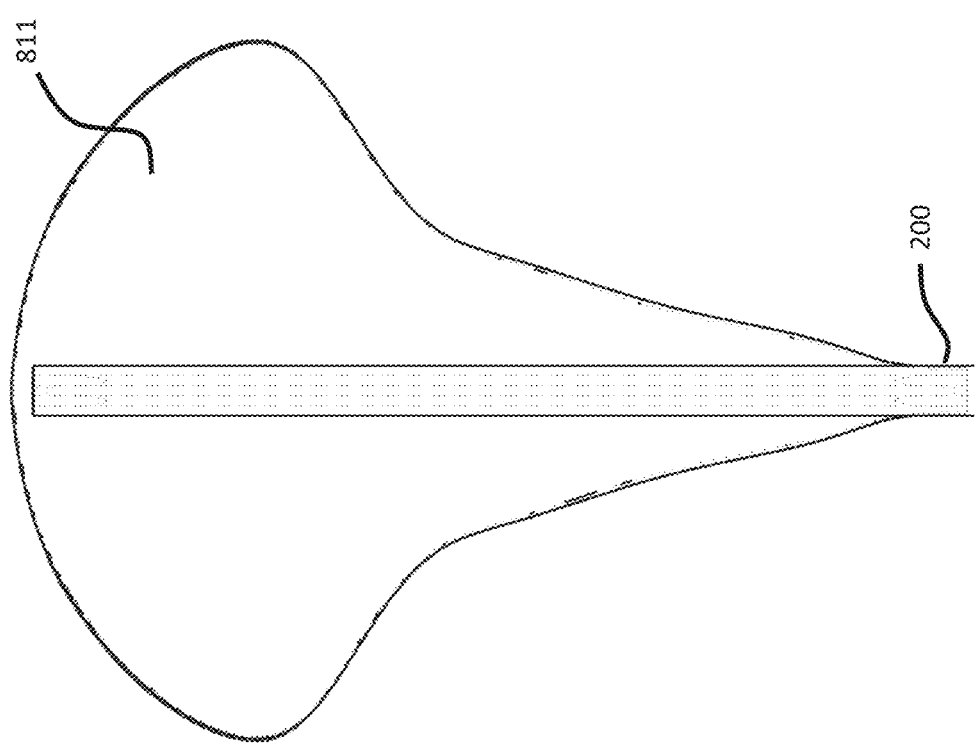
FIG. 27

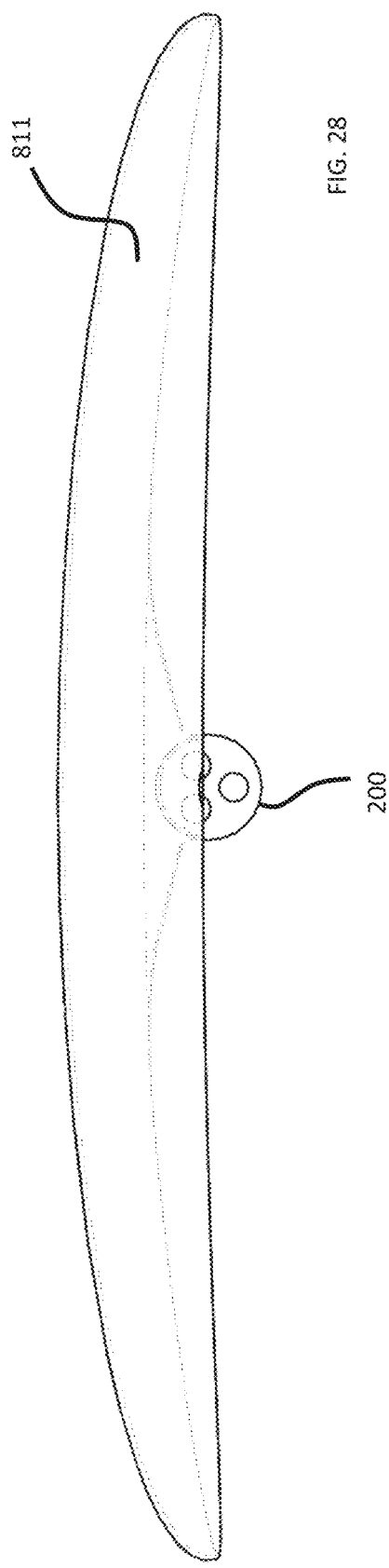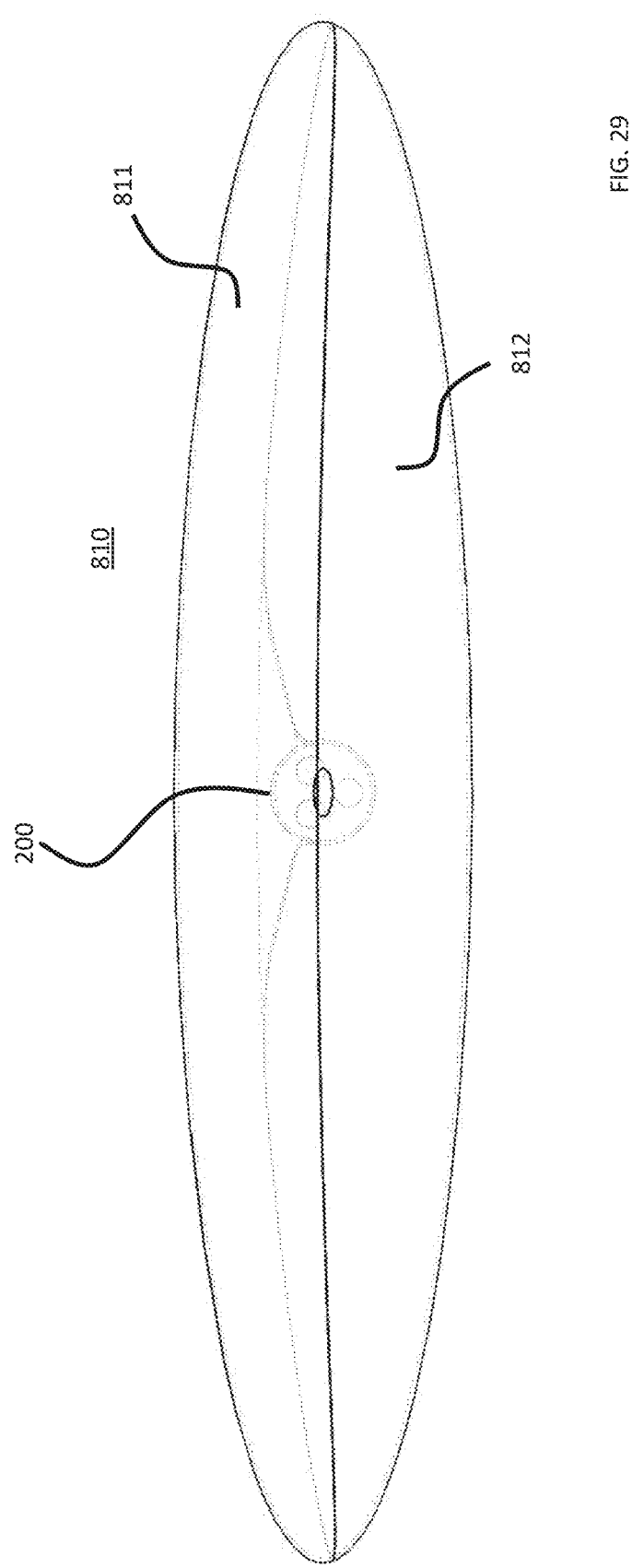

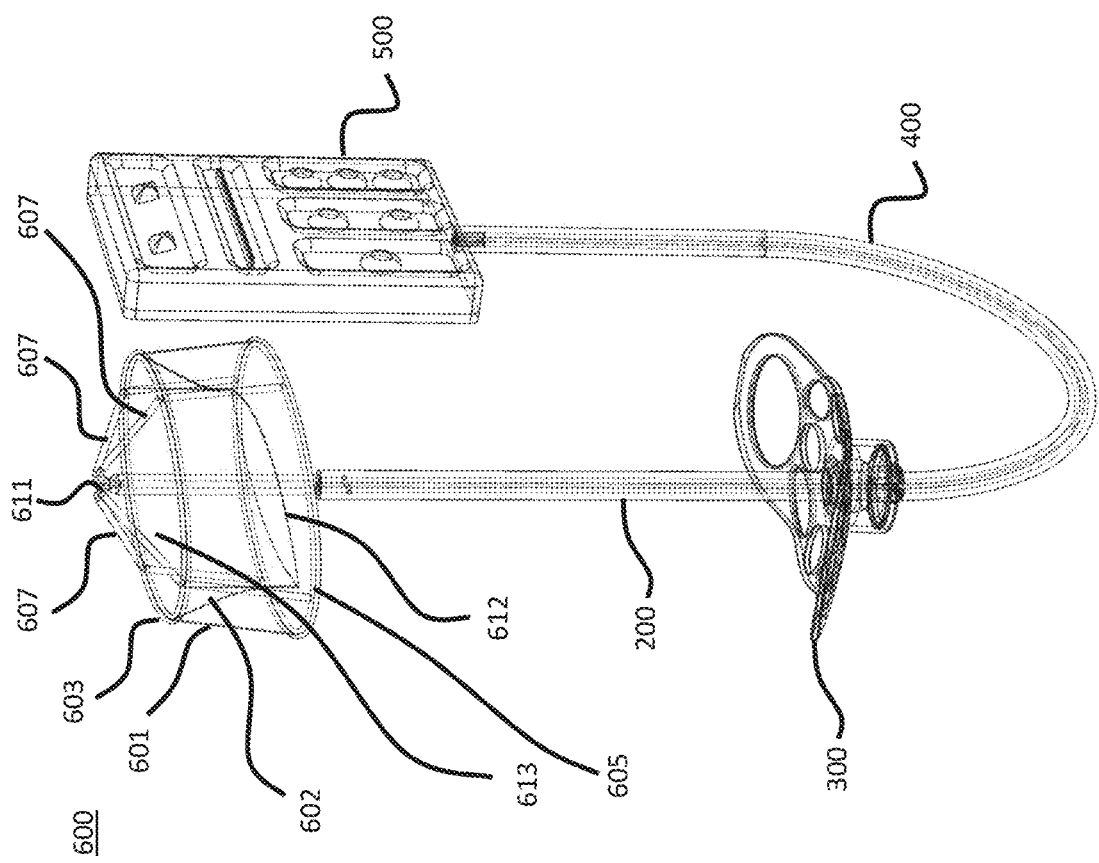

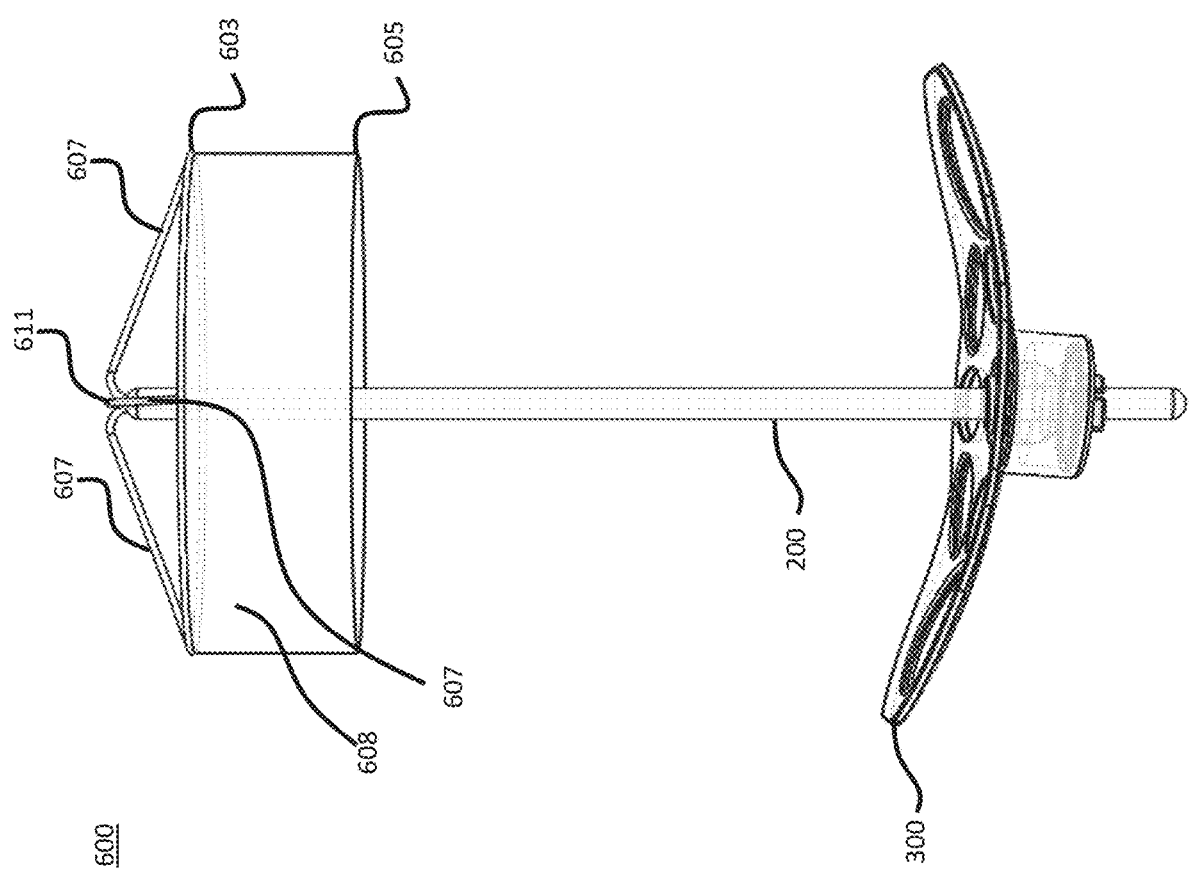

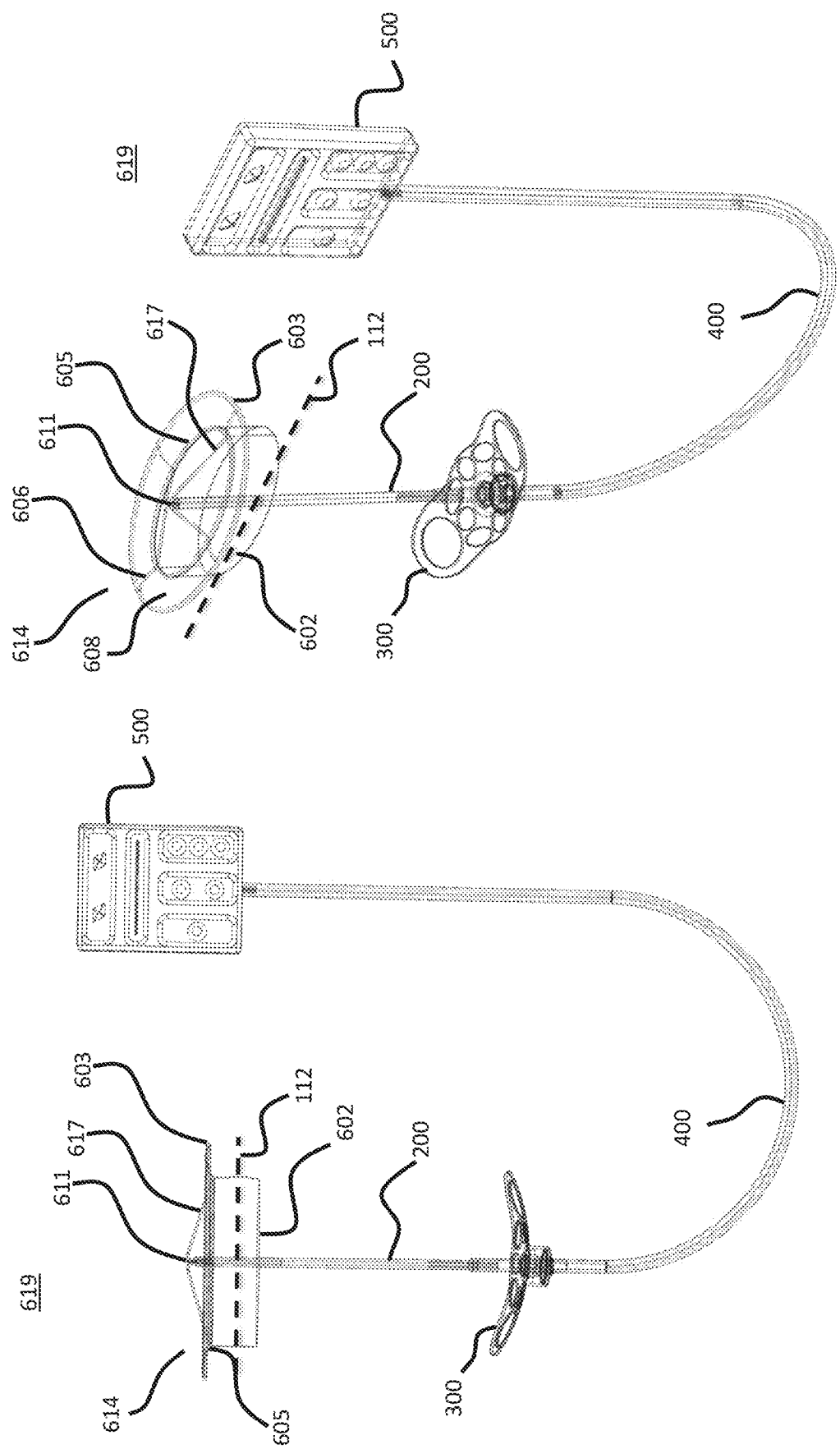

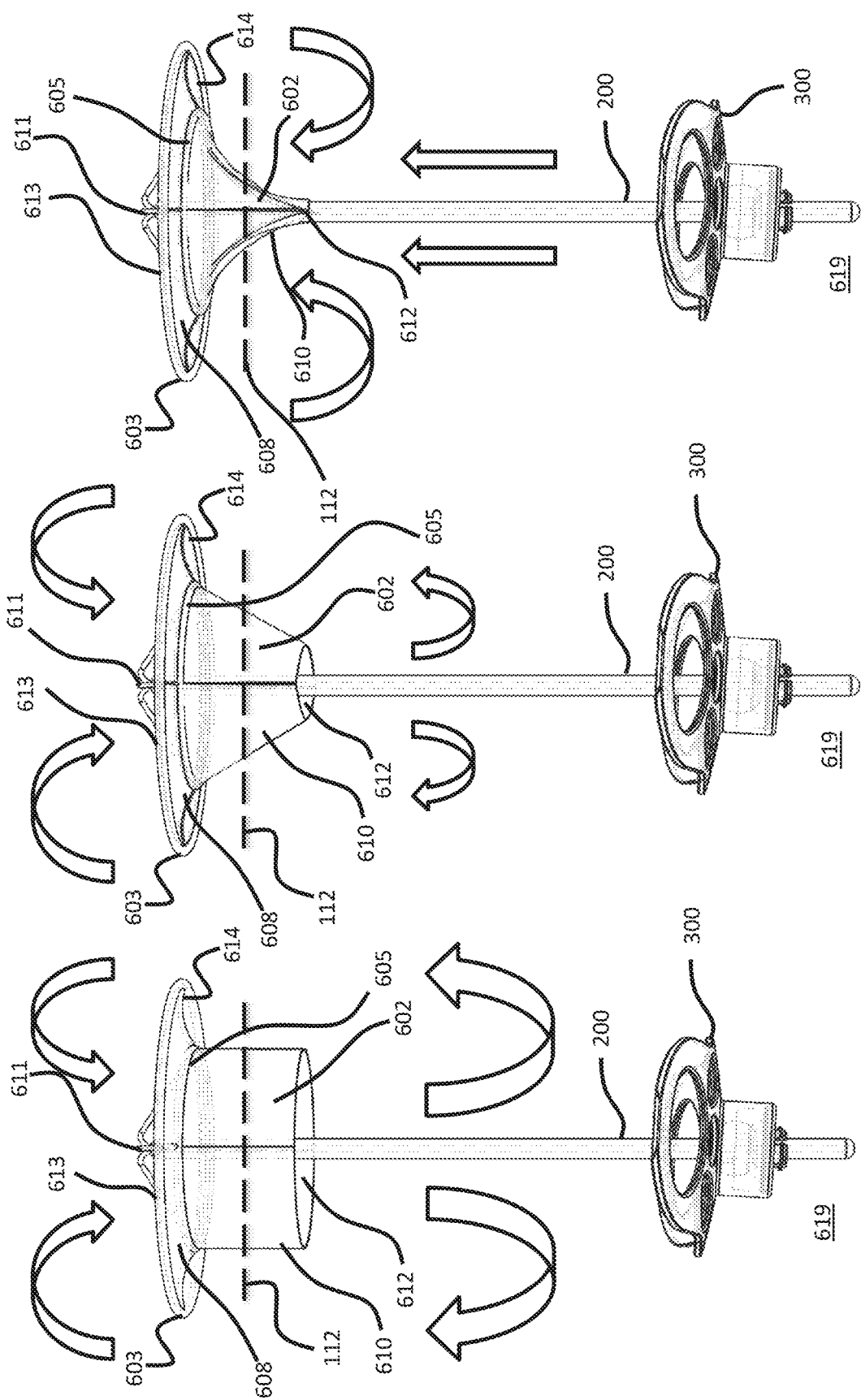

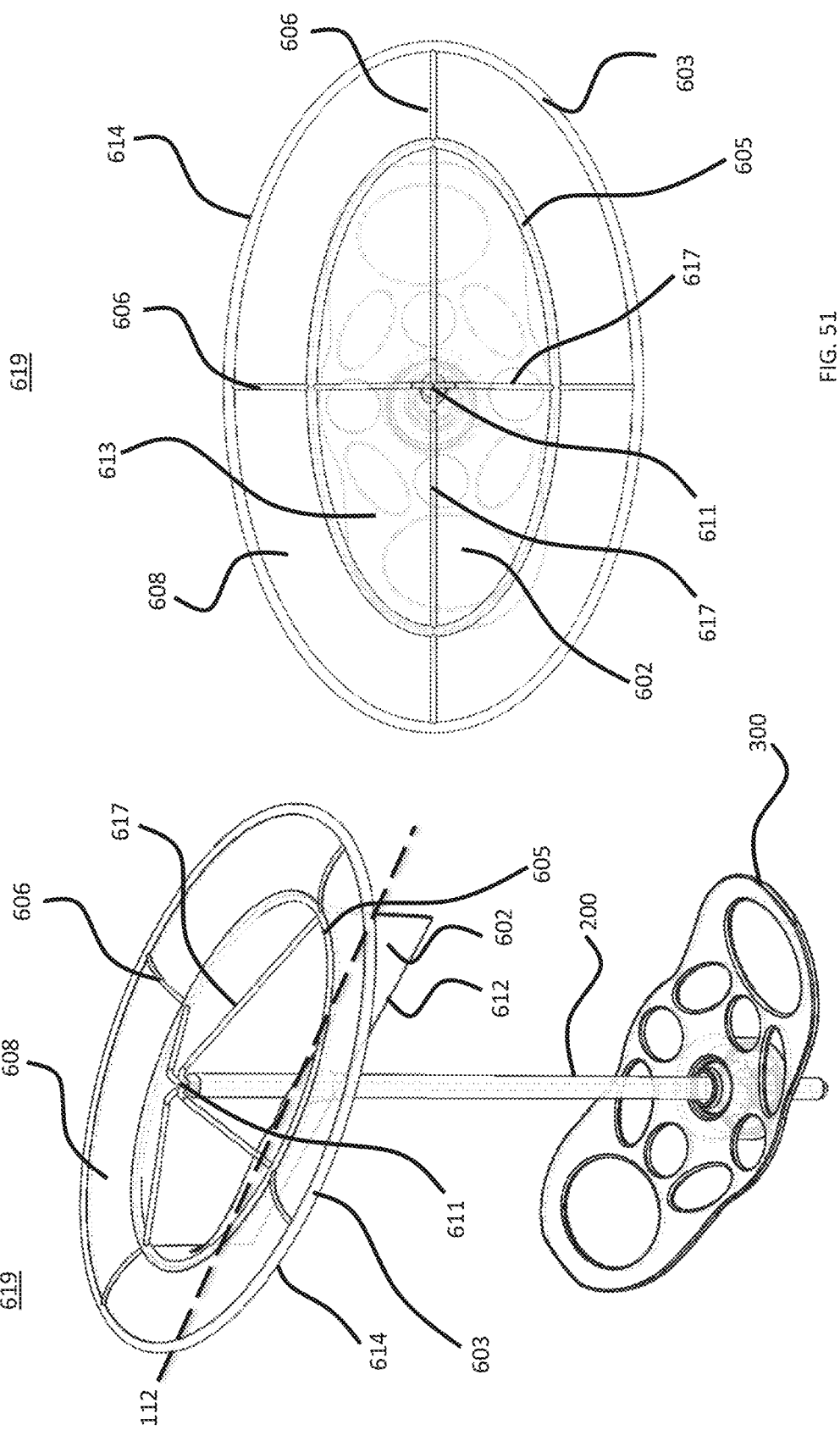

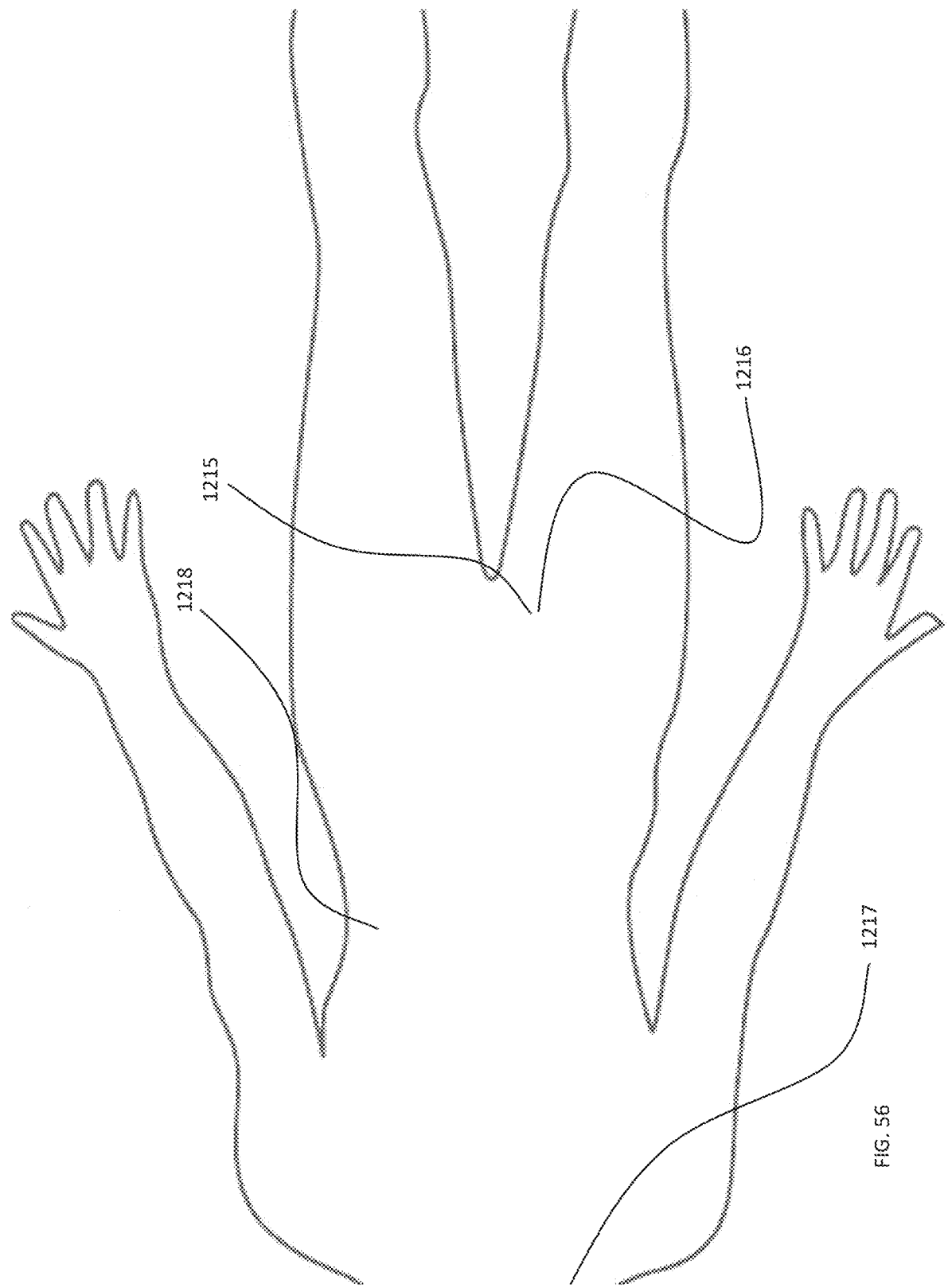

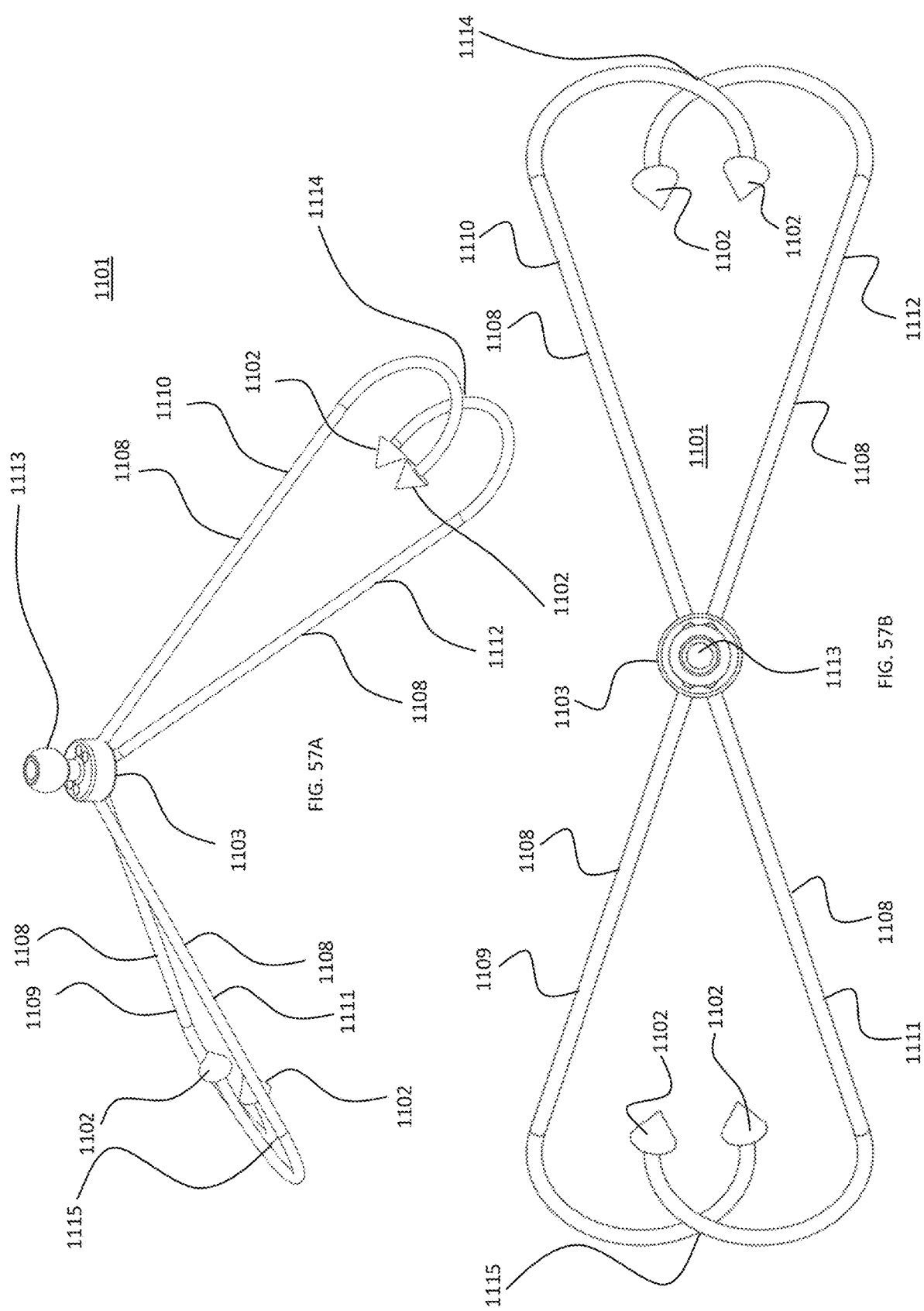

FORCE TRANSDUCTING IMPLANT SYSTEM FOR THE MITIGATION OF ATRIOVENTRICULAR PRESSURE GRADIENT LOSS AND THE RESTORATION OF HEALTHY VENTRICULAR GEOMETRY

CROSS-REFERENCE TO RELATED APPLICATION

This application claims the benefit of U.S. Provisional Patent Application No. 62/638,833, filed on Mar. 5, 2018, which is hereby incorporated by reference in its entirety.

BACKGROUND

The present disclosure generally relates to an integrated force transducting, structurally stabilizing, and functional ventricular assisting inflatable, semi-rigid, or rigid integrated implant system contained within a human heart for restoring and improving physiologic intracardiac flow, mitigating atrioventricular pressure gradient loss, and utilizing the native energy and force of the atrioventricular pressure gradient, via force transduction (meaning the capture, collection, and transfer of existing native energy & force), to restore geometric elliptical shape, healthy proportion, and proper function to the atria, the ventricles, the ventricular walls, and the valvular apparatus itself.

BRIEF SUMMARY

In various embodiments, an implant system for restoring and changing physiological intracardiac flow, mitigating atrioventricular pressure gradient loss and valvular regurgitation, and utilizing the native pressure gradient as a reconstructive therapeutic force in a human heart is provided. The implant system includes a dual-force pressure mitigating implant having a one-way valve or check valve mounted within a ring structure that allows atrial blood to pass through it into the ventricle but prevents ventricular blood from returning into the atrium. The dual-force pressure mitigating implant further includes a pressure mitigating assembly having a mechanical dual force structural housing having a proximal annular expanding ring structure, a distal suspension ring, and gradient funneling skirt, the proximal annular expanding ring structure supporting the valve skirt that seals to the distal suspension ring, the distal suspension ring supporting the one-way or check valve. The implant system further includes an anchoring system comprising one or more therapeutic base plate assemblies attachable to the heart's apex or wall or structures. The implant system further includes a universal tether assembly, comprising a tether or tethers or shaft, connected between the pressure mitigating assembly and the anchoring system, wherein the pressure mitigating assembly remaining tethered to the apex of the heart via the shaft and via the apical base plate. The implant system further includes a conduit providing a fluidic connection and a control unit with multiple sealed chambers to control the volume in the fluidic lumens and bladders and to house sensor components.

In various embodiments, an implant system includes a vortex flow directing member or balloon or any other distal assembly. The vortex flow directing implant or distal system assembly intercepts, mitigates, directs, re-directs, steers, and/or vectors hemodynamic flow in one cardiac phase while substantially simultaneously sealing the ventricle during the next cardiac phase and retains the atrioventricular pressure gradient and captures, harnesses, and delivers, via the tether or shaft to the base plate, native cardiac energy and force and native atrioventricular pressure gradient energy and force that is then delivered to the ventricular structures, septum, and/or the ventricular walls restoring the native valvulo-ventricular interaction.

In various embodiments, an intracardiac passive ventricular assist, support, and repair implant system is provided. The implant system includes a distal assembly, a shaft, and an apical base plate. The distal assembly is tethered to the apex of the heart via the shaft and the apical base plate. The implant system further includes a control unit and a connective multi-lumen tubing extending between the control unit and the implant. The implant system is configured to be a universal foundation of an integrated system and these combined components create the foundation for an integrated ventricular support and repair system.

In various embodiments, an anchoring plate configured to position, anchor, and connect an implant directly to the papillary muscles, precisely transfer targeted force and energy to the papillary muscles, and utilize the native pressure gradient as a reconstructive force in a human heart is provided. The anchoring plate includes a ball mount with a male universal ball connector, a connection member extending from the central ball mount, a first fixation wire extending from the connection member, and a second fixation wire extending from the connection member. The first fixation wire has a curved distal end and a first anchor at a distal-most end, and the second fixation wire has a curved distal end and a second anchor at a distal-most end. The curved distal end of the second fixation wire oriented in an opposite direction and overlapping the curved distal end of the first fixation wire. The anchoring system further includes a shaft receiver coupling the ball mount and a shaft connecting an atrioventricular distal attachment to the anchoring plate.

BRIEF DESCRIPTION OF THE DRAWINGS

The objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

FIG. 1 illustrates vortex formation and vortical hemodynamic flow patterns of a healthy human heart according to an embodiment of the present disclosure.

FIG. 2 illustrates the dysfunctional vortex formation and dysfunctional hemodynamic flow patterns of a human heart with a dilated cardiomyopathy pathology, according to an embodiment of the present disclosure.

FIG. 8 illustrates a member; a front view of an outer inflatable balloon; an enlarged member or balloon as a vortical blood flow vectoring/steering force and a mitigating force for atrioventricular pressure gradient loss (MR reduction) according to an embodiment of the present disclosure.

FIG. 9 illustrates a member a front cross-section view of an inner inflatable balloon; an enlarged inner member or balloon and its structure as a vortical blood flow vectoring/steering force and a mitigating force for atrioventricular pressure gradient loss (MR reduction) according to an embodiment of the present disclosure.

FIG. 10 illustrates a member front view for perspective, and the top down view of the member flexed in the anterior and the posterior according to an embodiment of the present disclosure.

FIG. 22 is an enlarged cross sectional front view and cross sectional perspective view of a Vortex Flow Directing Implant according to an embodiment of the present disclosure.

FIG. 27 illustrates front, side, and perspective cross sectional views of a semi-lunar rigid inflatable member with the inflatable posterior side removed according to an embodiment of the present disclosure.

FIG. 28 is a top down cross sectional view of a semi-lunar rigid inflatable member with the inflatable posterior side removed according to an embodiment of the present disclosure.

FIG. 29 is a top down cross sectional view of a semi-lunar rigid inflatable member with the inflatable posterior side according to an embodiment of the present disclosure.

FIG. 31 is a perspective view of a Dual Force Pressure Mitigating Implant according to an embodiment of the present disclosure.

FIG. 32A is a front view of a Dual Force Pressure Mitigating Implant system without a coapting-vectoring member according to an embodiment of the present disclosure.

FIG. 45 is a front view of a Dual Force Pressure Coapting Implant according to an embodiment of the present disclosure.

FIG. 46 is a perspective view of a Dual Force Pressure Coapting Implant according to an embodiment of the present disclosure.

FIGS. 47-49 illustrate side views of a Dual Force Pressure Coapting Implant according to an embodiment of the present disclosure.

FIG. 47 is a side view of a Dual Force Pressure Coapting Implant with a one-way valve in the open position according to an embodiment of the present disclosure.

FIG. 48 is a side view of a Dual Force Pressure Coapting Implant with a one-way valve in the partial open position according to an embodiment of the present disclosure.

FIG. 49 is a side view of a Dual Force Pressure Coapting Implant with a one-way valve in the closed position according to an embodiment of the present disclosure.

FIG. 50 is a perspective view of a one-way valve in the closed position according to an embodiment of the present disclosure.

FIG. 51 is a top view of a one-way valve in the closed position according to an embodiment of the present disclosure.

FIG. 56 illustrates a portion of the human body and exemplary locations for performing a minimally invasive surgical procedure according to an embodiment of the present disclosure.

FIGS. 57A and 57B illustrate a splayhook anchor plate according to an embodiment of the present disclosure.

DETAILED DESCRIPTION

Figure 3:
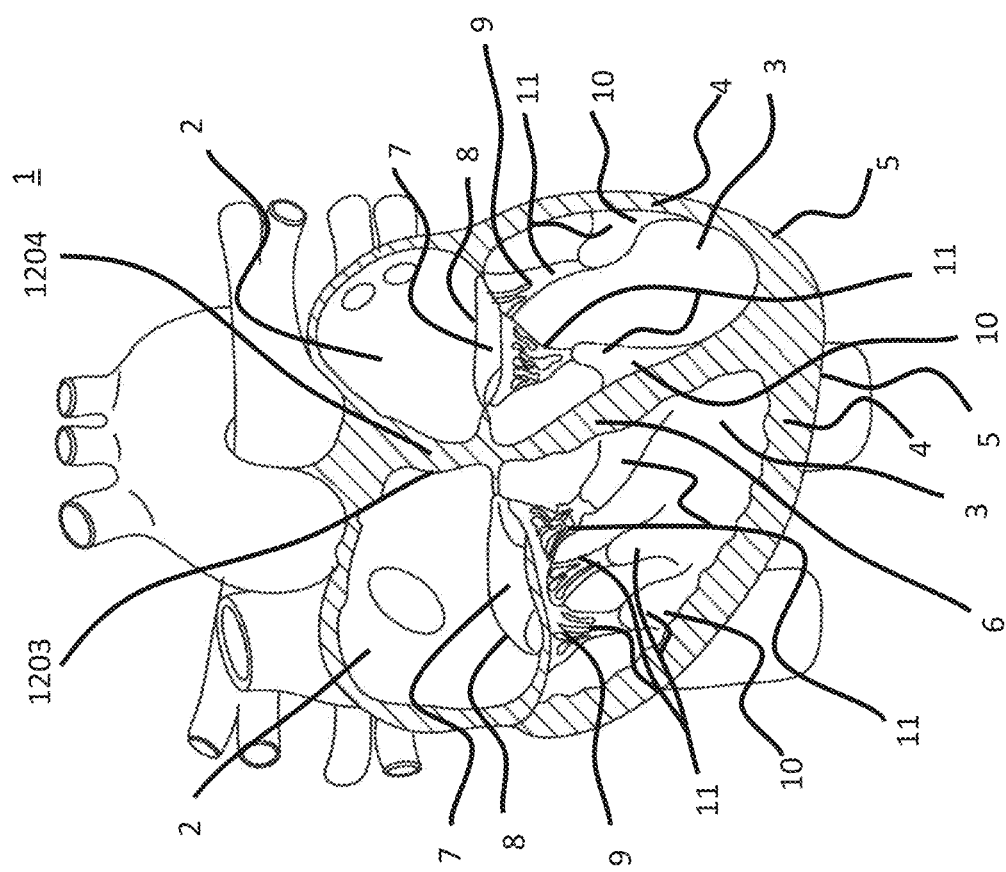
FIG. 3 illustrates the structures of a human heart according to an embodiment of the present disclosure.

An integrated implant system for restoring and improving physiological intracardiac flow, reducing or impairing atrioventricular pressure gradient loss or regurgitation, improving or restoring ventricular elliptical geometry and function, and providing ventricular functional and structural support within in a human heart is provided within an integrated vortex flow directing implant system comprising an inflatable bladder or member and/or another distal assembly or component; an anchoring system comprising a therapeutic apical base plate assembly attachable to the heart; a tether assembly comprising a tether or shaft connected between the implant inflatable member and the therapeutic apical base plate assembly; and a control unit attached via a multi-lumen tubing connection and implanted subcutaneously in another location.

Healthy and proper physiological intracardiac flow defined as healthy cardiac structures, healthy elliptical cardiac geometry, and healthy anterior and posterior ventricular vortex formation followed by healthy systolic ejection, combining both the kinetic energy of the vortex reservoir with ventricular myocardial muscular contraction, to feed the body with required oxygenated blood is critical to human life. The heart functions and moves blood in a cycle; this cycle consisting of a filling phase called 'diastole' and an ejection or pumping phase called 'systole'. In the filling phase, or 'diastole', the ventricle is filled with blood flowing from the atrium and through the atrioventricular valve. This filling phase occurs naturally and is powered, inside the human heart by a pressure gradient called the 'atrioventricular pressure gradient'. The atrioventricular pressure gradient is defined as a pressure difference (or a pressure differential) between the chambers of the heart. This pressure differential produces or generates an energy and a force between the chambers of the heart, this being naturally occurring, naturally initiated, and naturally applied. As the pressure increases in the atrium and pressure reduces in the ventricle, also called the 'diastolic' phase or diastole, blood flows from the higher-pressure atrium into the lower pressure ventricle, causing the valve leaflets to open thereby allowing blood to pass.

During the ejection or pumping phase, also called the 'systolic' phase or systole, the pressure in the atrium is exceeded by the pressure in the ventricle thereby generating a pressure differential which, in turn, pushes up, onto, and against the valve leaflets and causes or effects the valve leaflets to close and seal off the ventricular chamber from the atrial chamber. The atrioventricular pressure gradient, then, becomes the sealing energy and force required to close the valve. The blood is then ejected from and out of the ventricle, leaving the heart through the aortic valve, and out to the human body. The myocardium, or structural muscle that makes up the human heart, contracts toward the end of the diastolic cycle and the beginning of the systolic cycle. This contraction initiates the atrioventricular pressure gradient, mentioned above, that initiates this pressure, or energy and force, which 'closes the valve leaflets', which then seals the ventricular chamber closed. In the remaining systolic cycle, blood, under high pressure, is then ejected via muscular force aided by the healthy ventricular vortex (initiated in the diastolic cycle) to complete the hemodynamic cardiac output for that particular cycle. The intracardiac vortex initiates in the diastolic phase. In ventricular diastole, the ventricular pressure rapidly decreases. The atrioventricular valve opens and the blood rushes from the area of higher pressure, the atrium, into the area of lower pressure, the ventricle, through the atrioventricular valve orifice. The atrioventricular valve leaflets, on the ventricular side of the annulus, function to steer or vector the in-flowing blood, directing it at angle or vector to create an initial spin. Such angle or vector may be due to the asymmetry of the valve leaflets and/or to the different shapes and sizes of the leaflets. Regardless, a vortex progression results.

It is believed that the ventricular/apical counter twist, initiated in diastole, creates a bust of pressure which contacts the inflowing ventricular blood, leaving the leaflets at angle or vector, and thus begins the formation of ventricular vortex. The initial hemodynamic spin then, facilitated and assisted by the atrioventricular pressure gradient, engages the vectored blood such that a rotational vortex is created. The resulting high velocity rotational flow within the ventricle is believed significant to proper blood flow, cardiac output, and blood velocity enabling the blood to move throughout the human body's entire circulatory system. This resulting rotational flow or vortex, now a reservoir of kinetic energy within the ventricle, is believed significant to proper blood flow pattern, velocity and volume during systolic ejection. This cardiac cycle continues throughout the human lifecycle.

When healthy valve leaflets seal properly, the atrioventricular pressure gradient forces close the valve leaflets, seals the ventricle, and provides a strong ventricular structure to contain and utilize the atrioventricular pressure gradient for hemodynamic ejection and structural heart health. The papillary muscles, via the chordae tendineae, which are themselves attached to the valve's leaflets, pull and flex on the ventricle and ventricular walls thus maintaining healthy valvular structure, healthy ventricular shape, the healthy ventricular free wall, and healthy ventricular function (this is the heart's natural ventricular wall maintenance utilizing force transduction). This concert of interactive harmony facilitates healthy intracardiac vortical blood flow and insures proper valvular, structural, atrial, ventricular, and myocardial health. A cardiac insult or pathology can often initiate a failure that begins a cascade or rolling series of failures that each follows its predecessor. Ventricular shape change can cause the valve leaflets fail to seal, for example, and the energy and force from this atrioventricular pressure gradient is reduced or lost. This can greatly reduce the energy and force naturally transducted or delivered into the ventricular walls via the subvalvular apparatus (the chordae tendinea and the papillary muscles) contributing to ventricular wall insult, ventricular wall stress, and shape change that adds to this cascade of heart failure.

Cardiac insult, atrioventricular pressure gradient loss, and ventricular disease conditions can produce geometric shape change within the valves, the ventricles and the overall heart structure which can result in flow dysfunction. This change in ventricular geometric shape can cascade into changed flow dynamics, which in turn cause more intracardiac structural and flow dysfunction. In certain circumstances, this dysfunction can cause the ventricles to dilate or enlarge and the valve leaflets to no longer properly seal causing a reduction or loss of the atrioventricular pressure gradient, effectively being demonstrated by blood back-flow or regurgitant volume of fluid caused by the pressure gradient, visualized by blood volume, forcing its way between the failing valvular seal and seen in the atrium during the 'systolic' phase. The system disclosed within, is designed, inter alia, to capture, harness, collect, and re-direct the energy and force this atrioventricular pressure differential creates, whether it is contained by the valve leaflets or whether the energy and force is leaked or lost because of a failure of the ventricular structure, the ventricular geometry, or of the valve structure or valve leaflets to seal. Regardless of whether the valve leaflets seal or not, the energy and force of the atrioventricular pressure gradient is captured by device contact with the native structures, harnessed, and contained, and then re-directed from the member or bladder, via the tethering shaft, through the apical base plate and into the ventricular free wall, the extended apex, and the septal wall.

In some embodiments, the integrated system includes a Vortex Flow Directing Implant that employs the features and concepts of hemodynamic vector, atrioventricular pressure gradient loss mitigation, and force transduction (meaning the capture, collection, and transfer of existing native energy & force). During ventricular contraction, considerable forces are exerted on the closed mitral valve generated by the atrioventricular pressure gradient. These forces are transducted or transferred via the valve's leaflets, the chordae tendineae and papillary muscles into the ventricular wall. There is a resulting valvulo-ventricular wall interaction that provides the ventricle with structural support by maintaining the elliptical geometry, preventing papillary muscle displacement, and providing functional support required for proper ventricular health, healthy geometric proportion, and proper hemodynamic or blood ejection. During diastole, the ventricular pressure rapidly decreases. The atrio-ventricular valve opens and the higher-pressure atrial blood rushes from the atrium into the ventricle through the valve orifice. The atrio-ventricular valve leaflets function to steer or vector the blood, directing ventricular inflow at an angle or vector to create an initial spin. Such angle may be due to the asymmetry of the valve leaflets and/or to the different shapes and sizes of the leaflets and/or chordal tethering length. A ventricular vortex progression results. It is believed that the inflowing blood leaving the leaflets at angle or at vector is critical in the formation of ventricular vortex. The initial hemodynamic spin then begins, in which the inflowing blood is engaged by the atrioventricular pressure gradient, and that initial spin increases such that a vortex is created downstream. The resulting high velocity rotational flow within the ventricle is believed significant to proper blood flow through the heart and of significance in delivering enough blood to the body. The resulting rotational flow or vortex, now a reservoir of kinetic energy within the ventricle, is believed significant to proper blood flow patterns, velocities, and volumes through and out of the heart to the various reaches of the human body. By placing the member or bladder, attached to the distal end of the tether or shaft on the device, atrio/ventricularly, the Vortex Flow Directing Implant (the distal member or bladder being this engaging component of the system) engages and intercepts atrial blood, re-vectoring it through the valvular orifice, onto and off of the leaflets, at a vector which may be adjusted or changed, by increasing or decreasing the girth or fill of the member, to facilitate, assist, or deliver proper intracardiac vortical blood flow.

Force transduction is defined as the intentional capture, collection or harness, and movement or transfer of native energy and force from one area of the heart to another area of the heart. This energy and force may be of any natural source occurring within the human heart, be it muscular energy and force or atrioventricular pressure gradient generated energy and force. The movement of this energy and force can be mechanically re-purposed and delivered as a positive restoring therapy to components or areas of the heart that have been adversely effected by pathology or cardiac insult, it is believed. By placing the Vortex Flow Directing Implant atrioventricular manner and allowing the atrioventricular pressure gradient force to act on the exposed area of the implant, thus allowing the valve's leaflets to 'grab and pull' on the member, the member then captures, harnesses, and moves or transfers this atrioventricular energy and force, via the shaft, and delivers it to the ventricles, its structures, and the ventricular free walls via the ball jointed or fixed apical base plate. The atrioventricular pressure gradient energies and forces become a restoring, mechanically delivered, and re-purposed essential requirement for healthy ventricular function. By re-creating, repairing, and assisting the native impaired valvulo-ventricular interaction, that is the native 'pull, flexing and release' that occurs between the valve's leaflets, which are coupled to the chordae tendineae, which are then coupled to the papillary muscles, which are finally attached to the ventricular walls with a simple implanted mechanical device, an effective repair is created. That relationship in the impaired or diseased heart has been disrupted or lost between the impaired ventricle, the impaired valve, and the impaired ventricular free walls. This is a mechanical re-creation, by the device and the integrated system, of the action that the native ventricle and heart has lost due to the pathology, disease, or injury it has been subjected to and may be transformational in reducing the effects of heart failure. The 'grabbing, flexing and pulling', more precisely described as atrioventricular pressure gradient forces acting on the exposed area of the member or balloon via the valve leaflet's actions in diastole and systole, of the member by the valvular and subvalvular structures, mechanically replaces disturbed or lost native valvular and subvalvular forces (driven by the systolic atrio-ventricular pressure gradient) interaction with the ventricle and ventricular walls, by transducting or transferring this native force via the tether or shaft to the therapeutic apical base plate, to and in contact with the apex, the ventricle, and the ventricular walls. This creates both a structural and a functional supporting system for the weakened heart. In various embodiments, this re-instituted connection, created by restoring the connective relationship between the valve plane and the ventricle, results in a systolic ventricular structural and functional support increasing the ventricular ejection and cardiac output.

In some embodiments contained within the Vortex Flow Directing Implant and the integrated system that it is, the flow/force guiding member or bladder is the primary actuator, driver, and component in hemodynamic vector change or alteration, force transduction (meaning the capture, collection, and transfer of existing native energy & force), and in the mitigation of atrioventricular pressure gradient loss or regurgitation based on its presence within the atrio-ventricular valve structure. In its capacity related to force transduction (meaning the capture, collection, and transfer of existing native energy & force), the member or bladder is placed in the atrioventricular valve orifice (partially in the atrium, distally, and partially in the ventricle, proximally) and fixed to and maintained in this location by the shaft or tether. During the heart's cycle, the member or bladder is 'grabbed, flexed, and pulled' during systole thus allowing the atrioventricular pressure gradient force to act on and be captured by the exposed area of the member or bladder because of the contact made between the valve's leaflets and the member or bladder. It, the member or bladder, is then released in diastole because the valve's leaflets naturally open, as part of the cardiac cycle, to allow ventricular filling. This process occurs during every cycle that the heart completes. The opening and closing of the valve's leaflets is naturally powered by the atrioventricular pressure gradient, the pressure lowering in ventricular diastole and the pressure then increasing in ventricular systole. The member or bladder captures, harnesses, and transfers or moves this atrioventricular pressure gradient energy and force. captured on the exposed area by being 'grabbed, flexed, and pulled' in ventricular systole by the valve's leaflets, and then, via the tether/shaft and then via apical base plate, this native energy and force is passed onto and delivered into the ventricle and its structures, the septal wall, and the ventricular free walls thereby re-creating, mechanically, the impaired or lost natural valvulo-ventricular interaction. The valvulo-ventricular interaction, or the healthy natural relationship in which the valve's leaflets, attached to the chordae tendineae and the papillary muscles, is naturally used by the human heart to maintain the health, geometric elliptical shape, and compliance of the ventricle, the valve, and the ventricular free wall. This valvulo-ventricular relationship is then re-created mechanically with the Vortex Flow Directing Implant and the native energy and force found within the atrioventricular pressure gradient and is used and delivered as a ventricular restoring therapy to restore the impaired or lost ventricular structural maintenance the heart requires for healthy function. A failure of the valve leaflets to properly seal creates a leakage or loss of this atrioventricular pressure gradient. As the pressure gradient leaks, as evidenced by fluid or blood, back into the atrium from the ventricle, native energy and force is lost or diminished and this condition can lead to ventricular dysfunction and ventricular free wall dysfunction. In this case, the member or bladder, simply by its presence in the atrioventricular valve orifice, may act as a temporary seal or plug to reduce or cease this pressure gradient loss. The member or bladder itself just being present may accomplish this. Its presence in the atrioventricular orifice may reduce, slow, or impair the atrioventricular gradient loss that can occur. Additionally, in various embodiments, (a member within a member or balloon within a balloon), created by fitting of an 'inflatable belt' around the member or bladder such that the 'inflatable belt' runs around the member, as a protective belt, along the 'commissural line', meaning the line across which the valve's leaflets would naturally fall upon when they are closed or sealed during the systolic cycle. The native valve's leaflets seal along this 'line of commissure', as they naturally fall and arrest in this position, but the valve's leaflets may now, additionally, seal or seat themselves against this 'inflatable belt'. As the 'inflatable belt' is filled with fluid, gas, or another material, the topography of the leaflet edges may conformed to and seal against the inflatable belt, thereby reducing or stopping the atrioventricular pressure gradient leakage and therefore the loss of energy and force needed for healthy heart structure and function.

In various embodiments, the mitigating, sealing, and/or plugging of a leak of the atrioventricular pressure gradient in or around the valve leaflets may be accomplished with a semi-lunar shaped, malleable yet rigid, 'manta' or other shaped member or bladder, being solid on the posterior half and inflatable on the anterior portion. This may be reversed as well, meaning the posterior half is inflatable and the anterior portion is solid. The member or bladder being solid and in a semi-lunar shape on the anterior side, in this case, and inflatable on the posterior side allows the posterior leaflet edges to be topographically conformed with or to and then enables them to seal against this inflatable balloon on the posterior side.

In various embodiments, a Dual Force Pressure Mitigating Implant (an integrated system embodiment with the added 'one way valve' or 'check valve' and a pressure mitigating assembly or 'skirt' and utilizing the same shaft or tether, ball jointed apical baseplate or fixed baseplate, and control unit) has one or more contact points in the heart. The Dual Force Pressure Mitigating Implant is created by combining the 'one way valve' or 'check valve' and the pressure mitigating assembly or 'skirt' which then becomes the distal attachment to the shaft or tether, fixed to the apical ball jointed baseplate or fixed base plate, and control unit connected by the multi-lumen tubing. The Dual Force Pressure Mitigating Implant is positioned and fixated on the inflow or atrial side of the native or prosthetic valve and is rigidly fixed in location by the integrated system's shaft or tether which connects to the ball jointed apical baseplate or a fixed baseplate. The Dual Force Pressure Mitigating Implant is, in effect, a ventricular and valvular functional assist device that is placed above an atrioventricular native or prosthetic valve and assists the native or prosthetic valve in mitigating atrioventricular pressure gradient loss, preserving ventricular shape and function loss by connecting the valve plane to the apex of the heart thus applying force transduction (meaning the capture, collection, and transfer of existing native energy & force) into the ventricular structures, and ventricular walls, functioning as a ventricular assist device by loading the spring like structural housing (the framework of the pressure mitigating assembly) with energy & force in diastole (as the heart elongates and stretches that energy & force is captured and retained in the spring-like structures) and releasing the energy during systole without causing or creating any changes to the native anatomy within the human heart. The Dual Force Pressure Mitigating Implant can be a temporary or a permanent solution to the impaired valve, diseased ventricle, diseased ventricular structures, and impaired ventricular walls. In some embodiments, the distal suspension ring and proximal annular structural supports/rings or components are nitinol, elastic, expandable, and/or rigid so that the pressure mitigating assembly or 'skirt' may be expanded to mitigate, catch, and retain any atrioventricular pressure loss caused by the native or prosthetic valve's leaflets failing to maintain a seal. Any regurgitated blood is captured and retained inside the pressure mitigating assembly or 'skirt' and returned to the ventricle as the diastolic or ventricular filling phase occurs.

Connected or fixed to the distal suspension ring and the proximal annular ring and housed within the pressure mitigating assembly or 'skirt', is the 'one way valve' or 'check valve' that allows blood to flow in one direction through it from the atrium, through said 'one way valve' or 'check valve', and into the ventricle. The 'one way valve' or 'check valve' prevents the atrioventricular pressure gradient, demonstrated by the regurgitant blood flow, from leaking or regurgitating back from the ventricle and returning into the atrium. The 'one way valve' or 'check valve' is rounded and may or may not conform to the valve's annulus and/or the valves annular anatomy. The pressure mitigating assembly or 'skirt' is framed and structured by the expansion of the nitinol, elastic, expandable, and/or rigid material and the gradient funneling 'skirt' is constructed of a polymer and/or non-thrombotic material. The distal portion of the Dual Force Pressure Mitigating Implant structure consists of two components; the 'one way valve' or the 'check valve', which mitigates the atrioventricular pressure loss or regurgitation, and the pressure mitigating assembly, which is the housing, the mount, the structural and locational stability, and the anchor point for the 'one way valve' or 'check valve' fixed inside of it. The pressure mitigating assembly frame structure also supports the gradient funneling skirt by positioning it, providing its form, and holding it in place securely. In its dual force capacity, the nitinol, and/or elastic, expandable, spring like struts load the preload force generated by the elongation and filling of the ventricle in diastole and release it as spring loaded energy & force in and during systole. In this capacity, the Dual Force Pressure Mitigating Implant provides ventricular functional and ejectional support in addition to amplified force transduction (meaning the capture, collection, and transfer of existing native energy & force) of atrioventricular pressure gradient into the ventricle, ventricular structures, and ventricular walls. This function is not impacted negatively by the completed assembly of the Dual Force Pressure Mitigating Implant because the frame is spring-like and conformal. It contains, houses, and positions a 'one way valve' or 'check valve' with a 'duck bill', the open end or distal end oriented toward the atrium and the closed or billed end oriented proximally toward the ventricle. This orientation allows pressurized blood to pass through the 'one way valve' or 'check valve' from the atrial/distal side and move through the ventricular/proximal 'bill' and into the ventricle. Pressurized blood attempting to return from the ventricle back into the atrium is stopped and/or prevented by the closed 'one way valve' or 'check valve' proximal end 'duck bill' and this regurgitant blood volume is contained within the skirt on the atrial side of the native or prosthetic valve or within the ventricle. It should be noted that this Dual Force Pressure Mitigating Implant may be used as a preventative measure and not just as a reparative measure to treat the ventricle and its structure and not just a failing or compromised native or prosthetic valve. The Dual Force Pressure Mitigating Implant continues to act as a systolic ventricular assist and force transducting (meaning the capture, collection, and transfer of existing native energy & force) device by itself, remaining tethered to the apex via the shaft and via the apical base plate, and can be distally self-expanding and/or self-forming. In diastole, the atrioventricular pressure gradient functions normally, allowing pressure to freely pass into the ventricle through the 'one way valve' or 'check valve'. In systole, the 'duck bill', by facing proximally or oriented toward the ventricle, is sealed and closed by the atrioventricular pressure gradient and the energy & force is contained within the ventricle by the sealing 'duck bill' secured on the atrial side of the valve annulus which thus prevents any backflow or loss of the pressure gradient. This cycle continuously repeats itself. Due to the positioning and fixation of the device, The Dual Force Pressure Mitigating Implant does not interfere with the valve leaflets, the valvular substructure, or any of the valves components allowing for complete freedom of movement of all of these structures.

In some embodiments, the Dual Force Pressure Mitigating Implant can be attached to the tether or shaft with or without a coapting member or bladder placed on the tether or shaft along the line of coaptation. In some embodiments, the annular structural components may control the shape of the atrium around the valve annulus. In some embodiments, the annular structural components may control the shape of the native annulus of the heart. In some embodiments, the Dual Force Pressure Mitigating Implant is fixed on the inflow side of a valve, by a tether or shaft, in the atrium. In some embodiments, the structural components on the inflow side are in contact with the annular structure. In some embodiments, the Dual Force Pressure Mitigating Implant's structural components stabilize the device, center the device, the dual force components transduct (meaning the capture, collection, and transfer of existing native energy & force) an increased force to the apex, structures of the heart, ventricles, and the ventricular walls, and aid in the geometric reshaping of the ventricle, the reverse remodeling of the ventricles, strengthening the ventricular walls, and assisting in ventricular ejection and add a constant amount of cinching force and supporting structure by tethering or anchoring the annulus to the apex of the heart. In some embodiments, the annular structural components are fixed in location, in contact with, and attached to the annular structure of the valve, and/or shape and/or re-shape the valve annulus and/or the atrium. In some embodiments, the laterally extending struts are elastic and/or spring-based to absorb, store, recoil, and transfer energy into the endocardium, myocardium, and epicardium via the shaft and an attached base plate. In some embodiments, the laterally extending struts are elastic, nitinol, spring-like, and/or another expandable material designed to absorb, preload, return, and "launch" native cardiac energy and force. This force and energy is 'loaded' in the diastolic phase, held within this spring-like material, and released or 'launched' in this systolic phase. This facilitates and enables compounded energy and targeted force to be generated thereby further enhancing, facilitating, and creating the conditions for rapid ventricular positive or reverse remodeling.

In various embodiments, a Dual Force Annular Implant (an integrated system embodiment) is described and defines a dual force annular halo band, "D"-shape and/or saddle shape and/or circular and/or oval shape, of nitinol or a spring-like material purposed to connect the valve plane with the apex, fixed to a connecting shaft running though the ventricle and secured to the apex of the human heart, to impart or transduct (meaning the capture, collection, and transfer of existing native energy & force) the forces of the atrioventricular pressure gradient into the ventricle, the ventricular structures, and the ventricular walls. Connected to the self-expanding structure and/or the annular ring called the dual force annular halo, the Dual Force Annular Implant device, is simply a force transducting device that loads energy & force in diastole and releases this preloaded energy & force in systole. The Dual Force Annular Implant, acting as a force transducting (meaning the capture, collection, and transfer of existing native energy & force) therapy by itself, assembles the dual force annular halo, which is self-expanding, nitinol or spring-like, and/or self-forming and compounding ventricular systolic assist functioning by loading force in diastole and releasing this loaded force in systole, fixed to a shaft or tether, which is then fixed to the ball jointed or fixed baseplate. The dual force annular halo structure can be used as an annular reshaping device a transducting structure, and as a structural foundation and mount for valve plane to apex connection purposed to transfer native energy and force from one point directly to another. In some embodiments, both acting as a force transducting (meaning the capture, collection, and transfer of existing native energy & force) agent and a force compounding agent, within the atrium and the ventricle, connective function of tying the valve plane to the apex of the heart serves to act as an additional or prosthetic papillary muscle transducting and/or moving atrio-valvulo energy & force to the ventricle, the ventricular structures, and the ventricular walls.

In various embodiments, a Dual Force Pressure Coapting Implant (an integrated system embodiment with the added 'one way valve' or 'check valve' and a therapeutic fixation assembly and utilizing the same shaft or tether, ball jointed apical baseplate or fixed baseplate, and control unit) is described and has one or more contact points in the heart. The Dual Force Pressure Coapting Implant is created by combining the 'one way valve' or 'check valve' and the therapeutic fixation assembly which then becomes the distal attachment to the shaft or tether, fixed to the apical ball jointed baseplate or fixed base plate, and control unit connected by the multi-lumen tubing. The Dual Force Pressure Coapting Implant is positioned and fixated on the inflow or atrial side of the native valve and is rigidly fixed in location by the integrated system's shaft or tether which connects to the ball jointed apical baseplate or a fixed baseplate. The Dual Force Coapting Implant is, in effect, a ventricular and valvular functional assist device in which the therapeutic fixation assembly which is placed above an atrioventricular native valve and the 'one way valve' or 'check valve' proximal portion, which the therapeutic fixation assembly houses and structurally supports, is fixated in the valve orifice, between the anterior and posterior valve leaflets along the line of coaptation, and assists the native valve in mitigating atrioventricular pressure gradient loss, preserving ventricular shape and function loss by connecting the valve plane to the apex of the heart thus applying force transduction (meaning the capture, collection, and transfer of existing native energy & force) into the ventricular structures, and ventricular walls, functioning as a ventricular assist device by loading the spring like structural housing (the framework of the pressure mitigating assembly) with energy & force in diastole (as the heart elongates and stretches that energy & force is captured and retained in the spring-like structures) and releasing the energy during systole without causing or creating any changes to the native anatomy within the human heart. The Dual Force Coapting Implant can be a temporary or a permanent solution to the impaired valve, diseased ventricle, diseased ventricular structures, and impaired ventricular walls. The therapeutic fixation assembly may be expanded to mitigate, catch, and retain any atrioventricular pressure loss caused by the native valve's leaflets failing to maintain a seal or any loss that may get around the 'one way valve' or 'check valve' in the commissures of the native valve. Any regurgitated blood is captured and retained inside the therapeutic fixation assembly and returned to the ventricle as the diastolic or ventricular filling phase occurs. The therapeutic fixation assembly contains, houses, and positions a 'one way valve' or 'check valve' with a 'duck bill', the open end or distal end oriented toward the atrium and the closed or billed end oriented and fixated within the valve, between the valve's leaflets, proximally toward the ventricle. This orientation allows pressurized blood to pass through the 'one way valve' or 'check valve' from the atrial/distal side and move through the ventricular/proximal 'bill' and into the ventricle. Pressurized blood attempting to return from the ventricle back into the atrium is stopped and/or prevented by the closed 'one way valve' or 'check valve' proximal end 'duck bill' and this regurgitant blood volume is contained within the skirt on the atrial side of the native valve or within the ventricle. It should be noted that this Dual Force Pressure Coapting Implant may be used as a preventative measure and not just as a reparative measure to treat the ventricle and its structure and not just a failing or compromised native valve. The Dual Force Pressure Coapting Implant continues to act as a systolic ventricular assist and force transducting (meaning the capture, collection, and transfer of existing native energy & force) device by itself, remaining tethered to the apex via the shaft and via the apical base plate, and can be distally self-expanding and/or self-forming. In diastole, the atrioventricular pressure gradient functions normally, allowing blood to freely pass into the ventricle through the 'one way valve' or 'check valve'. In systole, the 'duck bill', by facing proximally or oriented toward the ventricle, is sealed closed by the atrioventricular pressure gradient and the energy & force is contained within the ventricle by the sealing 'duck bill' secured on the atrial side of the valve annulus which thus prevents any backflow or loss of the pressure gradient. This cycle continuously repeats itself. Due to the positioning and fixation of the device, The Dual Force Pressure Coapting Implant does not interfere with the valve leaflets, the valvular substructure, or any of the valves components allowing for complete freedom of movement of all of these structures.

The described embodiments, as an integrated system, are all implanted in a minimally invasive transapical manner. The transapical procedure commonly consists of gaining access to the apex of the heart through a thoracotomy. This is a standard, common, routinely used surgical access procedure utilizing standard transapical access technique, that being defined as an apical retrograde approach, accessing the ventricle and the atrioventricular valve with commonly used standard surgical, and medical techniques. Once the apex is visualized, a means of controlling the access site either via purse string suture and pledget or through an apical closure device that allows working access through the device while controlling the apex or access site is utilized. A needle is then used to insert a guidewire into the ventricle of the heart. The guidewire is held in place and the needle is then exchanged down the wire. A valved introducer sheath and dilator are introduced over the wire and used to dilate and created a sealed access site at the apex of the heart. Using either echocardiography or fluoroscopy or a combination for visualization, the sheath, dilator and guidewire are steered or maneuvered around the papillary muscles and chordae, across the atrioventricular valve, retrograde, or against the flow of blood, and into the atrium. The imaging is used to avoid entanglement with the subvalvular structures and to use as guidance as to where the implantation components are in the heart. Once in the atrium the guidewire and dilator can be removed from the sheath. The sheath is now a guiding "tunnel" from external to the apex to the atrium. The implant after having been flushed to remove air, crimped, compressed, folded or otherwise prepared is passed through the valve and into the body of the sheath. The implant is advanced until it begins to protrude out of the end of the sheath. The location is confirmed, and the implant can be deployed either in the atrium and pulled into position or deployed partially in the atrium and pulled into the valve orifice as the sheath is retracted. Once fully deployed, the implant is put into or maneuvered into a final placement. The sheath is removed while simultaneously the apical closure device is synched down to control bleeding. The sheath is pulled off of the tubing and a baseplate is put on and slide up to the apex. The implant can be found for the axial placement and the baseplate locked to secure its location in the heart. If the implant has tubing leading from the heart this is lead out through the incision site. A small incision is made at an appropriate site for the subcutaneous control unit to be placed. A pocket formed in the tissue and the tubing is tunneled to the site for the subcutaneous control unit. The tubing is then connected to the control unit. The system is now fluidically connected and can have a final flush via the control unit access sites. Typically, a non-coring needle is used to puncture into the control unit to adjust or dial in the level or amount of force transduction therapy or final flow vector volume of the device.

The described embodiments may also be implanted in a true transcatheter manner. The transcatheter method of implant is less invasive and better tolerated by patients. Additionally, the anesthesia required is significantly less and, this being the most dangerous part of any medical procedure, is highly conducive to better patient outcomes. A transcatheter procedure utilizing standard transcatheter approaches, defined as transfemoral, transvenous, and transjugular, and standard transcatheter techniques, may be used to implant all of the embodiments of the integrated system. The access site to the blood vessel may be through any clinically relevant location with the primary locations being a percutaneous femoral vein access, a subclavian access, or a jugular access. The access site is prepared with standard cardiac catheterization laboratory procedures with the Seldinger technique used to access the vessel of choice. An introducer sheath is then inserted into the vessel. Through the sheath, a guidewire, dilator, and steerable or preformed sheath is used to guide the distal end of both the guidewire and the sheath to the fossa ovalis. The sheath, dilator and guidewire can be maneuvered easily to the fossa ovlis under fluoroscopy or echocardiography imaging. The fossa ovalis is a naturally occurring depression in the right atrium in the interatrial septal wall and is a common, well known, standard anatomical landmark known to medical professionals. By puncturing the thin membrane covering over the fossa ovalis, the left atrium can be accessed from the right atrium. Various techniques exist for puncturing the membrane including a needle, a Brockenbrough needle, a radio frequency catheter, and or the sharpened guidewire are commonly used. Once the septum is punctured the site can be dilated up, or enlarged, to accommodate the implant or device delivery sheath size and to place the sheath inside the left atrium. The transeptal puncture allows access to the left atrium and the sheath is then guided, antegrade (meaning in the direction of blood flow), through the mitral or atrioventricular valve and into the left ventricle. In the left ventricle the papillary muscles are visualized. The sheath is directed or steered in between the lateral and medial papillary muscles and the advance is then stopped. A universal splayhook anchor plate is fully extended from the distal end of the introducing sheath, that extension stopping at the universal ball mount, the point at which the universal shaft receiver is coupled to the shaft. The shaft and member or distal integrated system attachment still remains housed within the delivery sheath and is connected and coupled to the universal splayhook anchor plate. The universal splayhook anchor plate is an anchoring mechanism or component with two sharpened and barbed anchor pointed wires, hook shaped with memory, extending from central universal ball mount, in a reverse taper, the wires crossing proximally to the barbed distal ends, which splay and open under direct pressure, thus allowing the papillary muscle to pass though the splayed or opened channel. The wires then close from memory immediately after the papillary muscle passes and the tension created between the connection at either end of the universal splayhook anchor plate, the lateral papillary muscle on one end and the medial papillary muscle on the other end, cause the splayhooked barbed anchor points to press in, anchor, and seat properly into the respective papillary muscles. The introducing sheath is then retracted, from the universal splayhook anchor plate, at the universal ball mount, and the shaft with the integrated system distal attachment or member is deployed or released from the introducing sheath. The integrated system distal attachment or member is deployed or released in position, either within the atrioventricular valve orifice or on the atrial annulus, depending upon the embodiment being implanted. The multi-lumen tubing is lead from the atrial side of the implant through the fossa ovalis and to the jugular access site. Near the access site a small incision is made at an appropriate site for the subcutaneous control unit to be placed. A pocket is formed in the tissue and the tubing is tunneled to the site for the subcutaneous control unit. The tubing is then connected to the control unit. The system is now fluidically connected and can have a final flush via the control unit access sites. Final adjustments can then be made to the implanted system via the hydraulically adjustable shaft. Typically a non-coring needle is used to puncture into the control unit to adjust or dial in the level of force transduction therapy or final fill volume of the device.

One of the features of healthy human heart, as shown in FIG. 1, function is proper physiological intracardiac flow defined as healthy cardiac structures (1)(2)(3)(7)(11), healthy elliptical cardiac geometry (3)(4)(5)(6), and healthy anterior and posterior ventricular vortex formation followed by healthy systolic ejection, combining both the kinetic energy of the vortex reservoir with ventricular myocardial muscular contraction, to feed the body with required oxygenated blood. During the heart's natural pumping cycle, diastole and systole, forces are naturally generated causing the valve leaflets (7) (12) (13) to open and close with considerable forces exerted on the closed or sealed atrial/ventricular leaflets (12) (13) and valve (7), especially during systole. This natural force is defined as the atrioventricular pressure gradient. This atrioventricular pressure gradient and the energy and force it delivers are critical in maintaining valvular (7)(8)(9)(10)(12)(13) and ventricular (3)(4)(5) (6) health and function. Geometric functional stability and ventricular function is maintained by imparting this energy and force (the energy and forces of the atrioventricular pressure gradient), into the ventricular walls (4) (6), septal wall (6), and apex (5) to maintain the healthy ventricle (3), to maintain the structures of the ventricle (3) (4) (5) (6), to maintain the structures of the valve (7)(8)(9)(10)(11), and provide for dynamic proper physiological hemodynamic ejection. Failing, diseased, or impaired cardiac structures, be they valves (7) or valvular components (8)(9)(10)(11)(12)(13), the heart itself (1), the ventricular free wall (4), or the septal wall (6) can have a cascading effect that results in the loss of proper physiological intracardiac flow and the loss of transducted forces into the structures of the heart (4)(6)(8)(11)(12)(13) which require these imparted forces to maintain continued health and function. This native energy and force is delivered to the structures that require it by a naturally occurring process. In the healthy heart, via the closing of the valve leaflets (12)(13) and the pulling of the subvalvular apparatus (11) and structures (8)(5)(6) in reaction to this atrioventricular pressure gradient, this energy and force is passed, moved, or transducted via the chordae tendineae (9) and papillary muscles (10) and into the ventricles (3), the septum (6), and ventricular walls (4). This resulting valvuloventricular interaction keeps the ventricular structure (3)(4)(5)(6) healthy and provides the ventricle (3) with the structural support to maintain the proper elliptical ventricular geometry and functional shape. Geometric stability and ventricular function is maintained, in an impaired or diseased heart, by imparting, mechanically via the Vortex Flow Directing Implant (100) and an integrated system (100)(600)(619)(700)(800)(900), the atrioventricular energy & force into the ventricular walls, the process called 'force transduction', to maintain the healthy ventricle (3), to maintain the structures of the ventricle (3)(4)(5)(6), to maintain the structures of the valve (7)(8)(9)(10)(11), and provides for dynamic proper hemodynamic ejection and vortical flow.

Figure 6:
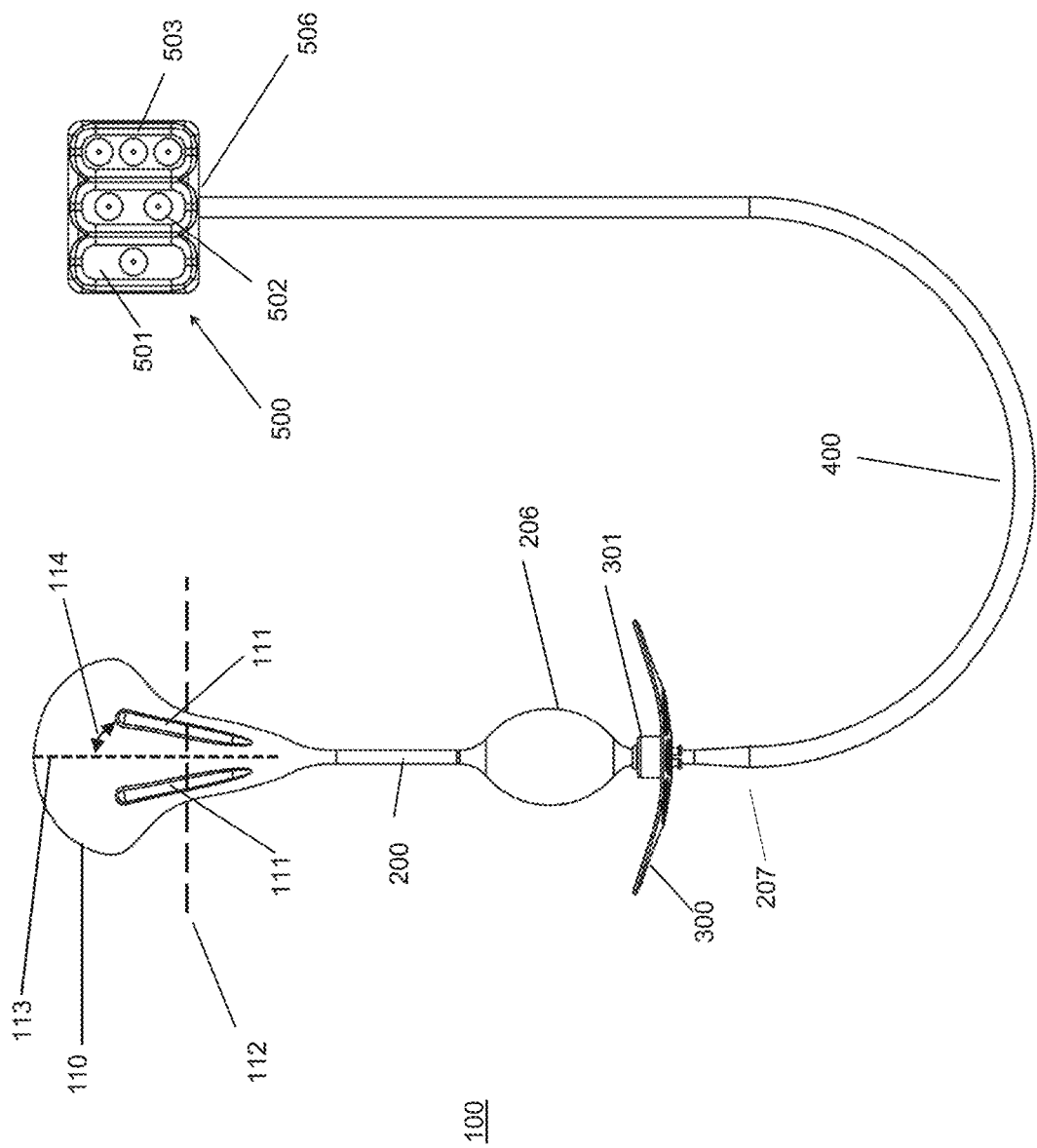
FIG. 6 is a front view of an integrated Vortex Flow Directing Implant system according to an embodiment of the present disclosure.
Figure 7:
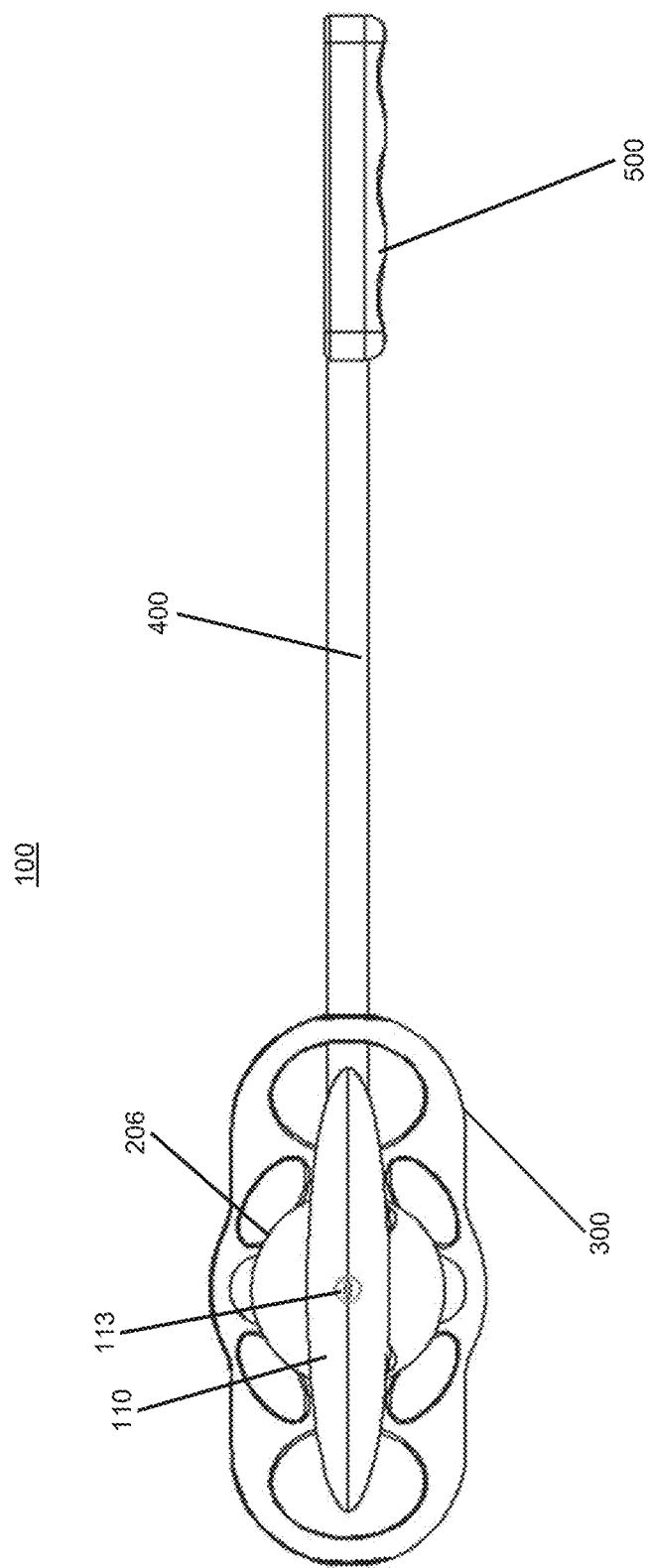
FIG. 7 is a top view down of an integrated Vortex Flow Directing Implant system according to an embodiment of the present disclosure.

In an impaired ventricle, as shown in FIG. 2, in this case a dilated cardiomyopathy, this delivery of energy and force is compromised by cardiac insult and/or pathology. The structure of the ventricle (3) then begins to lose its elliptical shape and geometry, and/or the valve (7) fails to seal and maintain the pressure of the AV pressure gradient within the ventricle. The result is a reduction or loss of the atrioventricular pressure gradient, energy and force required to maintain healthy elliptical geometry and cardiac structure, and a reduction or loss of proper hemodynamic vortical flow. This AV pressure gradient is then reduced or lost to regurgitation or backflow through the impaired valve (7), and it results in a loss of energy and force as the regurgitant volume is forced back from the ventricle (3) and into the atrium (2). This can cause a cascade of negative events such as the loss of intracardiac vortex and vortical flow, geometric shape loss (1)(3), negative remodeling of the ventricle (3) and ventricular structure (3) (4) (5) (6), valvular (7) regurgitation, and other negative symptoms that will continue to worsen in the native human heart. This device (100), as shown in FIG. 6 impedes this negative process and mechanically restores the ventricular function as it re-vectors blood entering and exiting the valve (7) and valvular orifice as it flows onto and off of the leaflets (12)(13), assists in the restoration of proper vortical formation and flow, captures the atrioventricular pressure gradient energy and force, stops the atrioventricular pressure gradient loss, and delivers this energy and force to an apical base plate (300), either ball jointed (301) or not, and then via the apical base plate (300), delivers this native energy and force into the ventricle (3), the ventricular structure (3)(4)(5), the septum (6), and ventricular free walls (4). A system is described that addresses this complex pathology.

Vortex Flow Directing Implant—The Vortex Flow Directing Implant (100), one device within an integrated system (100)(600)(619)(900), with several composite functions, parts, and/or aspects. The device consists of member (110) within a member (110) and/or a multi chamber fluid filled member (110) which is described as an inflatable flow/force guiding unit or member (110), a multi lumen (208) transducting fixed tether or shaft (200) which may be axially adjustable (202)(204) as a complete assembly (200), the assembly transitioning into an inner fixed tether or shaft (204) and an outer axially moving tether or shaft (202), which may be adjusted distally or proximally at any time, the outer axially moving tether or shaft (202) harboring an integrated inflatable axially adjusting balloon (206), which may be inflated, deflated, or adjusted at any time, with the whole of the tether or shaft transitioning (207) into a multi lumen tube (400) after exiting the apex (5). The tether or shaft (200) is fixed to the apex (5) of the heart by a base plate (300), either ball jointed (301) or not and may have a piston (307) which adjusts the tether or shaft (200) for axial height (204), initially mechanically secured onto the apex (5), and then after transitioning into a multi lumen connective tube (400), to a control unit (500) that may in some embodiments house or harbor intracardiac sensing components, adjusts the device orientation and performance via a fluid communicating system when connected (506) to the multi lumen tube (400).

The member (110) may have any shape, including a manta shape (120) that, FIGS. 8 & 10 with its 'wings' (115), may intercept, vector, and redirect blood flow from the atrium (2) to the ventricle (3), that manta shape (110) being larger with its 'wings' (115) in the atrium (2) and tapering sharply (118) (119) in the ventricle (3). The member (110) may in some embodiments harbor a latitudinal ('wing to wing') shape support structure (117)(116) a skeletal crescent beam with lumen (116) fixed to the distal end of the axially moving shaft (202) with two force-transducting trusses (117) connecting to the proximal end of the axial moving shaft (202) inside of the member (110) to aid in the hemodynamic interception, hemodynamic vector, and transduction (meaning the capture, harness, transfer, and movement of this energy and force) of captured atrioventricular energy and force (AV pressure gradient) and mechanically does two things: the member (110), in any shape, or in the manta shape (120) intercepts atrial (2) blood and re-vectors (111) it to assist, enhance, or restore the vortex, vortical flow, and natural physiologic blood flow vector passing blood over, across, and off of the valve leaflets and into the ventricle (3) and it captures (112) the native atrioventricular pressure gradient, or the ventricular energy and force, utilizing the valvular (12)(13) and subvalvular structures (11) as they coapt or seal (12)(13)(112) and thus 'grab, flex, and pull' (112) on the member (110) in systole. The 'grabbing, flexing, and pulling' (more precisely described as atrioventricular pressure gradient forces acting on exposed area of the member (110) at the line of coaptation (112)) by the valvular (7)(12)(13) and subvalvular structures (9)(10)(11), mechanically replaces and imparts the disturbed or lost native valvular and subvalvular force (driven by the systolic atrioventricular pressure gradient) interaction with the ventricle (3), the ventricular structures (4)(5)(7), the septal wall (6), and ventricular walls (4) by transducting, meaning the capture, collection, and transfer of existing native energy & force, this native force via the apical base plate (300), to and in contact with the apex (6), the ventricle (3), ventricular structures (4)(5)(6)(7), and ventricular wall (4). This is one systemic function and/or aspect of this device within an integrated system.

The member (110) intercepts, steers, re-directs, and/or FIGS. 8, 9, 10 changes hemodynamic vector of the blood flowing onto and off of valvular leaflets (7)(12)(13). Flow channel' creating ribs (111) running at angle (114) along the surface of the member (110) steer the intercepted flow of blood onto and off the valve leaflets (12) (13), and facilitates proper vector (111) (12) (13) upon entry into the ventricle (3). This hemodynamic re-vector (110) (114) (111) (12) (13) mechanically restores, enhances, and/or assists the natural physiologic vector thereby facilitating the enhancement, restoration, and/or re-creation of ventricular vortex, critical to physiologic healthy flow. This is one systems function and/or aspect of this device within an integrated system.

Figure 11:
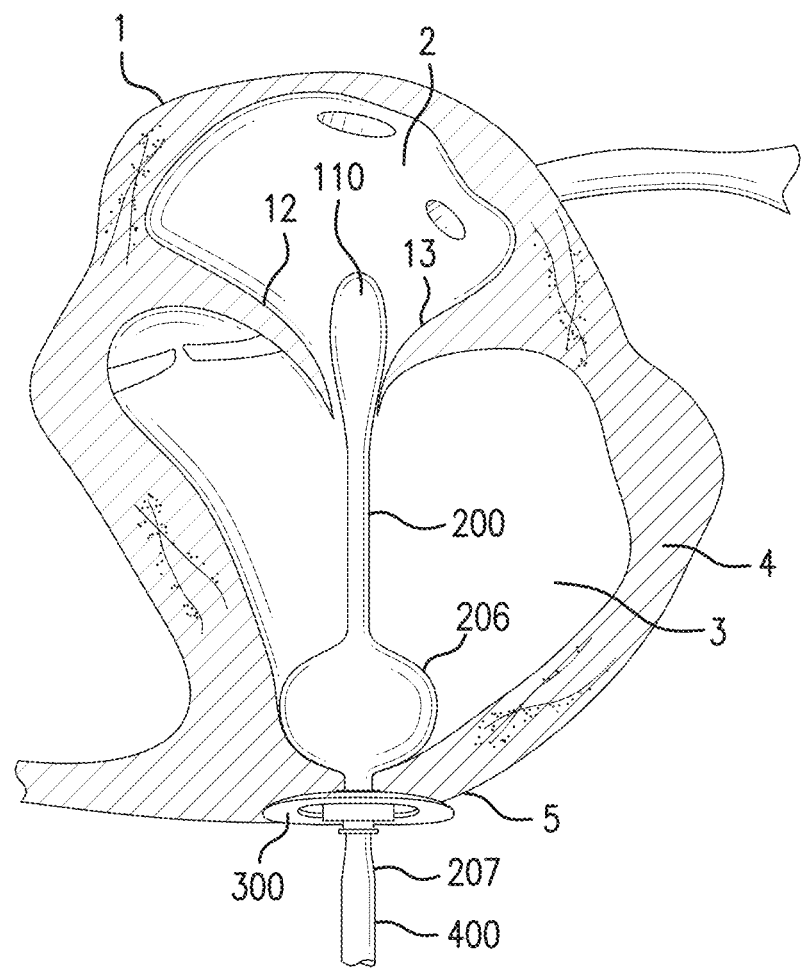
FIG. 11 illustrates a member capturing and harnessing energy and force enabling force transduction to occur; the member being engaged by the anterior and posterior leaflet In Situ or inside the heart according to an embodiment of the present disclosure.
Figures 12, 13:
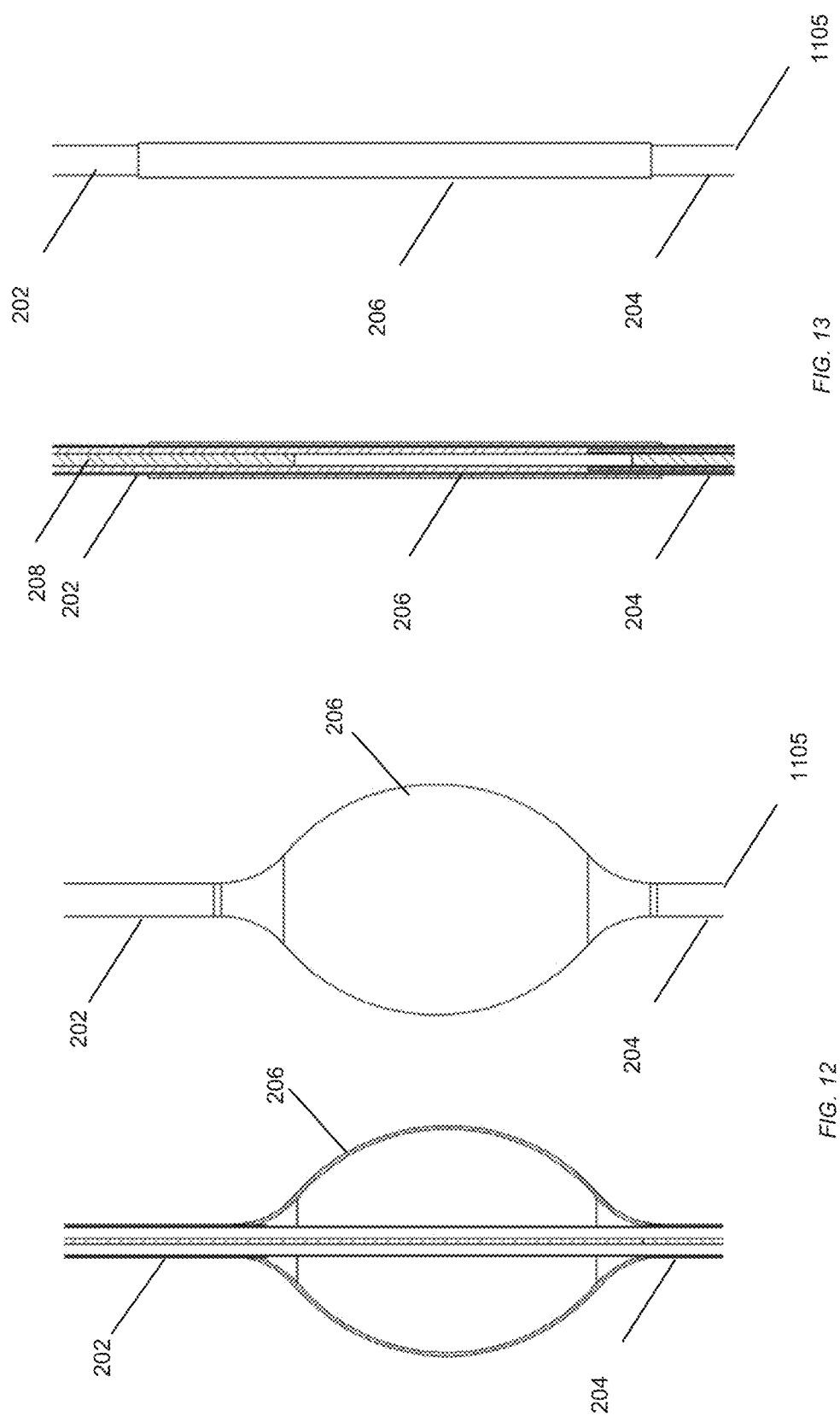
FIG. 12 illustrates an axial adjusting balloon inflated in a cross-section view and an exterior view according to an embodiment of the present disclosure.
FIG. 13 illustrates an axial adjusting balloon of FIG. 12 deflated in a cross-section and an exterior view according to an embodiment of the present disclosure.
Figure 14:
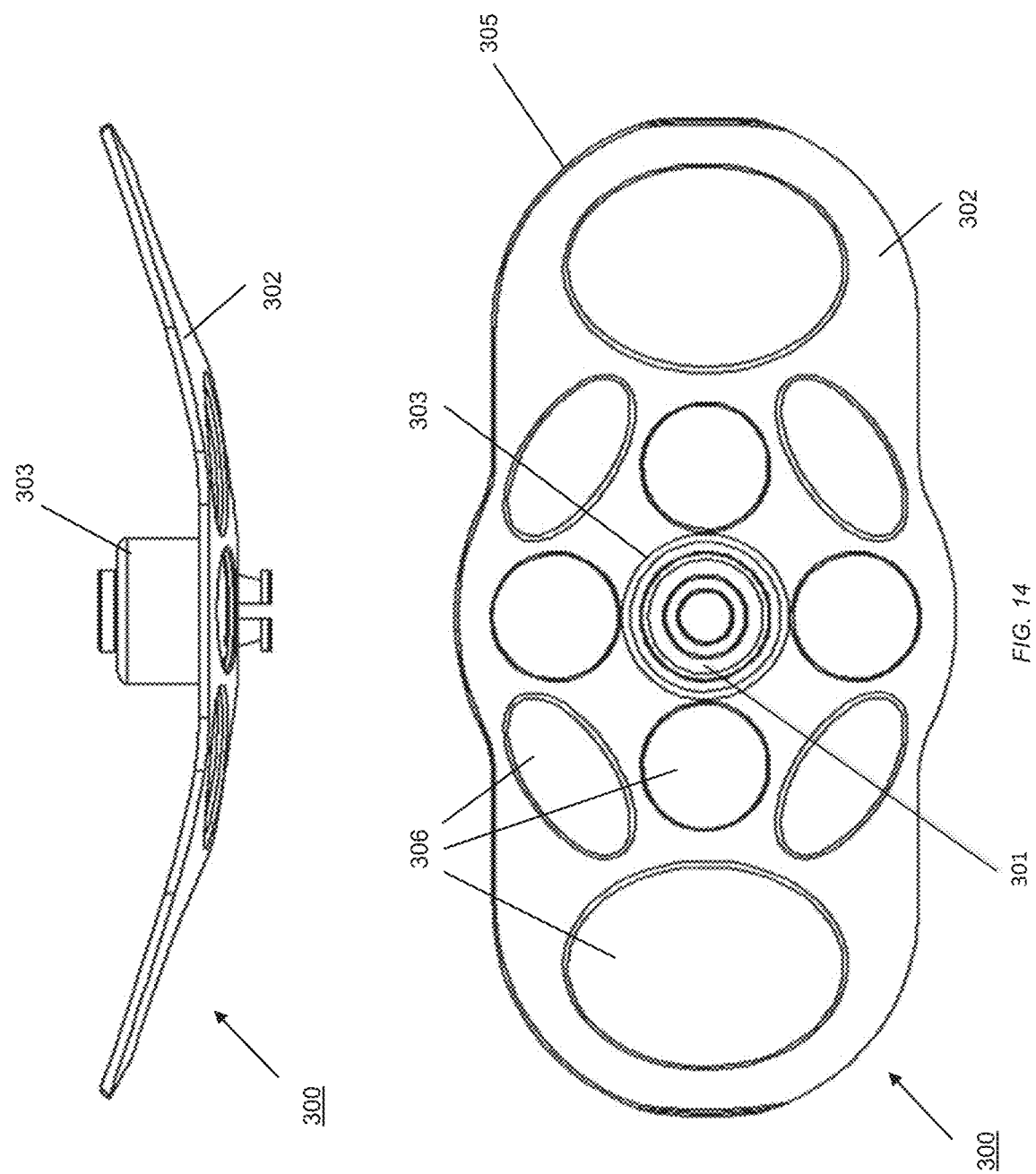
FIG. 14 illustrates a front view and a top view of an apical base plate with a ball joint according to an embodiment of the present disclosure.

The valvular leaflets (12)(13) and FIG. 3, 4 subvalvular structures (9)(10)(11) 'grabbing, flexing, and pulling' (112) of the member (110) mechanically replaces lost valvuloventricular interaction FIG. 11 by transducting, meaning the capture, collection, and transfer of existing native energy & force, this native force via the apical base plate (300) which FIG. 14 then, by connection via the tether or shaft (200) to and contact with the apex (5), ventricle (3), and ventricular wall (4), either utilizing specific edge shapes (305) or not, delivers this physiologic produced natural energy and force (atrioventricular pressure gradient energy and force) into the ventricular structure (3)(5)(6)(4) thereby inducing reverse remodeling (positive geometric reshaping) of that ventricular structure (3), valvular structure (7), and cardiac structure (1). There is a resulting valvulo-ventricular (7) (3)(4) wall interaction that provides the ventricle (3) with structural support by maintaining the elliptical geometry (1)(3)(4), preventing papillary muscle (10) displacement, and providing functional support required for proper ventricular health, healthy geometric proportion, and proper hemodynamic or blood ejection. This is one systemic function and/or aspect of this device within an integrated system.

The loss of any portion of the atrioventricular pressure gradient can cause serious cardiac (1), ventricular (3), and valvular (7) pathology and compromise this native energy and force. The preservation of the atrioventricular pressure gradient, by preserving geometric cardiac (1) and ventricular shape (3) and valvular structure (7) may be important to ventricular (3) and overall health. This atrioventricular pressure gradient, its energy and force, and its positive resulting ventricular (3) and valvular (7) health effects can be mechanically preserved by placing, fixing, and/or securing the member (110) within the atrioventricular valvular orifice (16). The member (110), while the valve leaflets (12) (13) simultaneously capture (112) and harness the energy and force of the atrioventricular pressure gradient by surface area contact between the valve leaflets (12)(13) and the member (110), may in some embodiments seal the ventricle (3) by facilitating the sealing of the ventricle (3) by the valvular leaflets (12) (13) topographically sealing to the member (110) at the point at which they come into contact (112) with the member (110). This sealing contact (112), whether complete or not and occurring because of the mere presence of the member (110) in the atrioventricular valvular orifice (16), does slow or impede the loss of the atrioventricular pressure gradient in the presence of a compromised or failing native or prosthetic valve. The mere presence FIGS. 10 & 11 of the member (110) may in some embodiments be sufficient to preserve the ventricular pressure of the atrioventricular pressure gradient. Pressure being independent of volume, the member (110) is placed (7)(12)(13)(14)(15)(16) to obstruct, reduce loss, or stop some or all of the systolic atrioventricular pressure gradient loss to thus preserve the energy and force of the atrioventricular pressure gradient, while at the same time transducting or transferring the required energy and force into needy cardiac structures (3)4(5)(6)(7)(8), and thus, maintain maximum efficiency of the cardiac cycle. The regurgitant volume, or the blood flowing back through the valve leaflets (12) (13) and into the atrium (2) from the ventricle (3), is the loss of the atrioventricular pressure gradient visualized.

The mechanical movement and use of this native gradient energy and force to repair, restore the native elliptical shape (3), or geometrically reshape (reverse remodel) the ventricle (3), the ventricular structures (3) (5) (6) (4), and ventricular walls (4), while simultaneously reducing, stopping, and/or impeding atrioventricular pressure loss, is an integrated systemic function common to all embodiments. The atrioventricular pressure gradient energies and forces, through the device (100), become a restoring, mechanically delivered, and re-purposed essential requirement for healthy valvular (7) and ventricular function (3)(4). This is one systemic function and/or aspect of this device as an integrated system.

Figure 15:
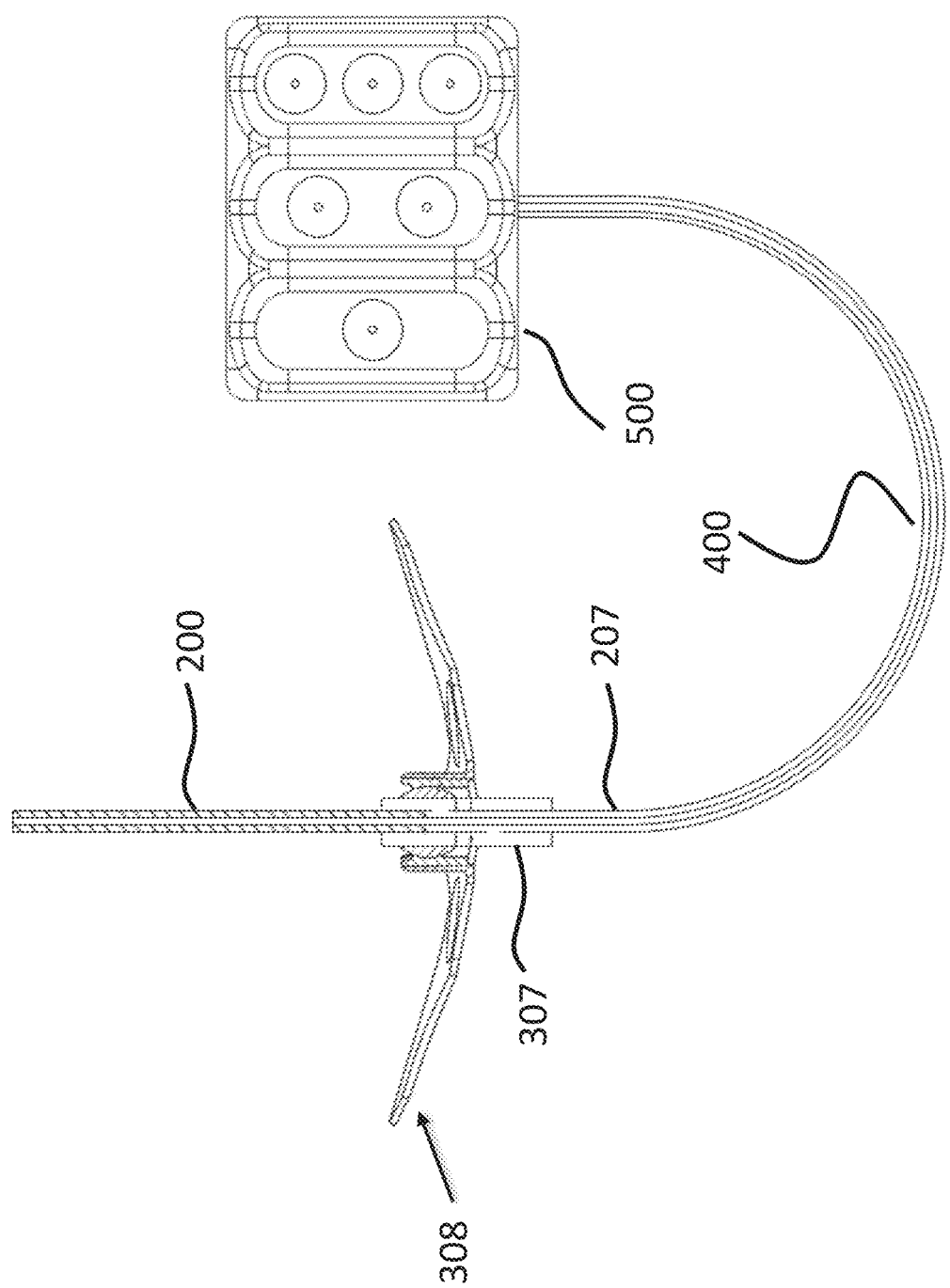
FIG. 15 illustrates a cut-away cross-sectional interior view of a hydraulically adjusting base plate with axial adjusting piston according to an embodiment of the present disclosure.
Figure 16:
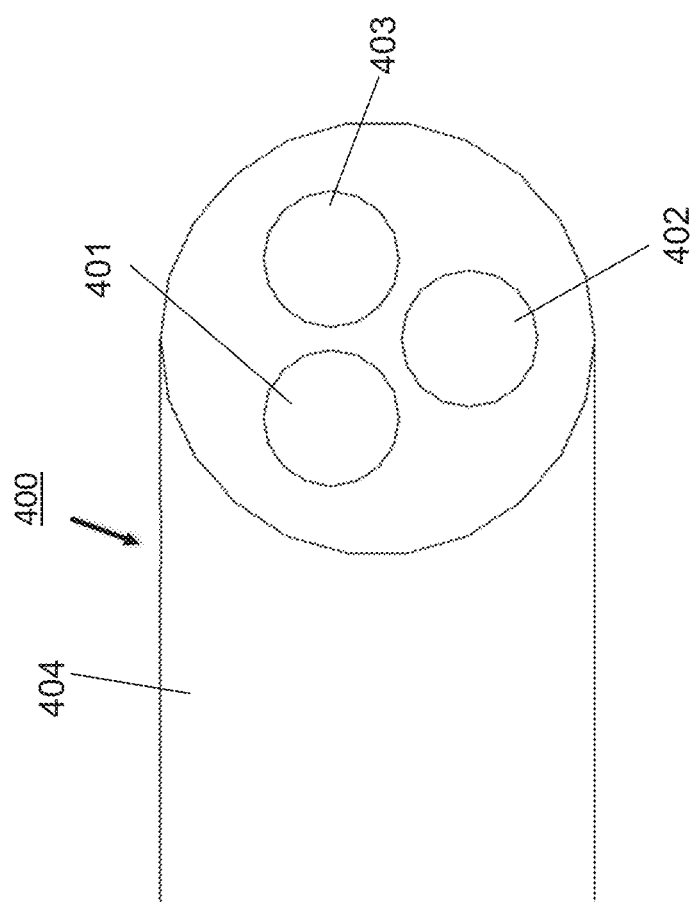
FIG. 16 illustrates a cut-away of a multi lumen tubing in perspective view according to an embodiment of the present disclosure.
Figure 17:
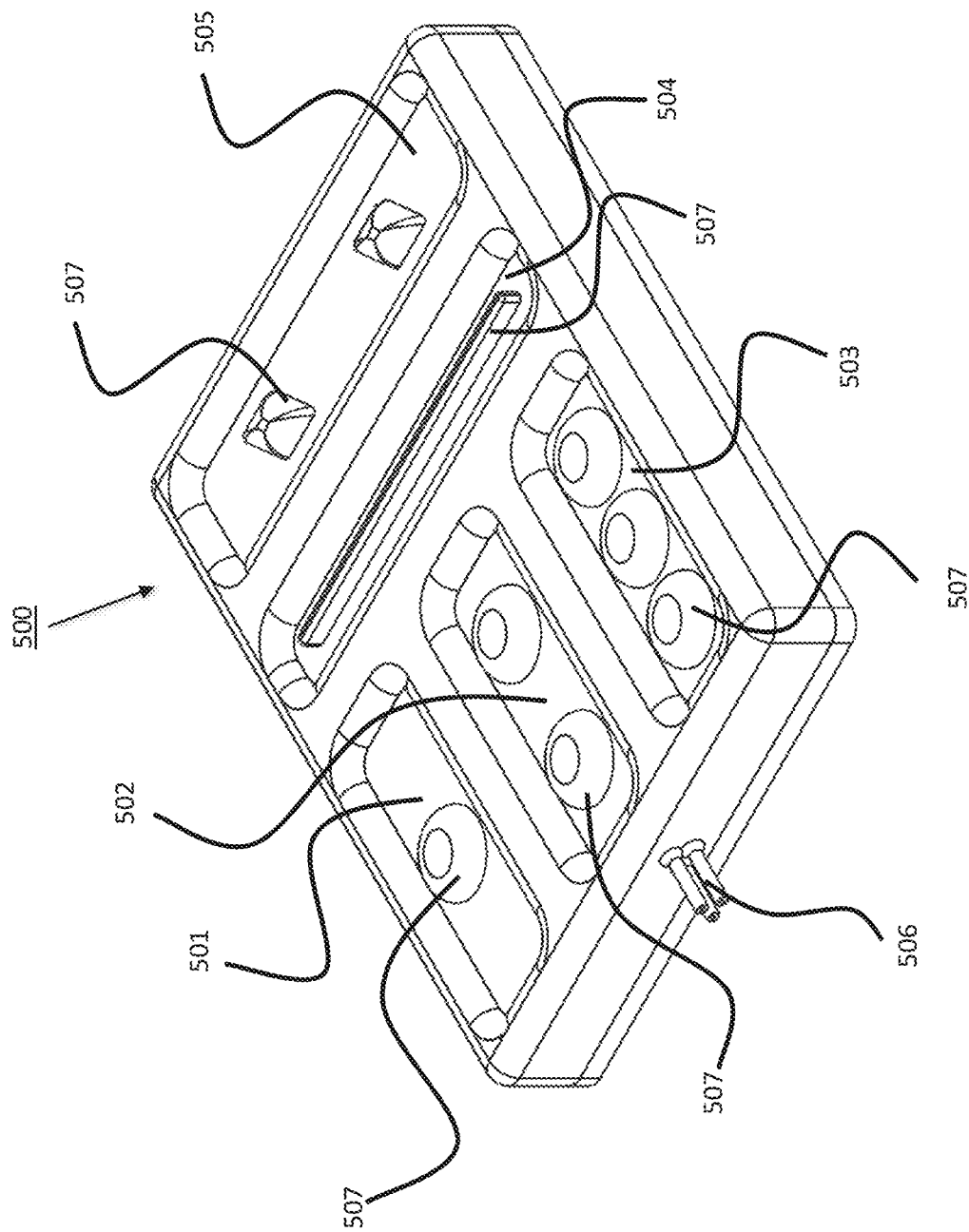
FIG. 17 illustrates a perspective view of a control unit with five independent chambers according to an embodiment of the present disclosure.

The fixed ball jointed (301) apical base plate (300)(302), with round oval cutouts (306), may in some embodiments FIGS. 14, 15 have an axial tether or shaft (200) adjusting piston (307) which is hydraulically controlled (308) and in communication via the FIG. 16 multi-lumen tubing (400) with the control unit (500), to allow fibrous tissue in-growth (306) for long term security, pulls the apex (5) upward in systole and releases the apex (5) in diastole and, in conjunction with the elongated (305) therapeutic extensions of the ball jointed (301) apical base (300)(302) plate extending up the sides of the ventricles (3), imparts by contact (300)(305), specific shape (305), and fixation (200)(300)(302)(306) this mechanically transducted or transferred energy into the ventricles (3). This induces a physiologic and therapeutic response by mechanically replacing the lost valvulo-ventricular interaction (11)(3)(4) required to maintain a healthy ventricle (3), ventricular free wall (4), and a healthy geometric elliptical ventricular (3)(4)(6) shape. The control unit (500) has FIG. 17 three independent vertical contained chambers (501,502,503) and two independent horizontal contained chambers (504)(505), each identifiable below the skin by palpable protrusions, one palpable vertical protrusion for chamber one (501), two palpable vertical protrusions for chamber two (502), three palpable vertical protrusions for chamber three (503), one palpable horizontal protrusion for chamber four (504), and two palpable horizontal protrusion points for chamber five (505), with a multi-lumen single connection point (506) placing the control unit (500) in communication, via the shaft (200), with the member (110), and has a needle access pad (500) of ePTFE or any other material, which may in some embodiments allow fibrous tissue in growth. In one vertical chamber, fluid is introduced or removed to increase or decrease the member (110) girth or width. Increasing or decreasing this member girth alters the vector of blood and adjusts (112) the amount of force captured and transducted to the ventricle (3) by increasing or decreasing the surface area contact of the valve's leaflets (12)(13) on the member (110) along the commissural line or line of coaptation (112). In one vertical chamber, fluid is introduced or removed from the integrated inflatable axial adjusting balloon (206) to increase or decrease (202) the axial positioning shaft (202) of the member (110) as reverse re-modeling (3) occurs and to remove excess ventricular blood volumes (206) in specific cases such as dilated cardiomyopathy. In one vertical chamber, fluid is added or removed to create crescent shaped articulation (117)(115) in the member (110) 'wings' (115), either anterior or posterior, to better vector the intercept of atrial (2) blood by introducing fluid into the 'wing' chambers (117) via the skeletal crescent beam with lumen (116). In both horizontal chambers (504,504) sensing communications power, data storage, or equipment may be housed. This is all one systemic function and/or aspect of an integrated device as a system.

Sensing nodes may be placed at any location within the member (110), within or on any component (100)(200)(300) (400)(500)(600)(619)(700)(800)(900), within or on any structure (1), and/or anywhere on this integrated system thereby using the inflatable member (110), the shaft (200), the apical base plate (300), the multi lumen tubing (400), the control unit (500) and/or any and all other added part or parts (100)(200)(300)(400)(500) of the system as an intracardiac 'sensing harbor' for intracardiac sensing components and nodes. In some embodiments, these sensors may be in direct or indirect contact and communication with the control unit (500) via FIG. 16, 17 the multi-lumen tubing (400). These harbored sensors may in some embodiments collect, store, and report to an external device all information and data that is collected, monitored, and gathered. This is all one systemic function and/or aspect of this integrated device as a system.

Figure 19:
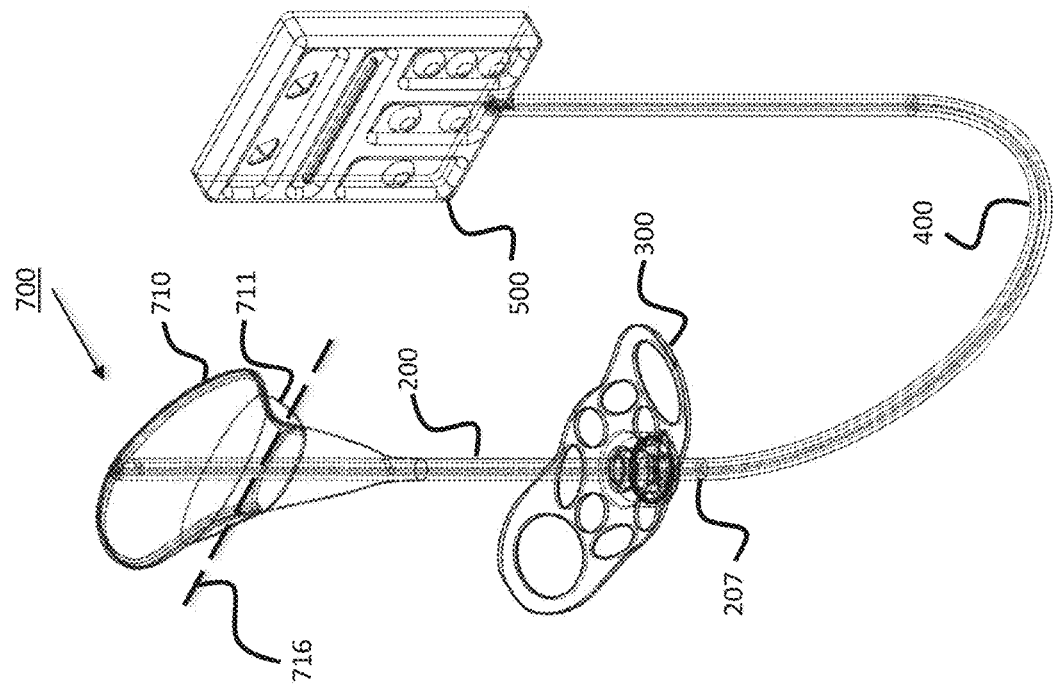
FIG. 19 is a perspective view of a Vortex Flow Directing Implant according to an embodiment of the present disclosure.
Figure 18:
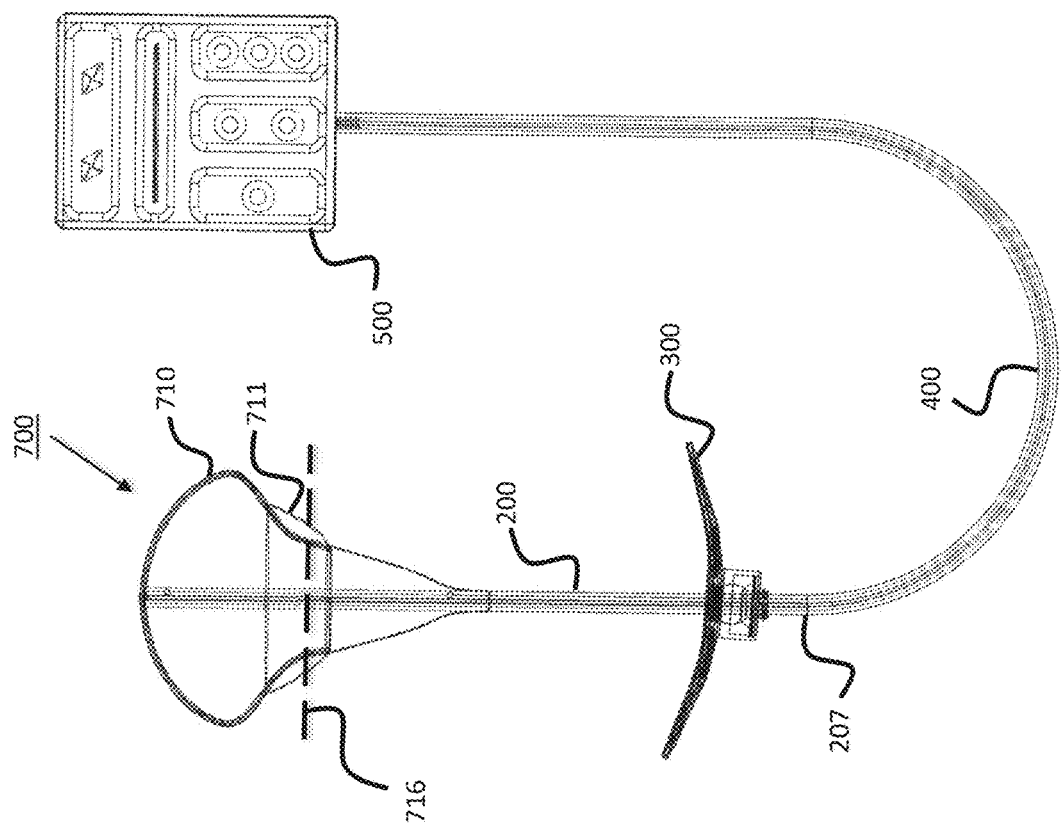
FIG. 18 is a side view of a Vortex Flow Directing Implant with the attached inflatable belt on the member according to an embodiment of the present disclosure.
Figure 20:
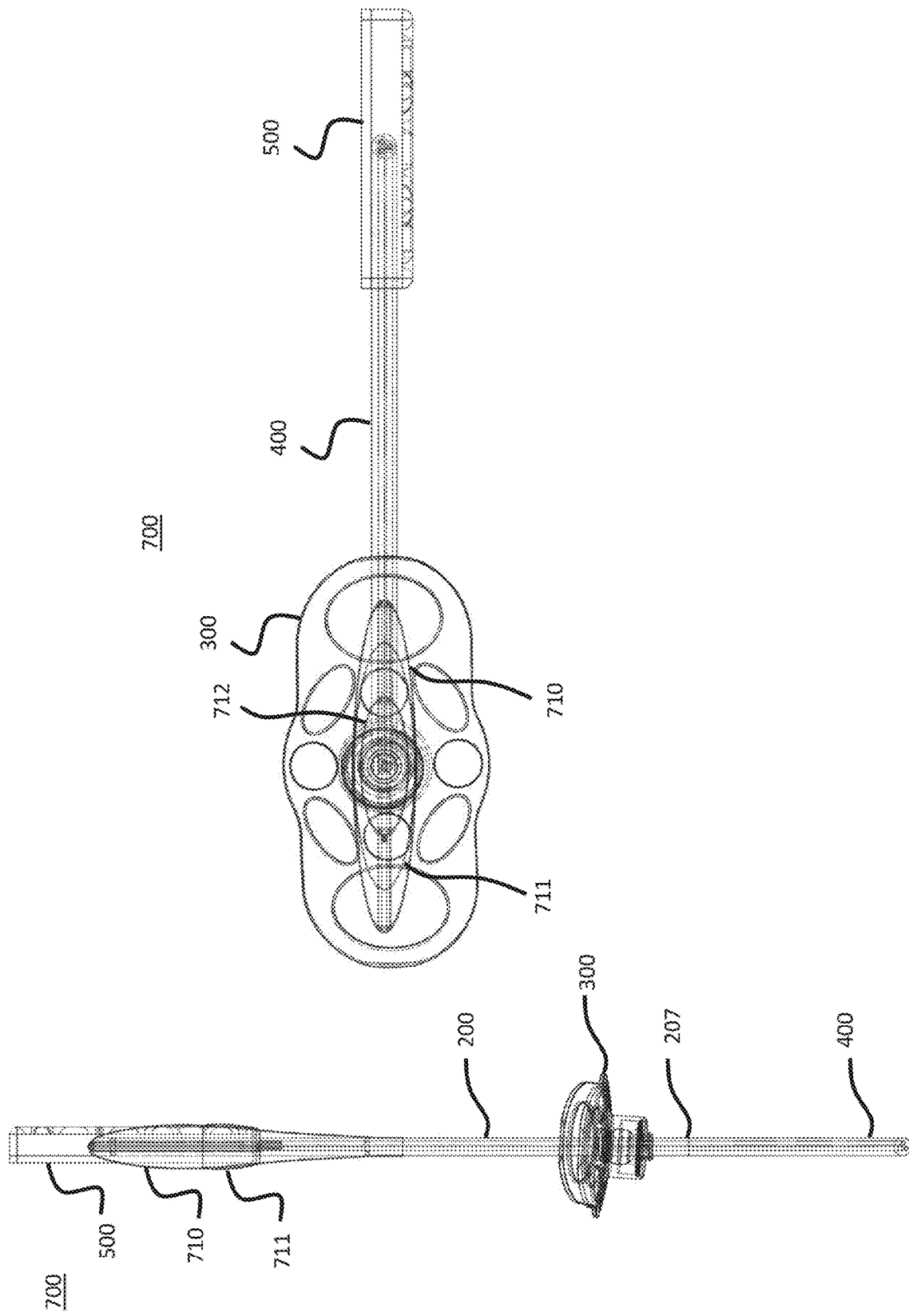
FIG. 20 is a top down view of a Vortex Flow Directing Implant according to an embodiment of the present disclosure.

In various embodiments, a Vortex Flow Directing Implant (700), described in connection with FIGS. 18 and 19, is substantially identical to the system (100) described hereinabove, with the substantial differences noted herein. For example, the member (710) is encased and circled (711) in an FIG. 21 inflatable 'belt' (711) intended to provide an adjustable sealing point or surface for the valvular leaflets (12) (13) to seat and/or seal (716) upon. The secured and/or fixated member (710) and is attached, fixated, and/or secured to the tether or shaft (200). This inflatable 'belt' (711) is integrated into the member (710) and may be inside (712) the lumen of the member (710) or outside (711) the lumen FIG. 22 of the member (710) positioned along the line of coaptation (716) or at the point the leaflets come into contact (716) with the member (710)(711). In this embodiment, the member (710) is the distal attachment to the force transducting or transferring fixed shaft (200) which is axially adjustable (206)(202)(308) as a complete assembly, may contain FIG. 22 filling points; one upper fill point (713), one lower fill point (714), one belt fill point (715). The tether or shaft (200) transitioning into an inner fixed shaft (204) and an outer axially moving shaft (202), the outer axially moving shaft (202) harboring an integrated inflatable axially adjusting balloon (206), with the whole of the shaft transitioning (207) into a multi lumen tube (400) after exiting the apex (5). The shaft (200), in its entirety, is fixed to the apex (5) of the heart by a base plate (300), either ball jointed (301) or not and either piston adjusted (307)(308) for axial adjustable height or not initially mechanically secured onto the apex (5), and then, after transitioning (207) into a multi-lumen tube (400), to a control unit (500) that, may in some embodiments house or harbor intracardiac sensing components, adjusts the device performance via a fluid communicating system when connected (506) to the multi lumen tube (400). This is all one systemic function and/or aspect of this integrated device as a system.

Figure 24:
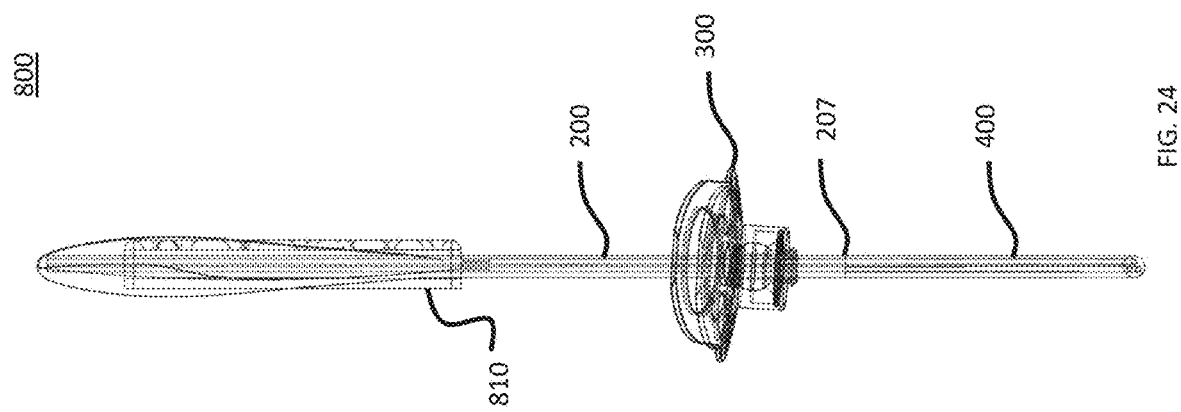
FIG. 24 is a side view of a Vortex Flow Directing Implant according to an embodiment of the present disclosure.
Figure 23:
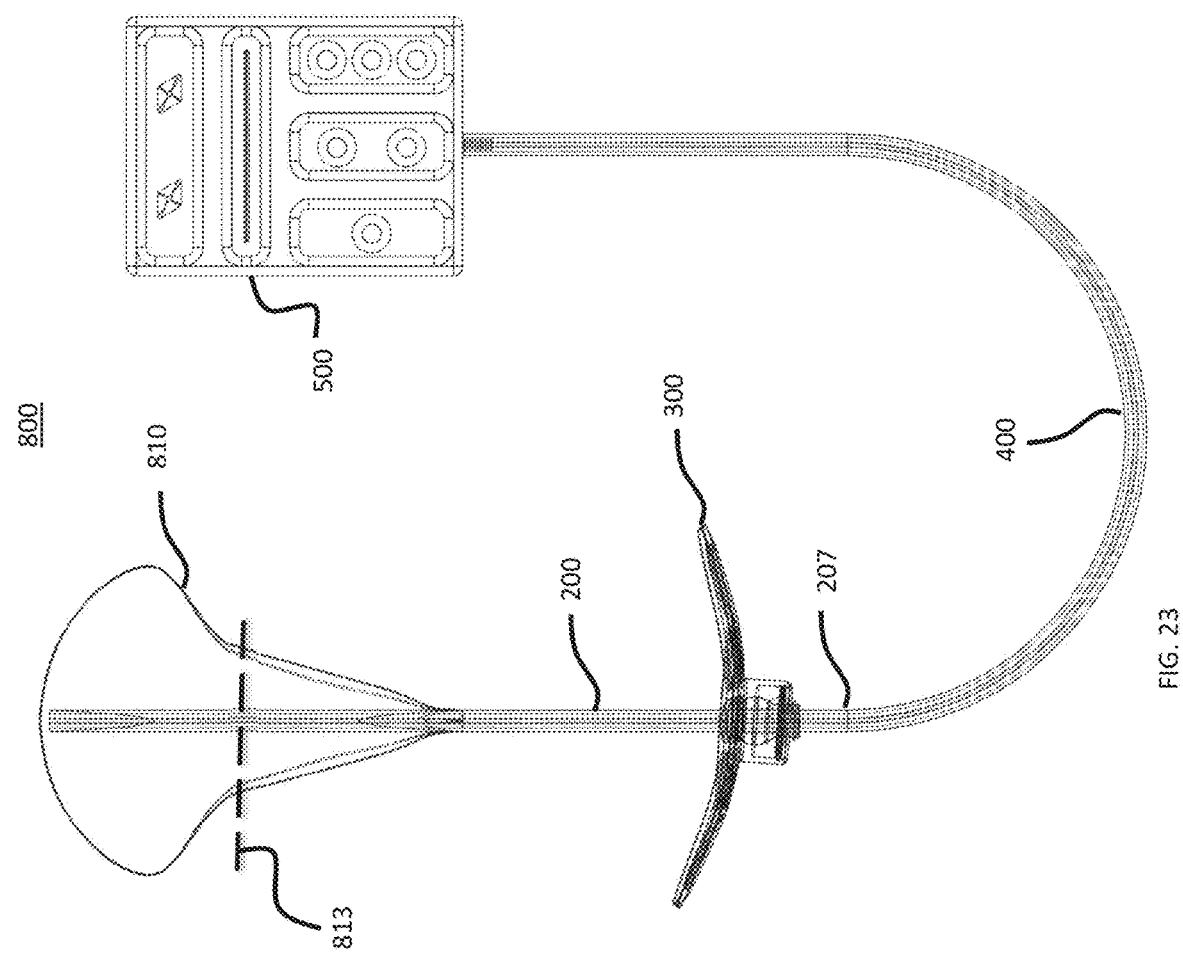
FIG. 23 is a front view of a Vortex Flow Directing Implant according to an embodiment of the present disclosure.
Figure 25:
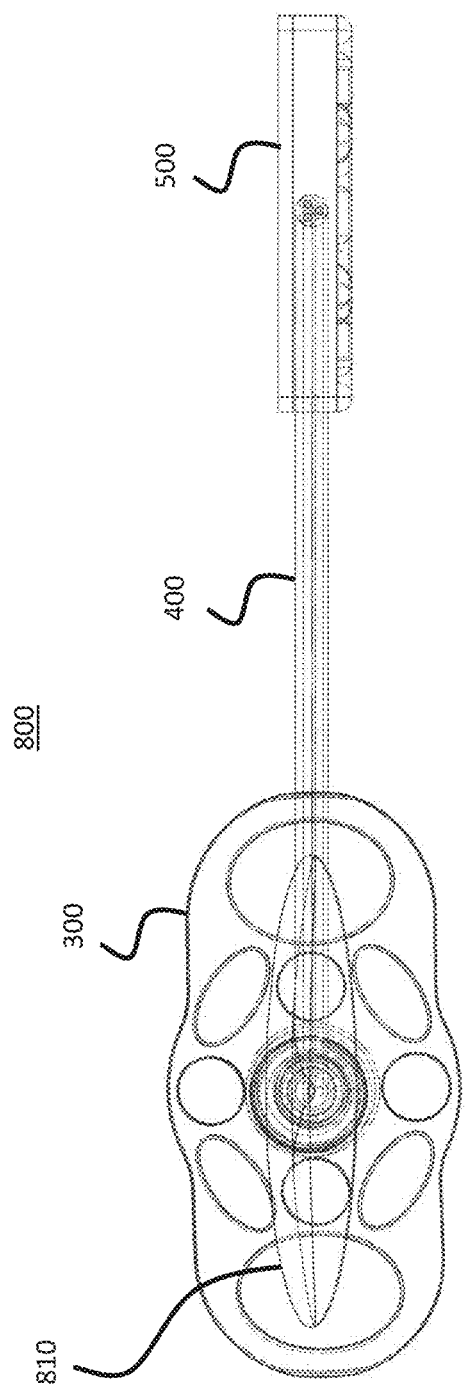
FIG. 25 is a top down view of a Vortex Flow Directing Implant according to an embodiment of the present disclosure.

In various embodiments, a Vortex Flow Directing Implant (800), described in connection with FIGS. 23 and 24, is substantially identical to the system (100) described hereinabove, with the substantial differences noted herein. For example, the member (810) is FIG. 26 semi-lunar shaped, malleable yet rigid, 'manta' shaped (120) and/or any other shape, being solid or rigidly malleable on the posterior half (811)(13) and inflatable (812)(12) on the anterior portion. (See FIG. 27) This may be reversed as well, meaning the posterior half (13) is FIG. 28 inflatable (812) and the anterior portion (12) is solid FIG. 29 (811). This creates the semi-lunar profile that the native mitral valve naturally exhibits, meaning a semi-lunar line of coaptation (813), and may sustain the atrioventricular pressure gradient in a more functional and efficient manner. In this embodiment, the member (810) is the distal attachment (200) to the a multi lumen transducting fixed tether or shaft (200) which is axially adjustable (202)(206)(308) as a complete assembly (800)(100), the assembly transitioning into an inner fixed shaft (204) and an outer axially moving shaft (202), the outer axially moving shaft (202) harboring an integrated inflatable axially adjusting balloon (206), with the whole of the shaft transitioning (207) into a multi lumen tube (400) after exiting the apex (5). The shaft (200), in its entirety, is fixed to the apex (5) of the heart by a base plate (300), either ball jointed (301) or not and either piston adjusted (307)(308) for axial height or not, initially mechanically secured onto the apex (5), and then, after transitioning (207) into a multi lumen tube (400), to a control unit (500) that, may in some embodiments house or harbor intracardiac sensing components, adjusts the device performance via a fluid communicating system when connected (506) to the multi lumen tube (400). This is all one systematic function and/or one aspect of this integrated device as a system.

Figure 30:
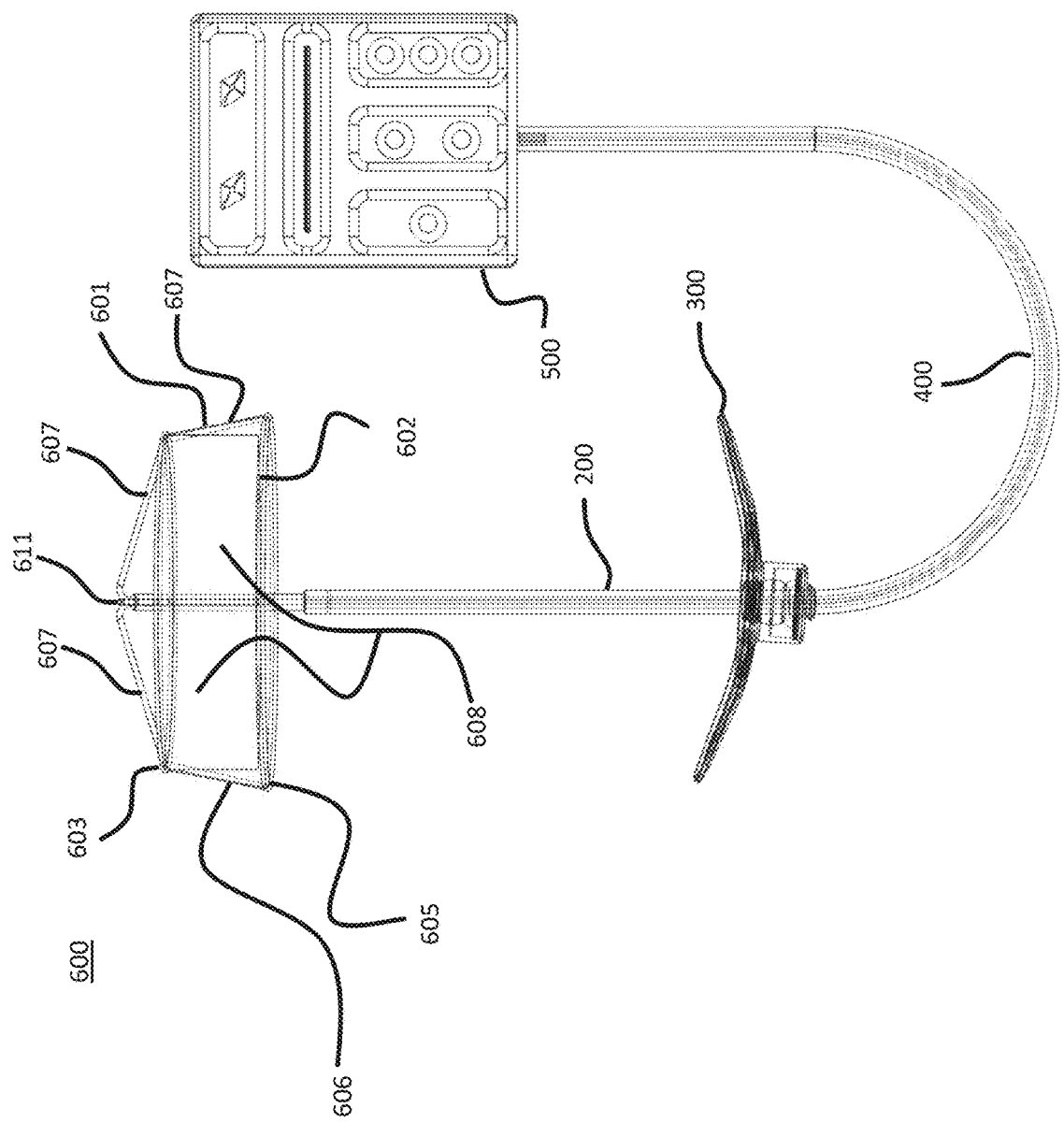
FIG. 30 is a front view of a Dual Force Pressure Mitigating Implant system according to an embodiment of the present disclosure.

In various embodiments, a Dual Force Pressure Mitigating Implant (600), described in connection with FIG. 30, is similar to the system (100) described hereinabove, with the substantial differences noted herein. The Dual Force Pressure Mitigating Implant (600) is a device within an integrated system (200) (300) (400) (500) (100) (600) (700) (800) (900) with several composite components, sets of component, functions, parts, and/or aspects. The Dual Force Pressure Mitigating Implant (600) consists of two assembled component systems: the FIG. 34, 35 the pressure mitigating assembly (601) consisting of the structural housing (604), made up of components (603)(605)(606)(607)(617), each self-expanding, made of nitinol, elastic, or spring-like material, the gradient funneling skirt (608), and the fixation point (611) is the first component system. The second component system is the 'one way valve' or 'check valve' (602). The 'one way valve' or 'check valve' (602) is contained, mounted, and/or housed within the pressure mitigating assembly (601), consisting of the structural housing (604) and the gradient funneling skirt (608). This finished component assembly (601), the pressure mitigating assembly (601), is then attached to the components (200)(300)(400)(500); the tether or shaft (200), the apical base plate (300), which may in some embodiments be ball jointed (301) and/or hydraulically axially adjustable (307)(308), the multi-lumen communication tubing (400), and the control unit (500) and together create the embodiment.

Figure 32B:
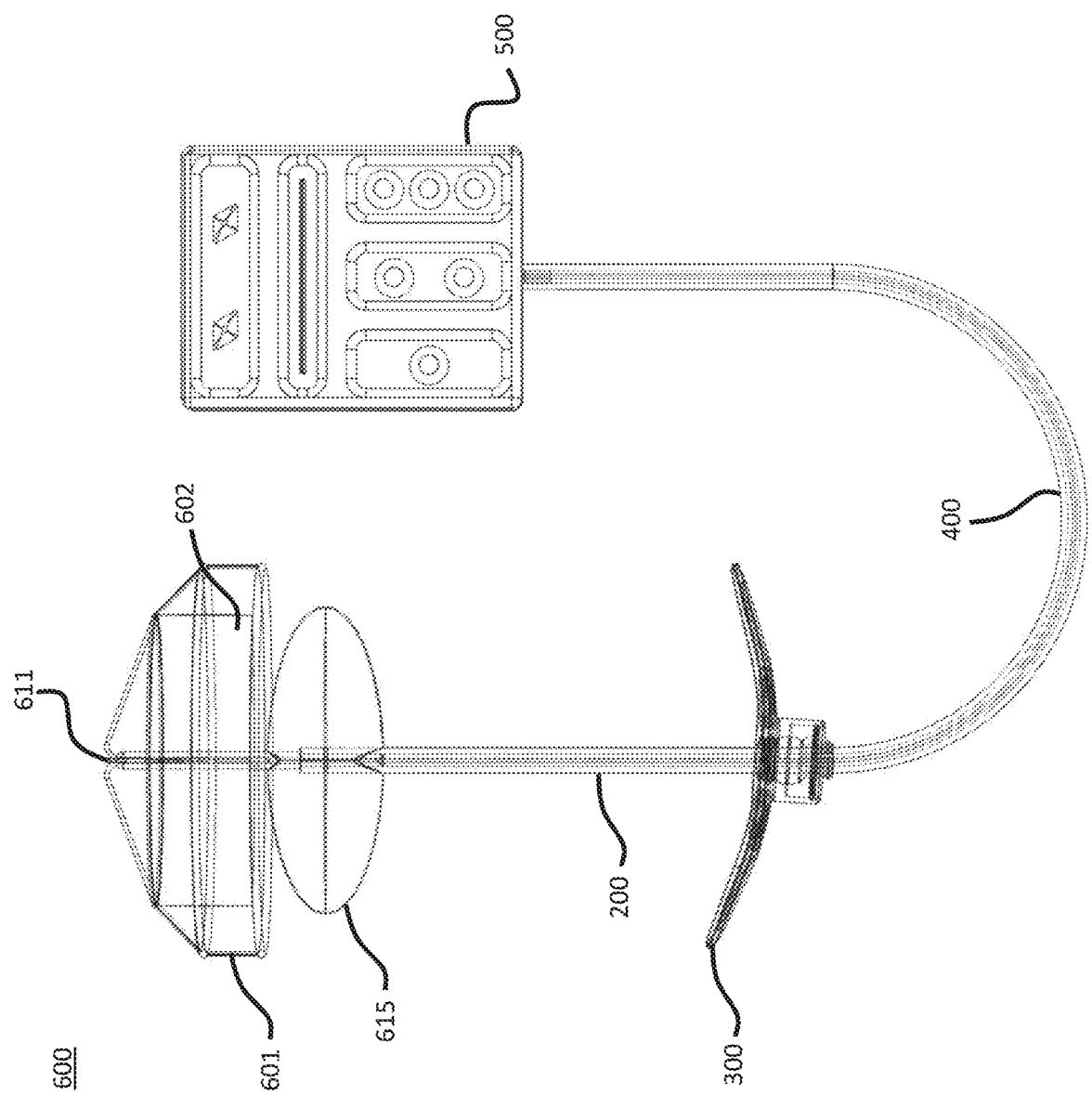
FIG. 32B is a front view of a Dual Force Pressure Mitigating Implant system with a coapting-vectoring member according to an embodiment of the present disclosure.

The combination of these two-component assemblies (601)(602), the pressure mitigating assembly (601) and the 'one way' or 'check valve' (602) become the FIGS. 30,31, 32A Dual Force Pressure Mitigating Implant (600). The tether or shaft (200) in communication with the control unit (500) via the multi-lumen tubing (400), may in some embodiments be used to axially adjust (206) (307) (308) the tension or seal on the atrial (2) side of the valve (7) at the point which the gradient funneling skirt (608) connected to the proximal annular ring (605) meets native or prosthetic valve (7) annulus (8). The axial height of the shaft (200) also adjusts the amount of transductive force (meaning the mechanical capture, harness, collection, and transfer of native energy and force) delivered FIG. 33 by increasing or decreasing the amount of load or pressure on and in the structural housing (604), made up of all of the nitinol, spring-like, self-expanding components (603)(605)(606)(607)(617), as it sits on the native atrial (2) annulus (8), mechanically delivered to ventricle (3), the septum (6), and/or ventricular walls (4). By increasing or decreasing the load placed onto or into the nitinol lateral (606), distal suspension ring (603), proximal annular ring (605), lateral struts (606), and crescent shaped struts (607) making up the structural housing (604) the dual force or amplified force transduction is created. This combining or the joining of these two components, the pressure mitigating assembly (601) and the 'one way valve' or 'check valve' (602), the tether or shaft (200), the apical base plate (300), the multi-lumen communications tubing (400), and the control unit (500) now completes the integrated system referred to as the Dual Force Pressure Mitigating Implant (600).

Figure 34:
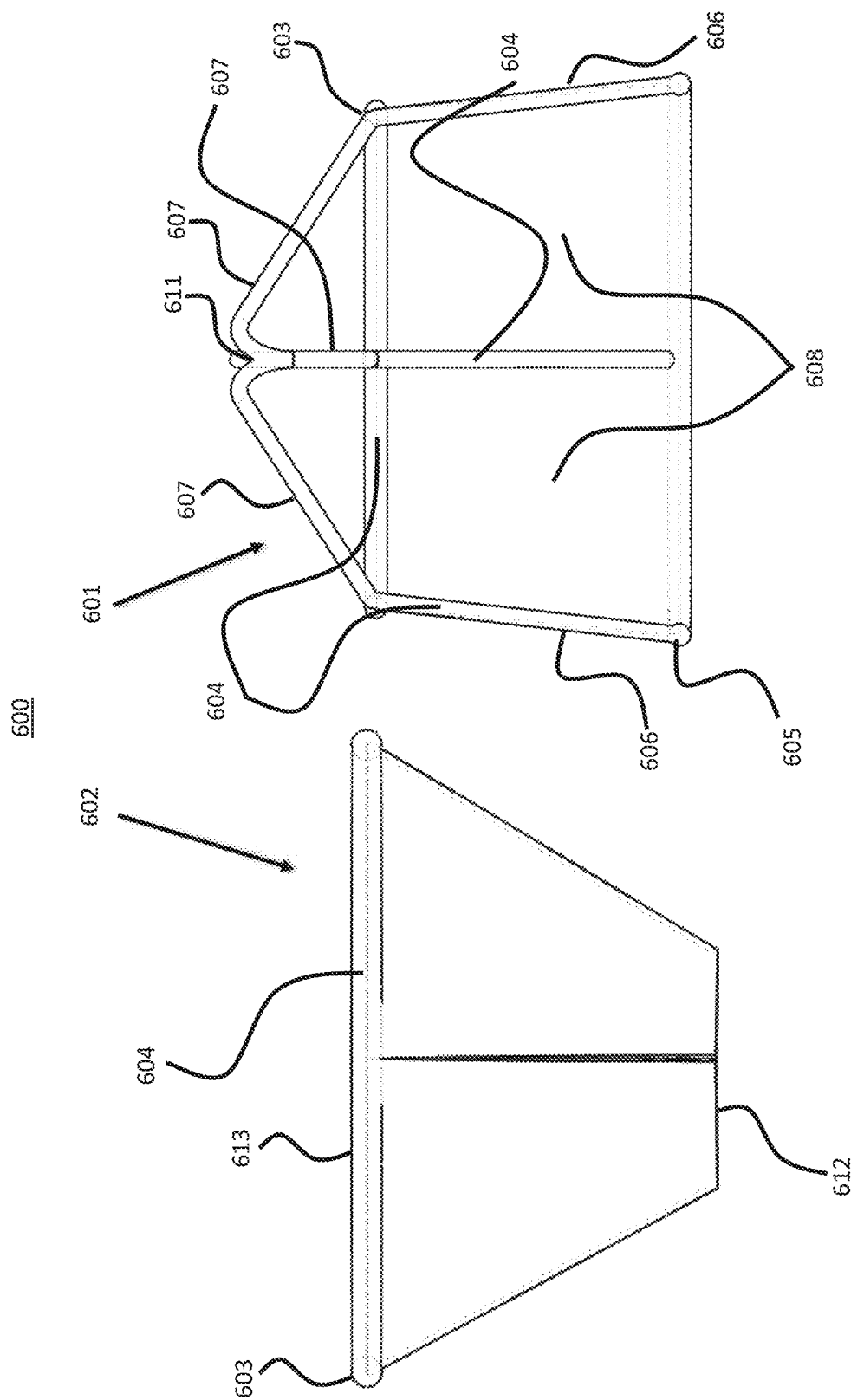
FIG. 34 is a disassembled component side view of a pressure mitigating assembly according to an embodiment of the present disclosure.
Figure 35:
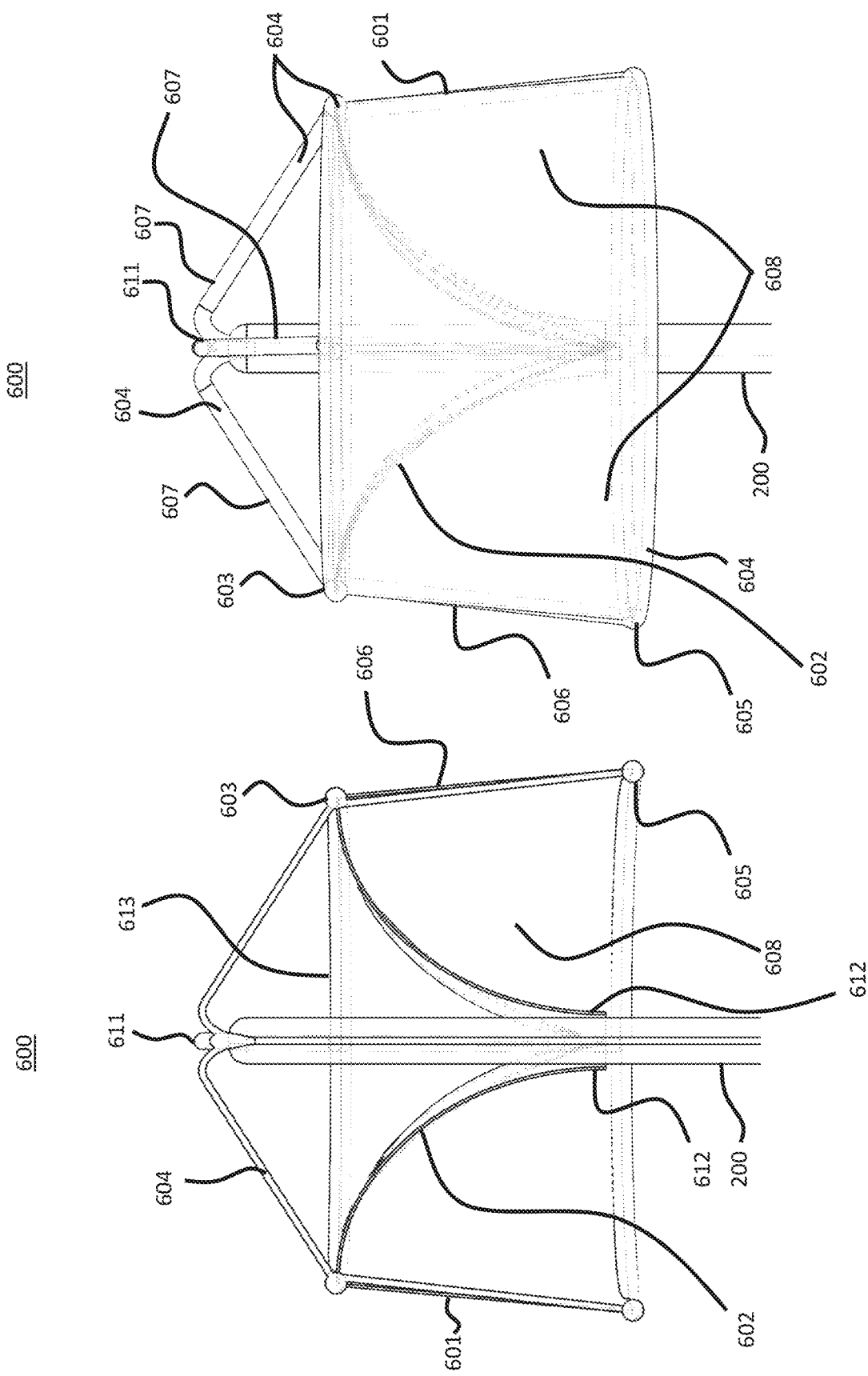
FIG. 35 is a disassembled component cross-section of a pressure mitigating assembly according to an embodiment of the present disclosure.

The pressure mitigating assembly (601) is the structural housing (604) FIGS. 34, 35, consisting of a distal suspension ring (603) and a proximal annular ring (605) resting on or in the proximity of and/or buttressing against the atrial (2) side annular ring (8) of the native or prosthetic valve (7). The distal suspension ring (603) and the proximal annular ring (605), connected by lateral struts or ribs (606), and bridged across the top by flexible cross section struts or crescent shaped struts (607) joining the lateral struts (606) after they connect to the distal suspension ring (603) complete the structural housing (604). This pressure mitigating assembly (601) functions in a multi-functional or multi-purpose role. The structural housing (604), within the pressure mitigating assembly (601), mounts and houses the 'one way valve' or 'check valve' (602) which, in conjunction with the gradient funneling skirt (608), traps, contains, harnesses, seals, and then re-directs the energy and force of the atrioventricular pressure gradient and the regurgitant volume (the representation of the gradient pressure loss). The pressure mitigating assembly (601) is the component that loads, stores, and releases that pressure gradient energy and force enabling mechanical force transduction or transfer of re-purposed native energy and force into the ventricle (3), the septum (6), and the ventricular walls (4). The pressure mitigating assembly (601) being fixed or secured at the fixation point (611), complete with the 'one way valve' or 'check valve' (602) mounted within, to the tether or shaft (200) and then to the apical base plate (300) connected by the multi-lumen tubing (400) to the control unit (500) completes the embodiment (600). Additionally, the pressure mitigating assembly's (601) structural housing (604) components (603)(605)(606)(607)(617) load and store energy and force during the filling diastolic phase, as the ventricle (3) elongates and stretches both in length and width (4) and the nitinol or elastic propertied material the structural housing (604) is composed of is stretched, thus loading the spring with energy and force. The structural housing (604) releases this diastolic loaded energy and force during the ventricular ejection or the systolic phase as the ventricle (3) compresses and contracts, thus releasing the spring like structural housing (604), the length and width rapidly contracting during the process. When this contraction occurs, the structural housing (604), being that the nitinol or elastic propertied material is stretched or loaded (606)(607)(605)(603)(617) at this point, is released and the spring loaded (606)(607)(605)(603)(617) forces loaded are thus released. The distal suspension ring (603), proximal annular ring (605), the lateral struts (606), and the flexing cross sectional struts or crescent shaped struts (607), made of nitinol or any other elastic, expandable, and/or rigidly flexing material, load energy and force during the filling phase, or diastole, as the ventricle (3) expands and lengthens, and then releases this energy and force during the ejection phase, or systole, thus adding ventricular functional support in its assist with the ejection of blood from the ventricle (3) and the mechanical transducting or transferring of these forces via the tether or shaft (200) to the apical base plate (300), and then via this base plate (300) into the ventricle (3), the septum (6), and ventricular walls (4).

The gradient funneling skirt (608) shown in FIGS. 34, 35 traps, captures, seals, steers, and funnels the regurgitant atrioventricular pressure gradient, demonstrated by the hemodynamic volume or regurgitant volume present on the atrial side (2) of the heart valve (7) during systole, into the 'one way valve' or 'check valve' (602) at which point it (the regurgitant volume) is contained and housed within the skirt (608) until such time that this volume is returned back into the ventricle (3) during the filling or diastolic phase. The gradient funneling skirt (608) traps, captures, seals, steers, and funnels the regurgitant volume, visualized by blood, on the atrial (2) side of the native or prosthetic heart valve (7) and represents or demonstrates atrioventricular pressure gradient loss as visualized by regurgitant blood. The atrioventricular pressure gradient energies and forces become a restoring, mechanically delivered, and re-purposed essential requirement for ventricular (3) health and the atrioventricular gradient pressure is critical to maintaining the health of the valve (7), the ventricle (3), the septum (6), and the ventricular walls (4). The gradient funneling skirt (608) is attached and/or fixed to the proximal annular ring (605) on the proximal end of the structural housing (604) and to the distal suspension ring (603) and 'one way valve' or 'check valve' (602) at the opposing or distal end above the 'duck bill' (612) at the distal suspension ring (603). The gradient funneling skirt (608) vectors this regurgitant volume loss into the 'one way valve' or 'check valve' (602) at which point the progress of the regurgitant volume is stopped or halted (612). The structural housing (604) lattice becomes/is the housing, mount, or structural stability and anchor point for the 'one way valve' or 'check valve' (602), as well as the fixation points (603) (605) for the gradient funneling skirt (608). The proximal annular ring (605) holds the one way valve or check valve (602) in place on the annulus (8)

securely on the atrial side (2) of the native or prosthetic heart valve (7). The distal suspension ring (603) is the distal fixation point for the 'one way valve' or 'check valve' (602) with the distal end of the gradient funneling skirt (608) fixated or secured to the distal end of the 'one way valve' or 'check valve' (602). In its dual force capacity, the nitinol and/or elastic, expandable, spring like struts and components of the structural housing (604)(603)(605)(606)(607)(617) still load in diastole and release in systole, thereby providing amplified and/or additional ventricular functional support to ejection as well as force transduction benefits to the ventricle (3), the septum (6), and the ventricular walls (4).

Figure 33:
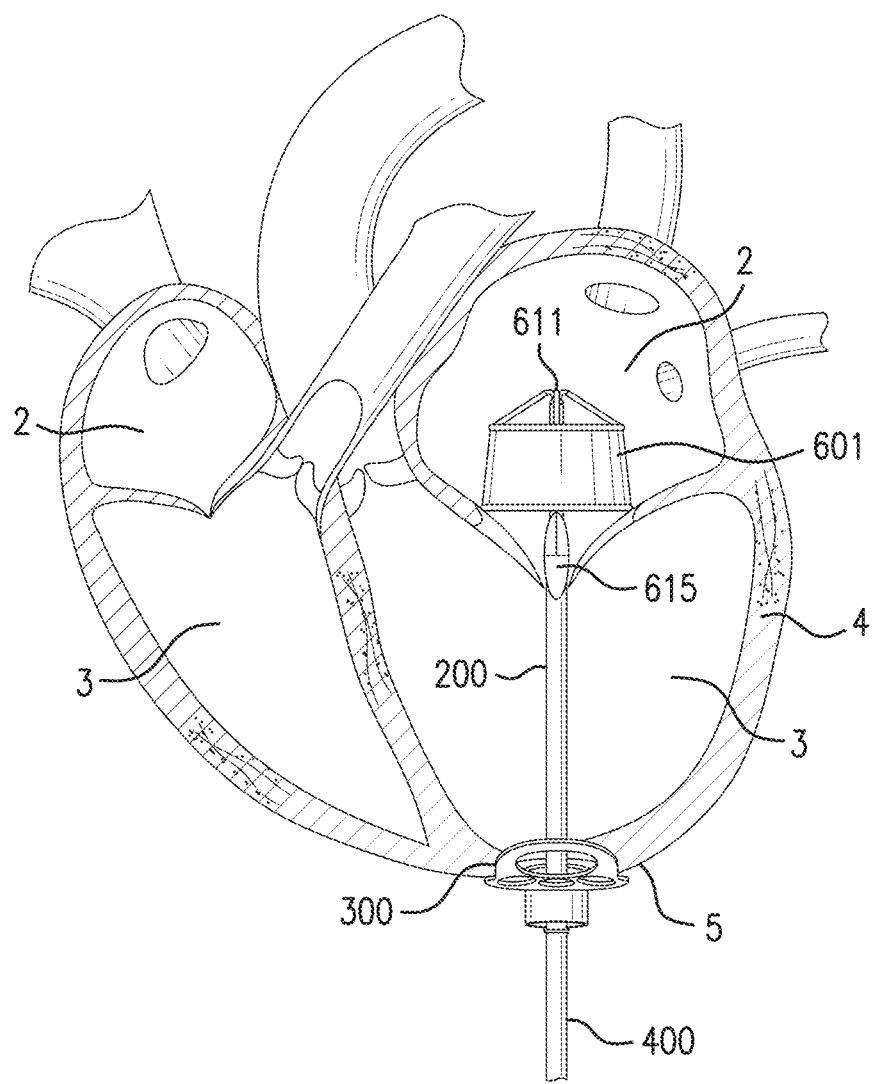
FIG. 33 is a front view of a Dual Force Pressure Mitigating Implant system in situ or as positioned in the human heart according to an embodiment of the present disclosure.
Figure 36:
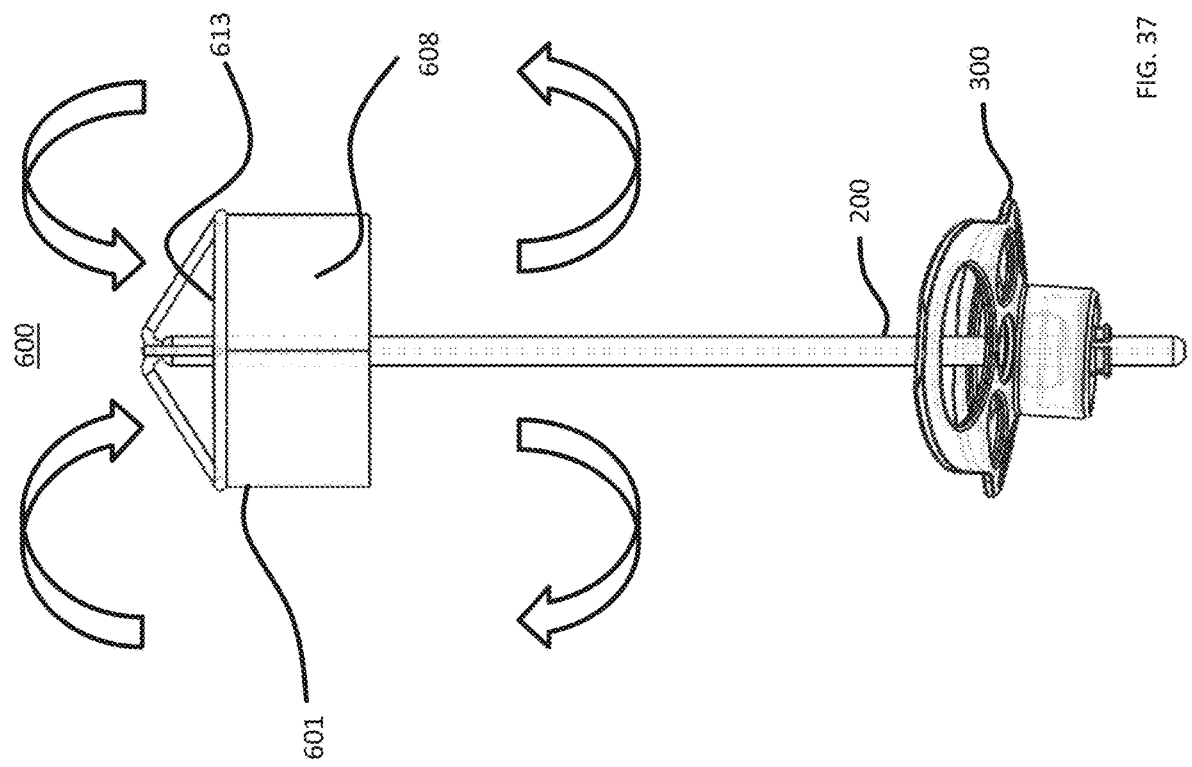
FIG. 36 is a flow illustration depicting a flow direction in systole according to an embodiment of the present disclosure.
Figure 37:
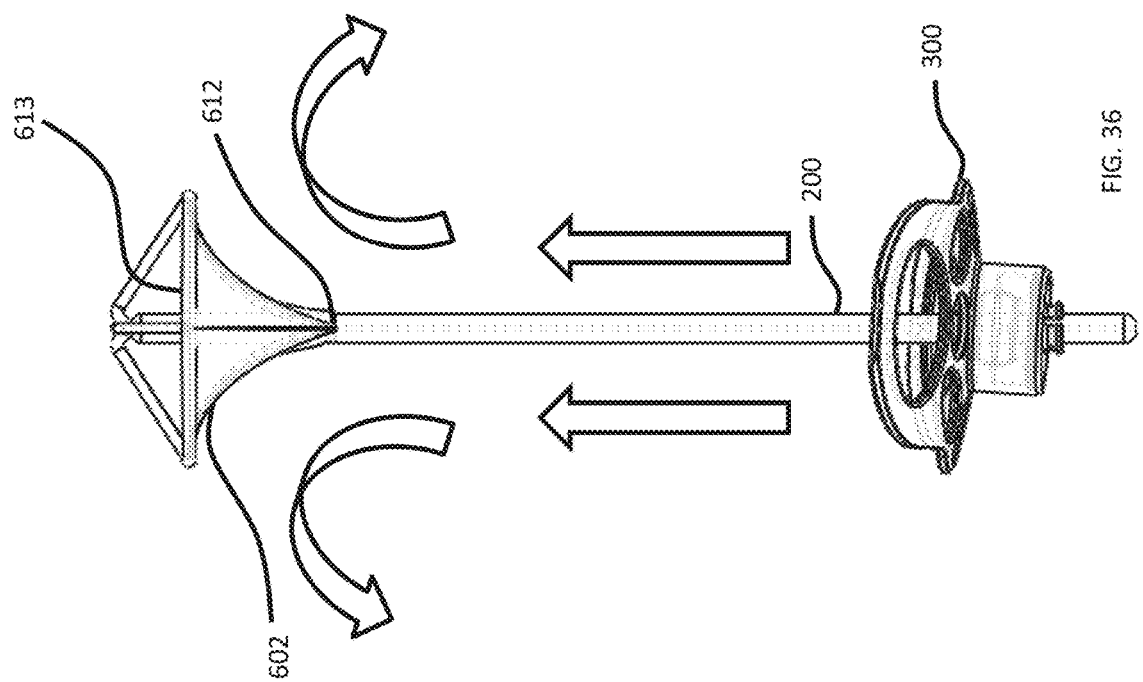
FIG. 37 is a flow illustration depicting a flow direction in diastole according to an embodiment of the present disclosure.
Figure 40:
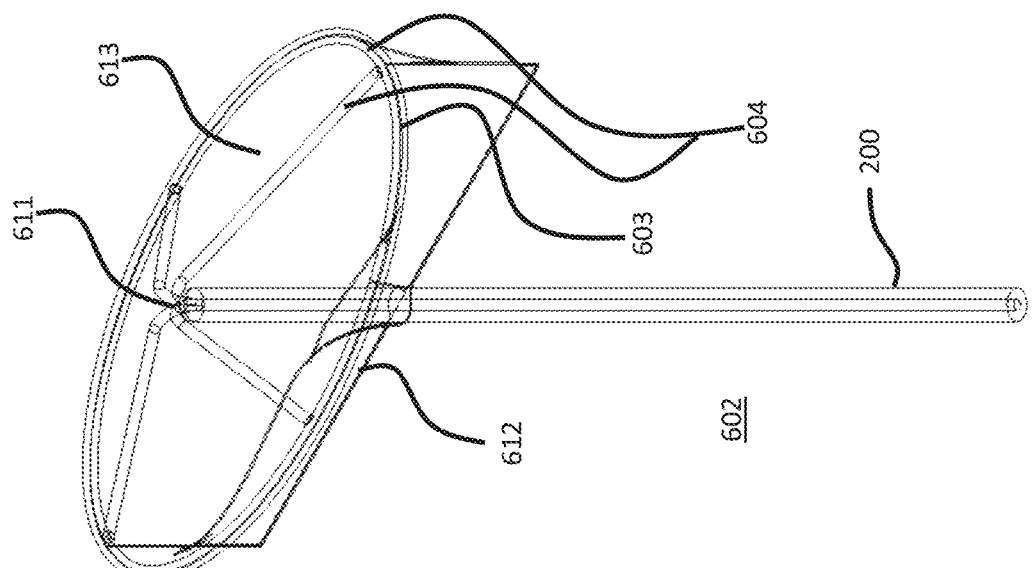
FIG. 40 is a perspective view of a one-way valve or check valve in the closed position according to an embodiment of the present disclosure.
Figure 41:
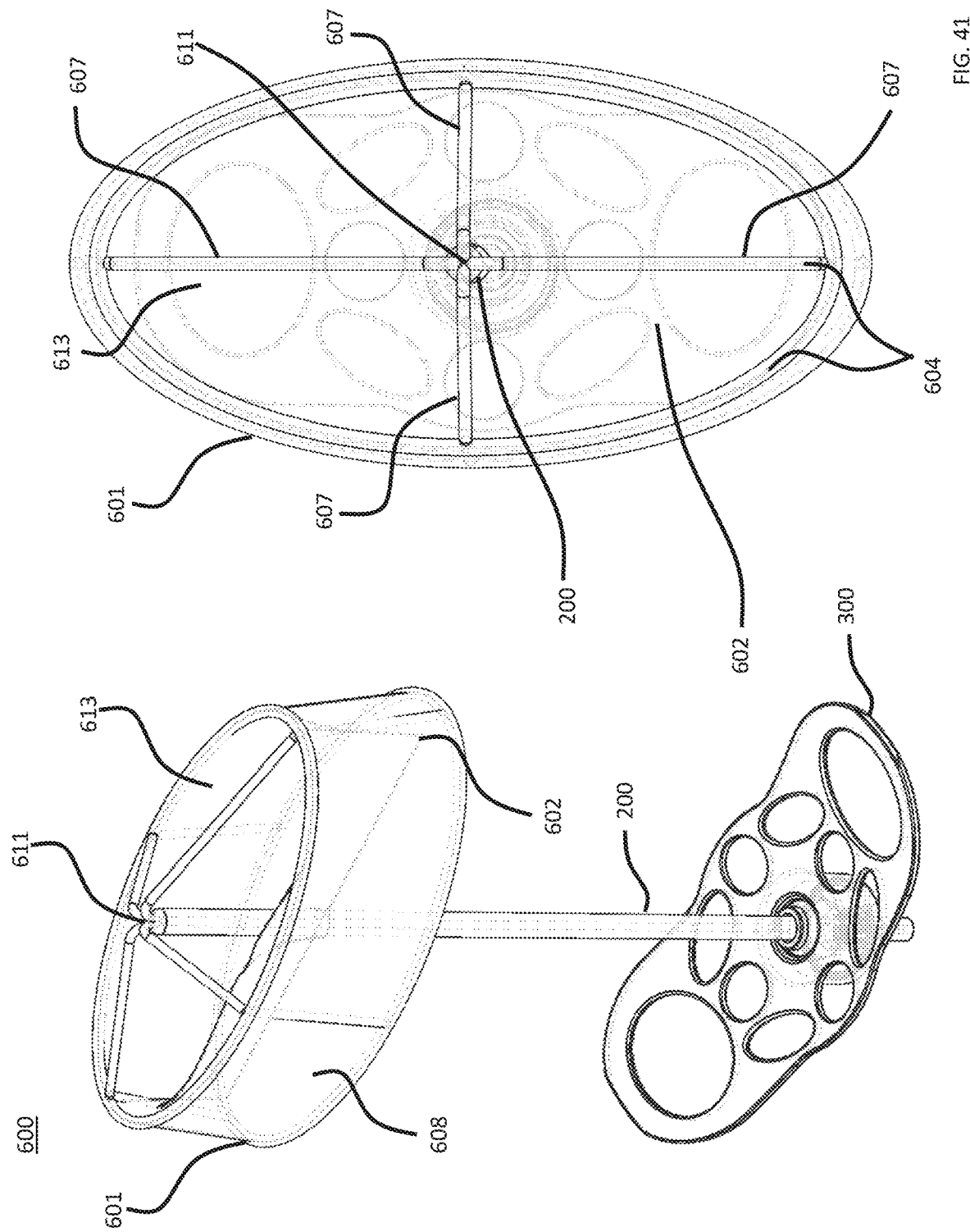
FIG. 41 is a perspective view of a Dual Force Pressure Mitigating Implant with a pressure mitigating assembly one-way valve or check valve in the closed position according to an embodiment of the present disclosure.
Figure 42:
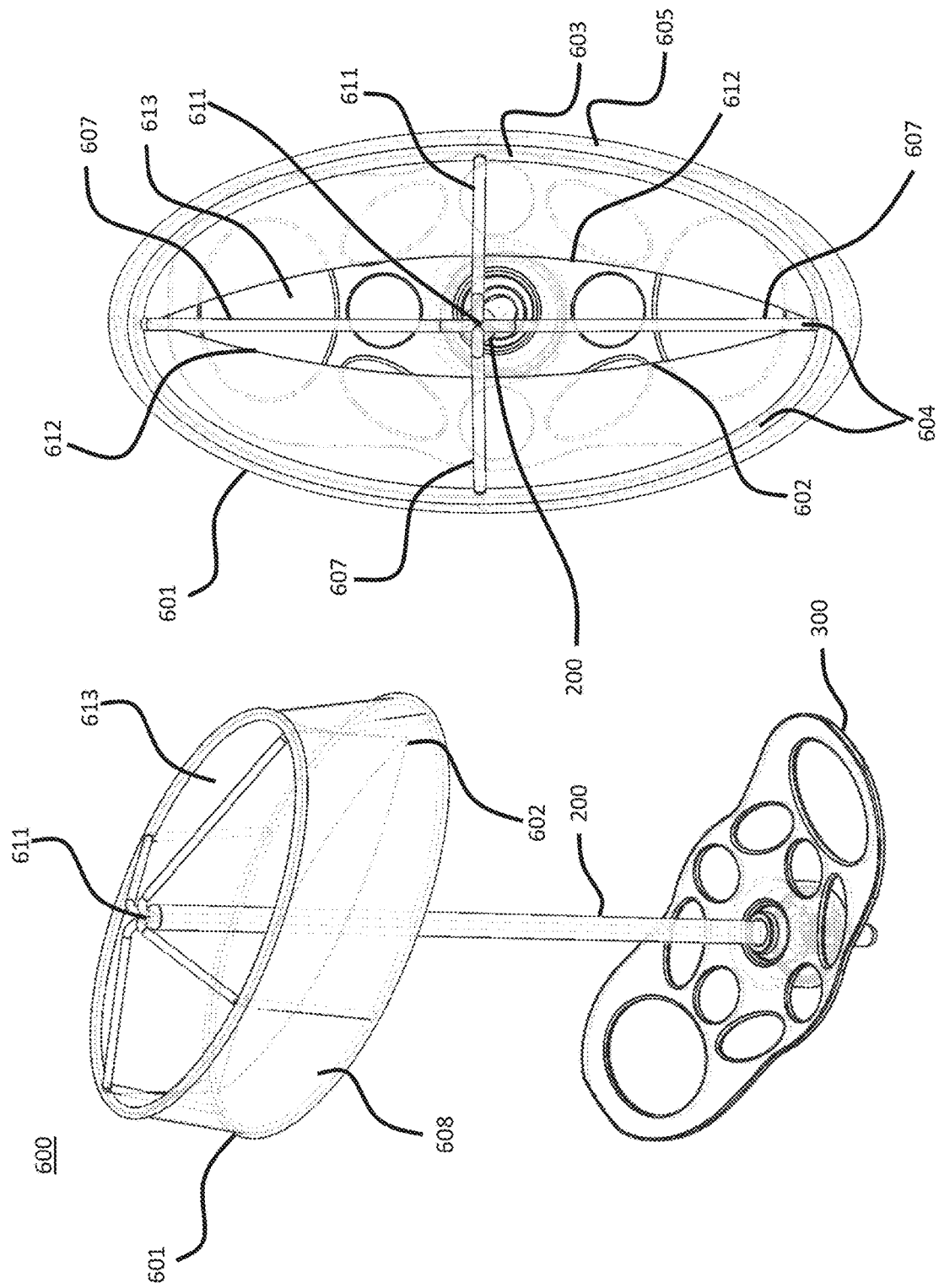
FIG. 42 is a perspective view of a Dual Force Pressure Mitigating Implant with the pressure mitigating assembly one-way valve or check valve in the semi-open position according to an embodiment of the present disclosure.
Figure 43:
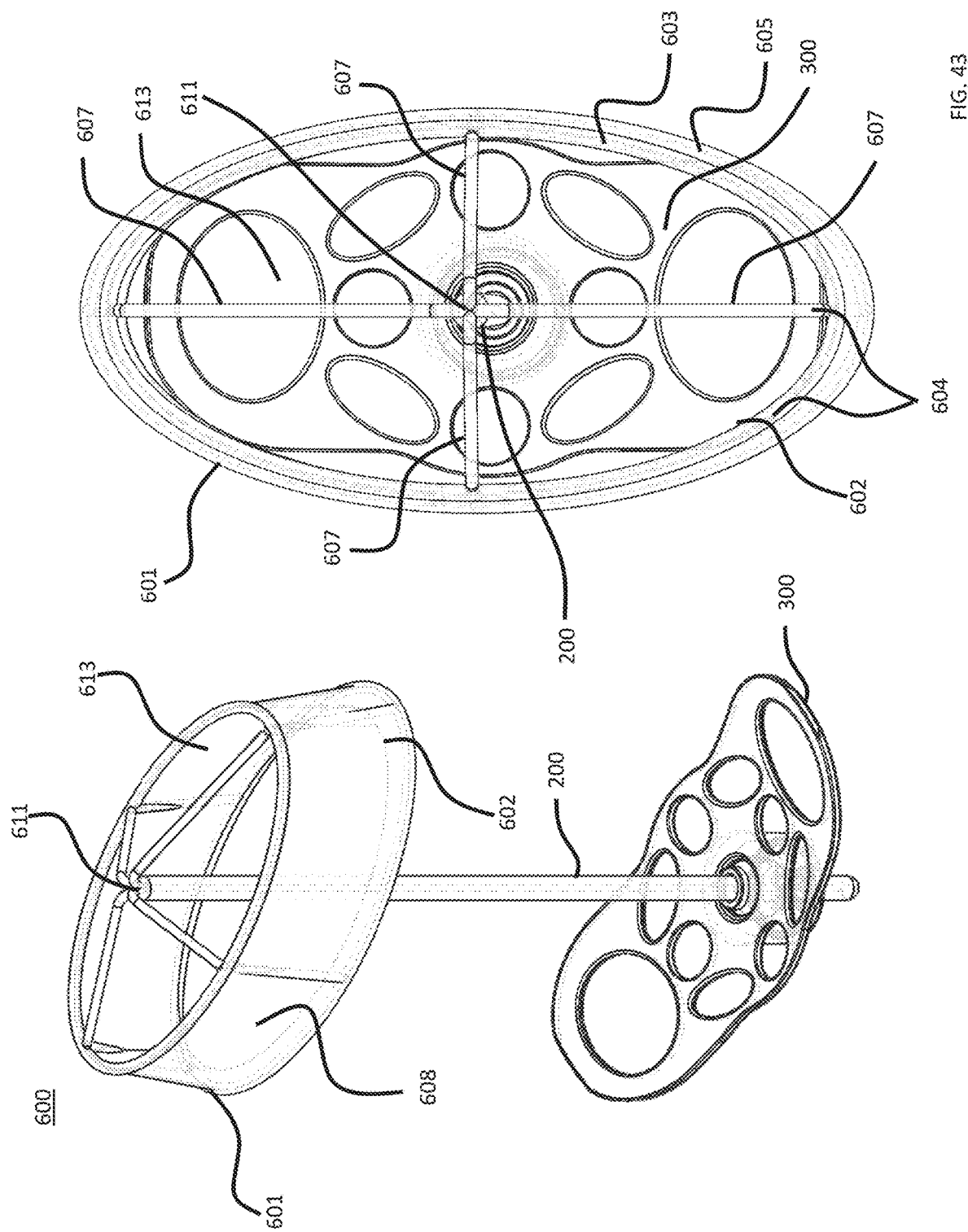
FIG. 43 is a perspective view of a Dual Force Pressure Mitigating Implant with the pressure mitigating assembly one-way valve or check valve in the open position according to an embodiment of the present disclosure.

The 'one way valve' or the 'check valve' (602) traps, stops, seals, halts, and/or impedes the atrioventricular pressure gradient loss as it escapes via the compromised or failing native or prosthetic heart valve (7) during ventricular (3) systole (the pumping or ejection phase). This loss is evidenced by blood volume flowing retrograde and visualized on the atrial (2) side of the native or prosthetic heart valve (7) in the ejection or systolic phase of the hearts cycle shown in FIGS. 35, 36, 41, & 49. The 'one way valve' or 'check valve' (602) allows pressure, blood, and pressure gradient change (atrial high pressure versus ventricular low pressure) to flow or pass through it (602) from the atrium (2), through said 'one way valve' or 'check valve' (602), and FIGS. 37, 38, 43, & 47 into the ventricle (3) but prevents the atrioventricular pressure gradient from leaking or regurgitating back (atrial low pressure versus ventricular high pressure) from ventricle (3) and returning back into the atrium (2) FIGS. 36, 40, & 41. It is the 'duck bill' (612) feature of the 'one way valve' or 'check valve' (602) the open end or distal end (613) oriented toward the atrium (2) and the closed or billed end (612) oriented proximally toward the ventricle (3). This orientation allows flow to pass through the 'check valve' (602) from the atrial/distal (2) (613) side and move through the ventricular oriented/proximal 'duck bill' (612) and into the ventricle (3) FIGS. 37, 38, & 43. In FIG. 40, 41, blood flow and pressure attempting to return from the ventricle (3) back into the atrium (2) is stopped and/or prevented by the closed 'one way' or 'duck bill' valve (612) and contained and stopped or halted within the gradient funneling skirt (608) stopping and trapping (preventing the blood from returning to the atrium (2) from the ventricle (3) within the 'skirt'(608) because it sits and seals directly above the atrioventricular valve (7)) this volume at the closed, one way end, or 'duck bill' (612), of the 'check valve' (602). This positioning, above FIG. 33 the compromised native or prosthetic valve (7), as shown in FIG. 33, traps, stops, seals, and/or impedes the loss of the atrioventricular pressure gradient within the ventricle (3) and prevents regurgitant volume from moving into the atrium (2). The trapped, stopped, and/or impeded systolic regurgitant blood volume that is held proximal (612) to the 'one way valve' or 'check valve' (602) and distal to the compromised native or prosthetic valve (7), returns into the ventricle during the FIG. 37, 38, 43 diastolic phase, which occurs immediately after the systolic phase FIGS. 36, 40, 41. As the 'one way valve' or 'check valve' (602)(612) is positioned and fixed above and on the atrial (2) side of the heart valve (7), the valvular structures (12) (13) and subvalvular apparatus (11) are able to function freely and naturally without any interference from the 'one way valve' or 'check valve' (602) during the hearts cycle of diastole and systole. This repeats continuously throughout each complete heart's cycle.

Figure 39:
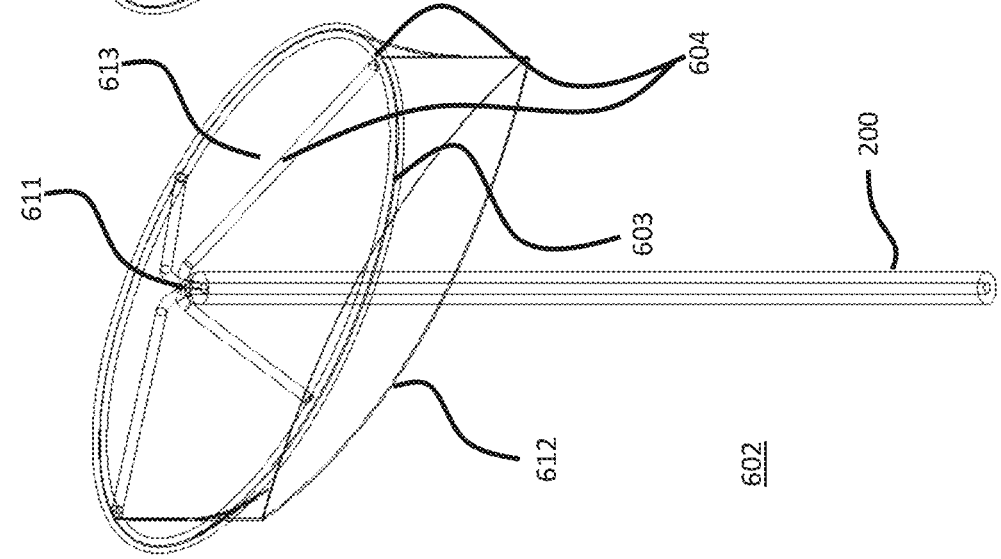
FIG. 39 is a perspective view of a one-way valve or check valve in the semi-open position according to an embodiment of the present disclosure.
Figure 38:
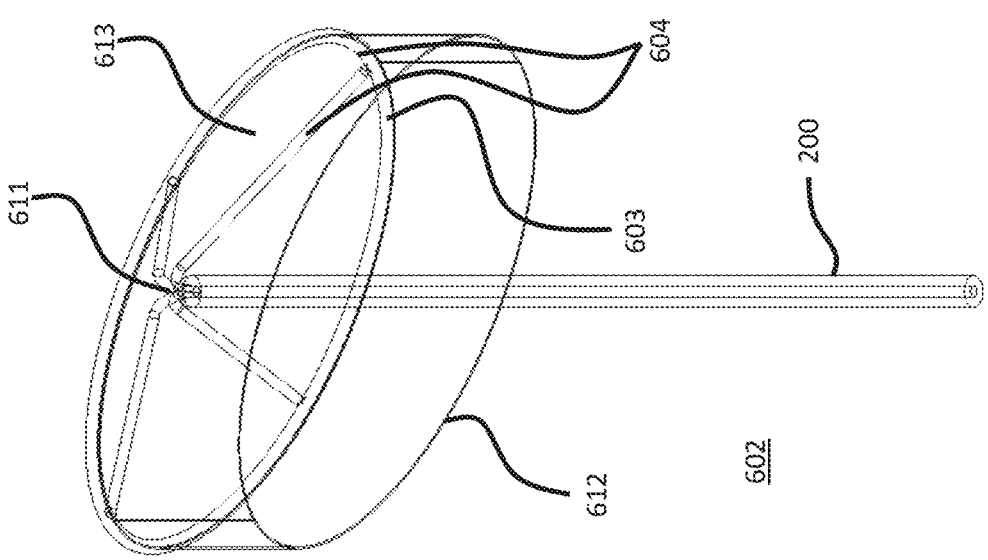
FIG. 38 is a perspective view of a one-way valve or check valve in an open position according to an embodiment of the present disclosure.

The 'one way valve' or 'check valve' (602) is open and rounded FIG. 38 at its distal or top end (613)(603), tapers and flexes FIG. 39 to a proximal end closed 'duck bill' (612) shaped FIG. 40), the distal end (603) being fixed and/or secured to the structural housing (604), distally by the distal suspension ring (603) and laterally by seamed edges of the 'duck bill' (612) tapering up to the distal point of the distal suspension ring (603) of the 'check valve' (602), and conforms (603) to the expansion shape of the nitinol, elastic, expandable, and/or rigid material. The structural housing (604) and the distal suspension ring (603) and the materials they are constructed of, be it nitinol, elastic, and/or expandable material. The 'one way valve' or 'check valve' 602, itself, is constructed of a ePTFE, Dacron, Teflon impregnated Dacron, polyurethane, silicone, polyurethane co-polymer, a laminate of the like and/or any other material, allows the 'one way valve' or 'check valve' (602) to conform to the topography of the atrial annulus (8), via the FIG. 35 proximal suspension ring (605), it is positioned or seated on the annulus (8), in, and/or in proximity to and seals around the atrial side (2) of the annulus (8) and the compromised native or prosthetic valve (7) by way of the gradient funneling 'skirt' (608). The 'one way valve' or 'check valve' (602) secured and fixed to the structural housing (604) and housed inside of the pressure mitigating assembly (601), as one of two component assemblies (602) (601). The two component assemblies (601)(602) combine (200)(300)(400)(500) to become the integrated system distal attachment creating the embodiment called the Dual Force Pressure Mitigating Implant (600).

The structural housing (604), the gradient funneling skirt (608), and the contained 'one way valve' or 'check valve' (602) are components of the pressure mitigating assembly. The pressure mitigating assembly (601) illustrated in FIGS. 34 & 35 is assembled of combined components (604)(608) (611), and is then combined with the 'one way valve' or 'check valve' (602), fixed in positioned above the atrioventricular valve (7) on the and on the atrial side (2) of the heart valve (7). The 'one way valve' or 'check valve' (602) is combined and housed in the pressure mitigating assembly (601), the pressure mitigating assembly (601) then being fixed to the tether or shaft (200), the base plate (300), the multi-lumen tubing (400), and the control unit (500), which is fixed to the apex (5) of the heart by the apical base plate (300), and connected to and in communication with the control unit (500) via the multi-lumen connective tubing (400). This combination becomes the therapeutic device called or referred to as the Dual Force Pressure Mitigating Implant (600). The addition of the second assemblies or components (200)(300)(400)(500) stabilizes and holds in place the pressure mitigating assembly (601) above, in proximity to, and around the annulus (8) of the atrial (2) portion of the hearts valve (7) thus allowing the pressure mitigating assembly to trap, stop, seal, and/or to impede the atrioventricular pressure gradient loss as it escapes via the compromised or failing heart valve during ventricular systole (the pumping or ejection phase). This is all a systematic function and/or one aspect of this integrated device as a system.

The coapting vectoring member (615) may in some embodiments be present on the Dual Force Pressure Mitigating Implant (600). It is a coapting vectoring member (615), inflatable, solid, or semi-rigid, that allows the valvular leaflets (12) (13) and subvalvular apparatus & structures (11) to seal on (615) or 'grab, flex, and pull' on the coapting vectoring member (615). The valvular leaflets (12) (13) and subvalvular apparatus (11) 'grabbing, flexing, and pulling' (10) (9) of the coapting vector member (615) assists, enhances, and/or replaces lost valvulo-ventricular interaction by transducting this native force via the apical base plate (300) which then, by connection via the tether or shaft (200) to and contact with the apex (5), ventricle (3), and ventricular wall (4). Additionally, the coapting vectoring member (615) allows for and facilitates ventricular (3) inflow and outflow vector change. This ability to change or alter inflow and outflow though the valve (7) (12) (13) vector may enhance, facilitate, and/or restore vortex formation restoring vortical flow in the intracardiac space. This is all one systematic function and/or one aspect of this integrated device as a system.

Dual Force Pressure Coapting Implant—Another embodiment, described in connection with FIG. 45-46, is substantially identical to the system (600) described hereinabove, with the substantial differences noted herein. The Dual Force Pressure Coapting Implant (619) is described as another device within an integrated system. According to this embodiment, the Dual Force Pressure Coapting Implant (619) consists of a therapeutic fixation assembly (614) and a 'one way valve' or 'check valve' (602). The therapeutic fixation assembly (614) being distally attached or fixed (611) to the assembly known as the shaft or tether (200), connected or fixed to the base plate (300), and connected to the control unit (500) via the multi-lumen tubing (400), which when combined, are collectively known as the Dual Force Pressure Coapting Implant (619). The therapeutic fixation assembly (614) has a structural housing (604) consisting of a proximal annular ring (605) intended to rest on or near, be seated on or near, or be seated in or near the valve annulus (8), a distal suspension ring (603) framing the open distal filling end (613) top (614) and serving as the distal fixation point for the gradient funneling skirt (608) with the proximal end of the gradient funneling skirt (608) fixated by the proximal annular ring (605), and structural components such as the lateral struts (606) and the support beams (617) which structure the housing (614). An intravalvular 'check valve, 'one-way valve', or 'duck bill' (602)(612) resting along a line of coaptation (112), within the native valve (7), between the anterior (12) and posterior leaflets (13) as they seal or coapt in systole is fixed to the expanding proximal annular ring (605) which will splay out within the atrium (2) or atrially (2) above the native valve (7) around the annulus (8). The gradient funneling skirt (608), fixed to the distal suspension ring (603), acts as a flow funneling or flow directing sealing barrier allowing blood to freely flow from the atrium (2) through the one way valve or 'duck bill' (602) and into the ventricle (3), while remaining and being fixed (611) or attached to the therapeutic fixation assembly (614), during diastole or the filling phase of the cardiac cycle.

The expanding distal suspension ring (603) will be in connection with the proximal annular ring (605) via fixation to or with the lateral struts (606) and the gradient funneling skirt (608). The gradient funneling skirt (608), located on the inflow side, between the distal suspension ring (603) and the proximal annular ring (605) in this embodiment, directs and vectors flow, FIGS. 47, 48, 49 from the atrium (2) into the ventricle (3), into and through the intravalvular 'one-way valve or 'duck bill' (602). The intravalvular 'one-way valve' or 'check valve' (602) or 'duck bill' (612) valve housing is attached or fixed onto the proximal annular ring (605) and then its proximal end protrudes in between the anterior (12) and posterior (13) valve leaflets (12)(13) within the valve (7) structure itself where it remains fixed. By being in close proximity to the intravalvular check valve' or one way valve (602) fixated to the proximal annular ring (605), blood is allowed to flow from the inflow atrial (2) side to the outflow ventricular (3) side but not in the FIG. 49 reverse meaning ventricular (3) to atrial (2). The intravalvular 'check valve' (602) or intravalvular 'one way valve' (602) has leaflets or appendages (narrowing into 'duck bill shape' (612) creating a backflow resistant proximal end (612)); features that are designed and/or intended to steer, guide, direct and or vector hemodynamic flow during diastole and to seal off the ventricle (3) from the atrium (2) during ventricular systole. The device is held in position with lateral struts (606) connected to support beams (617) or connecting struts that connect or are fixed to the proximal annular ring (605) and then to the therapeutic fixation assembly (614) at the fixation point (611) at the end of the tether or shaft (200). The therapeutic fixation assembly (614) is part of the integrated system that includes the tether or shaft (200), the apical base plate assembly (300), and the control unit (500). This is all one systematic function and/or one aspect of this integrated device as a system.

Figure 52:
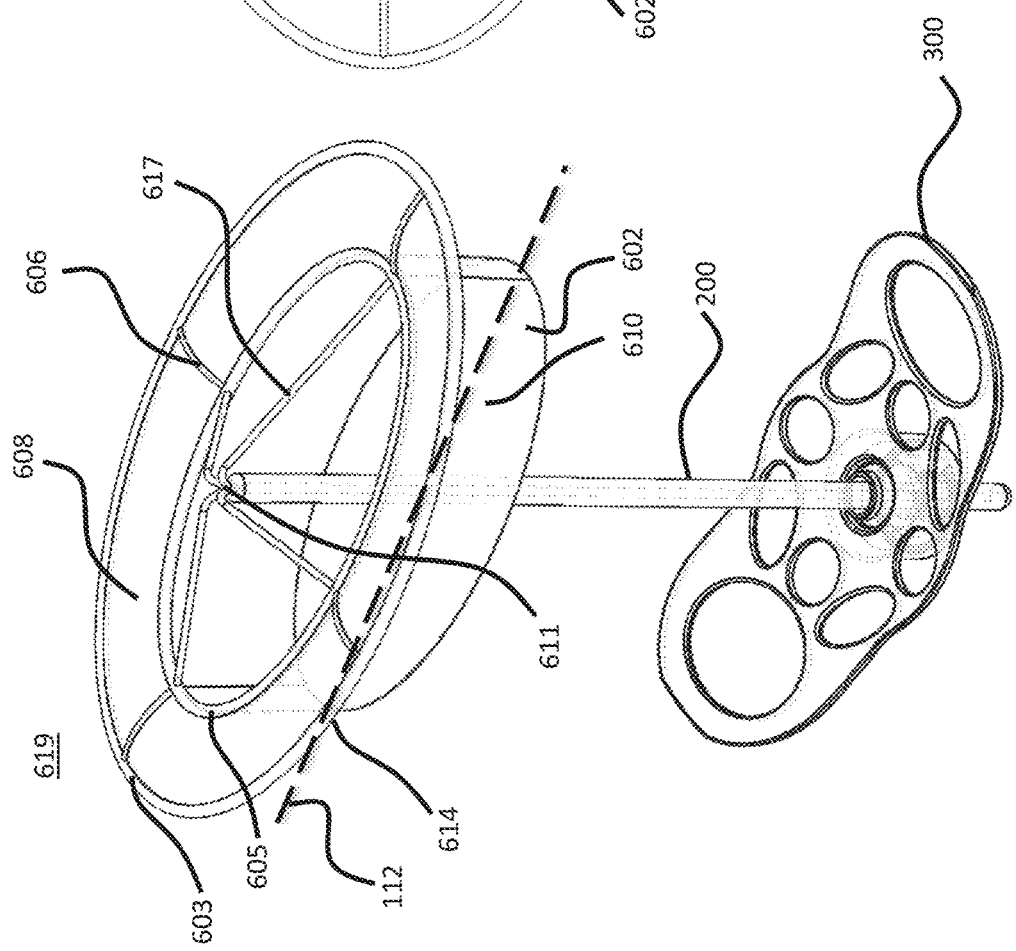
FIG. 52 is a perspective view of a one-way valve in the open position according to an embodiment of the present disclosure.
Figure 55:
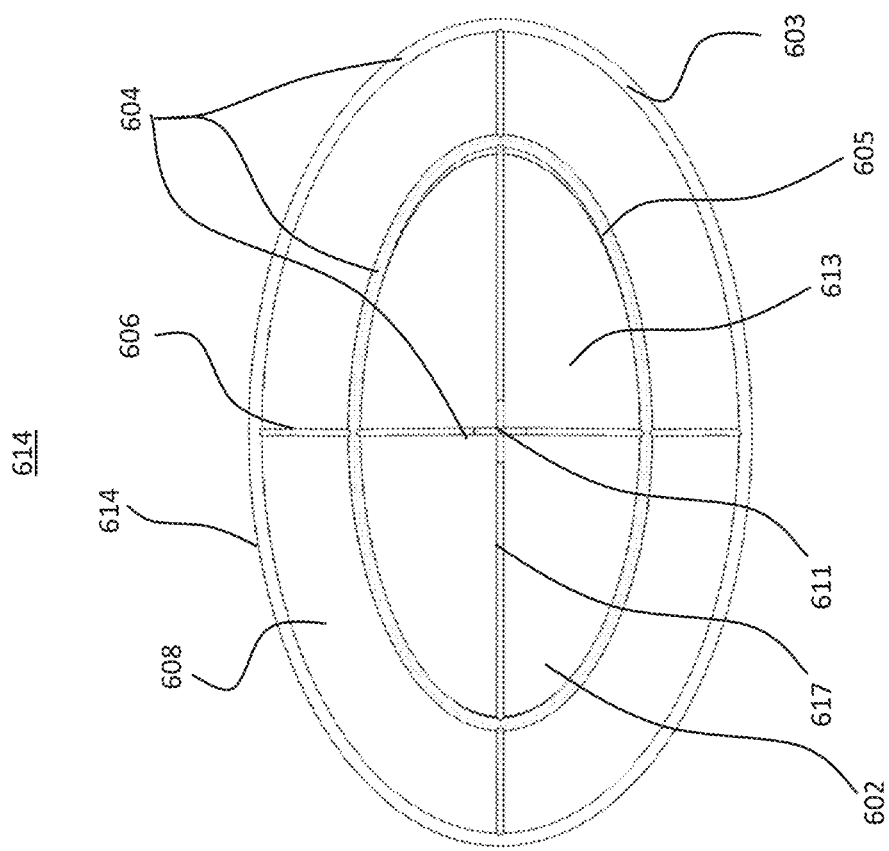
FIG. 55 is a top view of a Therapeutic Fixation Assembly according to an embodiment of the present disclosure.
Figure 54:
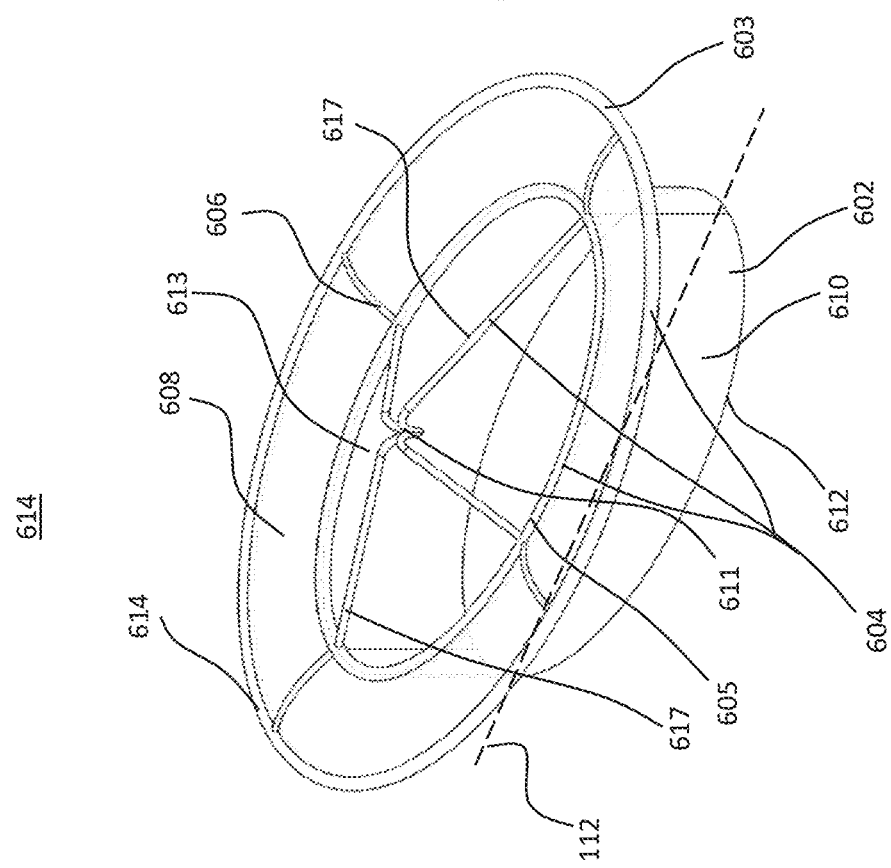
FIG. 54 is a perspective view of a Therapeutic Fixation Assembly according to an embodiment of the present disclosure.

The therapeutic fixation assembly (614) (as shown in FIGS. 51, 53-55) consists of two components: the structural housing (604), combining the structural components (603) (605)(606)(617) and the gradient funneling skirt (608). The 'one-way valve' or 'check valve' (602) with a 'duck bill' (612) is then mounted or housed in the therapeutic fixation assembly (614). The structural housing (604) frame includes the distal suspension ring (603), the lateral struts (606), support beams (617) and the proximal annular ring (605). The one-way valve or 'check valve' valve (602) is connected to the proximal annular ring (605) and functions to permit or allow flow in one direction by the 'duck bill' backflow resistant end (612). The gradient funneling skirt (608) is the component fixated between the distal suspension ring (603) and the proximal annular ring (605). The gradient funneling skirt (608) functions as a flow funneling and regurgitant-sealing component for the vectoring one-way valve or 'duck bill' (602). The gradient funneling skirt (608) is held in proximity to the atrial endocardium by the distal suspension ring (603) and/or the proximal annular ring (605). The support beams (617) extend from the central tether or shaft (200) to the lateral struts (606) which are both fixated to the proximal annular ring (605). The distal suspension ring (603) is fixated to the lateral struts (606) and the lateral struts (606) are fixated to the proximal annular ring (605). The support beams (617) and the lateral struts (606), being attached or fixated to the distal suspension ring (603) and the proximal annular ring (605), provide form and shape as the structure self-expands and/or contracts and FIG. 52 enables (610) force transduction, meaning the capture, harnessing, redirection, and release, of the energy and force of the systolic pressure gradient as the native valve's leaflets (12)(13) act to 'grab, flex, and pull or act on the surface area of the 'one way valve' or 'check valve'(602). The energy and force is then delivered via the structural housing (604) to the shaft (200) to the base plate (300) and into the impaired ventricular structures (4)(5)(6)(9)(10) and within the ventricle (3) captured as the one way valve or 'duck bill' (602) is seals in systole. The energy and force of the atrioventricular pressure gradient within the ventricle (3), the native force that closes the valve (7) leaflets around the tether or shaft (200) and seals closed the 'one-way valve' or 'check valve' (602) is then mechanically delivered via the therapeutic fixation assembly (614) and the 'one way valve' or 'check valve' (602) into the ventricle (3), the septum (6), and the ventricular walls (4).

The Dual Force Pressure Coapting Implant (619), is described hereinabove. This assembly consists of the therapeutic fixation assembly (614) containing the one-way valve or check valve (602), a tether or shaft (200), a base plate assembly (300), which may be ball jointed (301) or piston adjusting (308), a multi-lumen connective tubing (400), and a control unit (500) in communication with the distal device attached to the tether or shaft (200).

Figure 44:
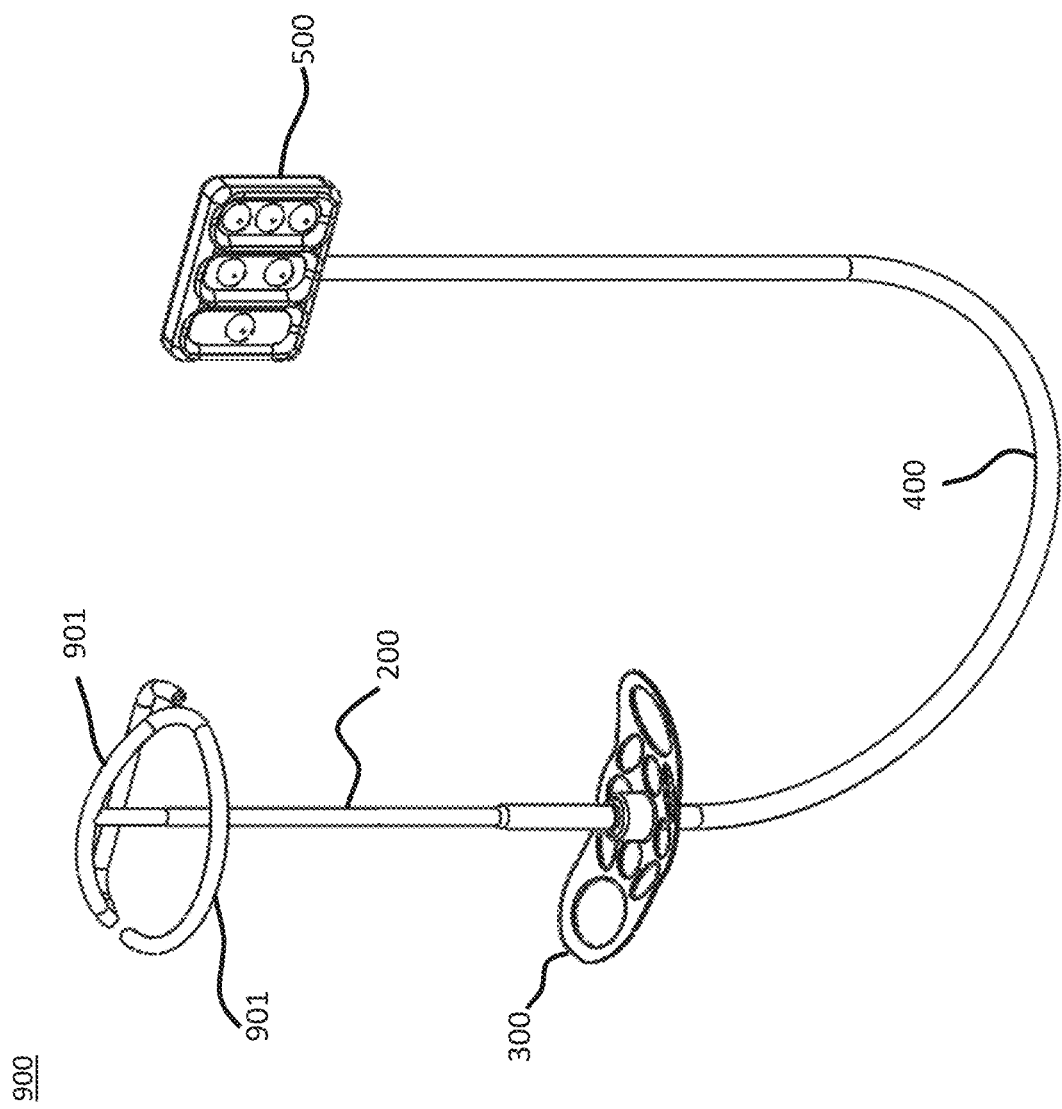
FIG. 44 is a front view of a Dual Force Annular Implant with the dual force implant as a separate distal shaft component of an integrated system according to an embodiment of the present disclosure.
Figure 53:
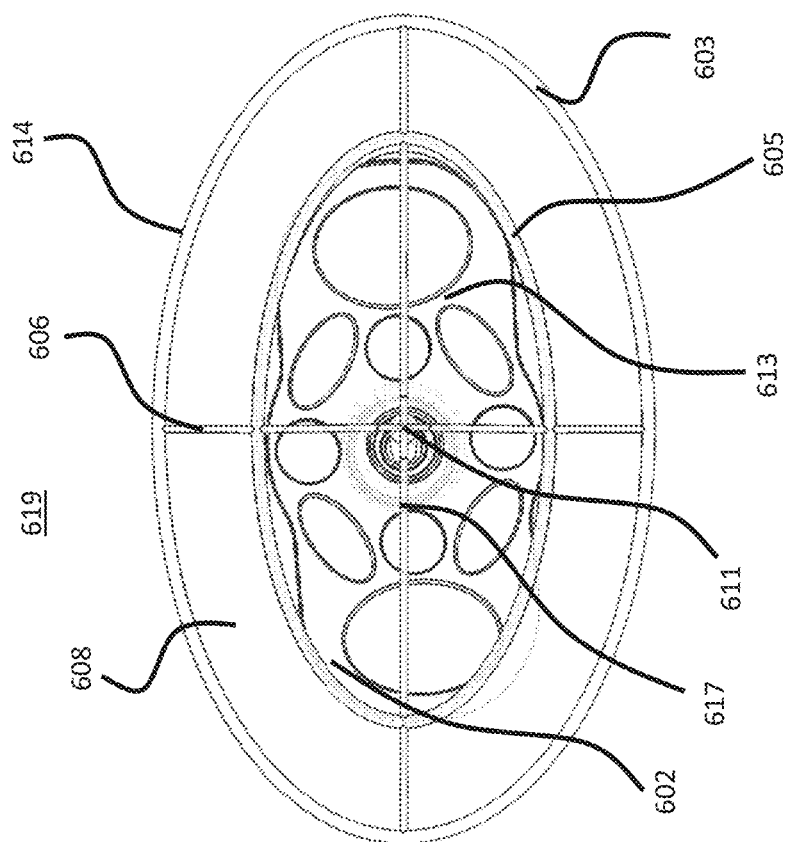
FIG. 53 is a top view of a one-way valve in the open position according to an embodiment of the present disclosure.

The Dual Force Annular Implant, (900), another embodiment of the device as shown in FIG. 44, is substantially identical to the system (600)(619)(100) described hereinabove, with the substantial differences noted herein. The dual force annular halo (901), is made of Nitinol, or elastic spring-like, memory based material and is self-expanding around the annulus (8) on the atrial (2) side of the atrioventricular valve (7). The dual force annular halo (901) is fixed to the shaft (200) or tether, which is fixed to the base plate (300), which is connected via multi-lumen tubing (400) to the control unit (500). By fixing the dual force annular halo (901) on the atrial (2) side of the atrioventricular valve (7), the valve plane (8)(7) is mechanically connected to the apex (5) of the heart (1) and thus, the shaft making the connection, becomes, in effect, an additional or third papillary muscle (9)(10)(11) delivering targeted maximum energy and force of the atrioventricular pressure gradient via mechanical force transduction (meaning the capture, harnessing, collection, and transfer of existing native energy and force) into the ventricular structures (4)(5)(6), the ventricle (3), the apex (5), and the septal wall (6). The dual force annular halo (901) loads energy and force in diastole, as the ventricle (3) stretches, fills, and prepares for contraction, and releases during the systolic cycle dramatically assisting in ventricular ejection. The dual force mechanics, spring loading energy and force in one cycle and releasing it in an contractile release in another, as is seen in the Dual Force Annular Implant (900) is mechanically replicated within the Dual Force Pressure Mitigating Implant (600) and the Dual Force Pressure Coapting Implant (619) (as shown in FIGS. 30, 31, 45 & 46) in two forms or ways. First, the mechanical connection between the valvular plane (8)(7) and the apex (5) via a distal attachment (600)(601)(619)(614)(200)(300) from the valve plane to the apex is mechanically created. The pressure mitigating assembly (601), as part of the Dual Force Pressure Mitigating Implant (600), assists the ventricle (3) by connecting the valve plane (7)(8) with the apex (5) via the shaft (200) thus functioning as an artificial or mechanical papillary muscle (9)(10)(11) and captures the atrioventricular pressure gradient energy and force, while simultaneously mitigating the atrioventricular pressure gradient loss, and then loading this energy and force into the nitinol or spring-like structural housing (604)(603)(605)(606)(617) during one phase (diastole) and subsequently releasing this force in the next phase (systole), a contractile release, in the next phase acting as an added ventricular assist. This function thereby utilizes the native pressure differential between the ventricle (3) and the atrium (2) found naturally within the ventricle during the hearts cycle as a therapeutic modality. The connection of the valvular plane (8)(7) to the apex (5), assisting the ventricle (3) is accomplished via the device (619)(600) via a proximal annular ring (605) joined or resting on or in proximity to the heart valve annulus (8), either prosthetic or native, which is connected (611) or linked to the shaft or tether (200) by lateral struts (606) or support beams (617) and the tether/shaft (200) which is held in place by the base plate (300). Secondly, the tether and or shaft (200) fixated (611) in combination with the lateral struts (606) and the support beams (617) deliver to and are the connection and communication between the proximal annular ring (605) and the base plate (300) and they function to reconnect and link the valvular plane (8)(7) to the apex (5) to the ventricle (3) to capture, harness, restore, and transduct or transfer the native forces of physiologic intracardiac flow and the cardiac cycle, the atrioventricular pressure gradient to the structures of the ventricle (3)(4)(5)(6) that the chordae tendineae (9) and papillary muscles (10) normally deliver in a healthy unaffected human heart. This mechanical connection restores this capacity of the injured heart, which, due to the insult or pathology, can no longer deliver or delivers it in a reduced or diminished capacity, and/or delivers a dysfunctional and ineffective valvulo-ventricular interaction with the ventricular structures (4)(5)(6) and ventricular walls (4). An additional function is transducting, or transferring and delivering the atrioventricular pressure gradient energy and force captured (610) by the 'one way valve' or 'check valve' (602) with the gradient funneling skirt (608) via the coapting intravalvular surface (610) along the line of coaptation (112) of the therapeutic fixation assembly (614) atrial fixation of the pressure mitigating assembly (601). The pressure gradient is captured across the area of the 'one-way valve' or 'check valve' (602) and gradient funneling skirt (608) and the resulting force is then transducted into the structural housing (604) and through the tether/shaft (200) to the base plate (300) on the apex (5). This action mechanically transducts or transfers the energy and force that an incompetent valve (7), meaning a valve (7) losing the atrioventricular pressure gradient, to the structures the impaired ventricle (3) and heart (1) would not be able to support and maintain without assistance. Through the mechanical connection from the valvular plane (8) (7) to apex (5) and thereby the ventricle (3), the connection coupled with the energy and force captured by the 'one way valve' or 'check valve' (602) and pressure mitigating assembly (601) or the therapeutic fixation assembly (614) the embodiments (600)(619) (900) functions to rehabilitate the ventricle (3) and its structures (4)(5)(6)(11) and, by proxy, the heart (1).

Figure 21:
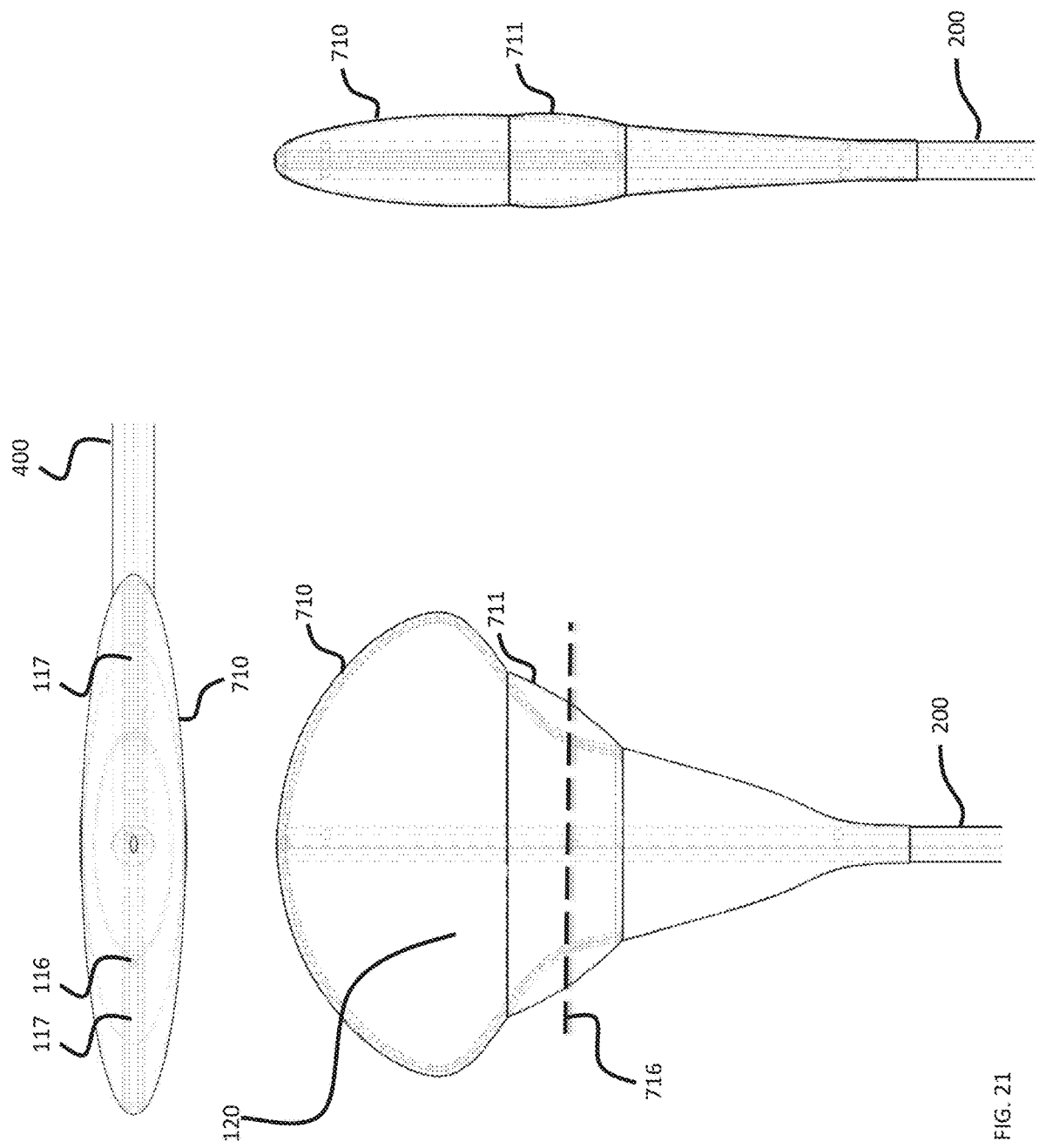
FIG. 21 illustrate side view, perspective view, and a top down views of a member according to an embodiment of the present disclosure.
Figure 26:
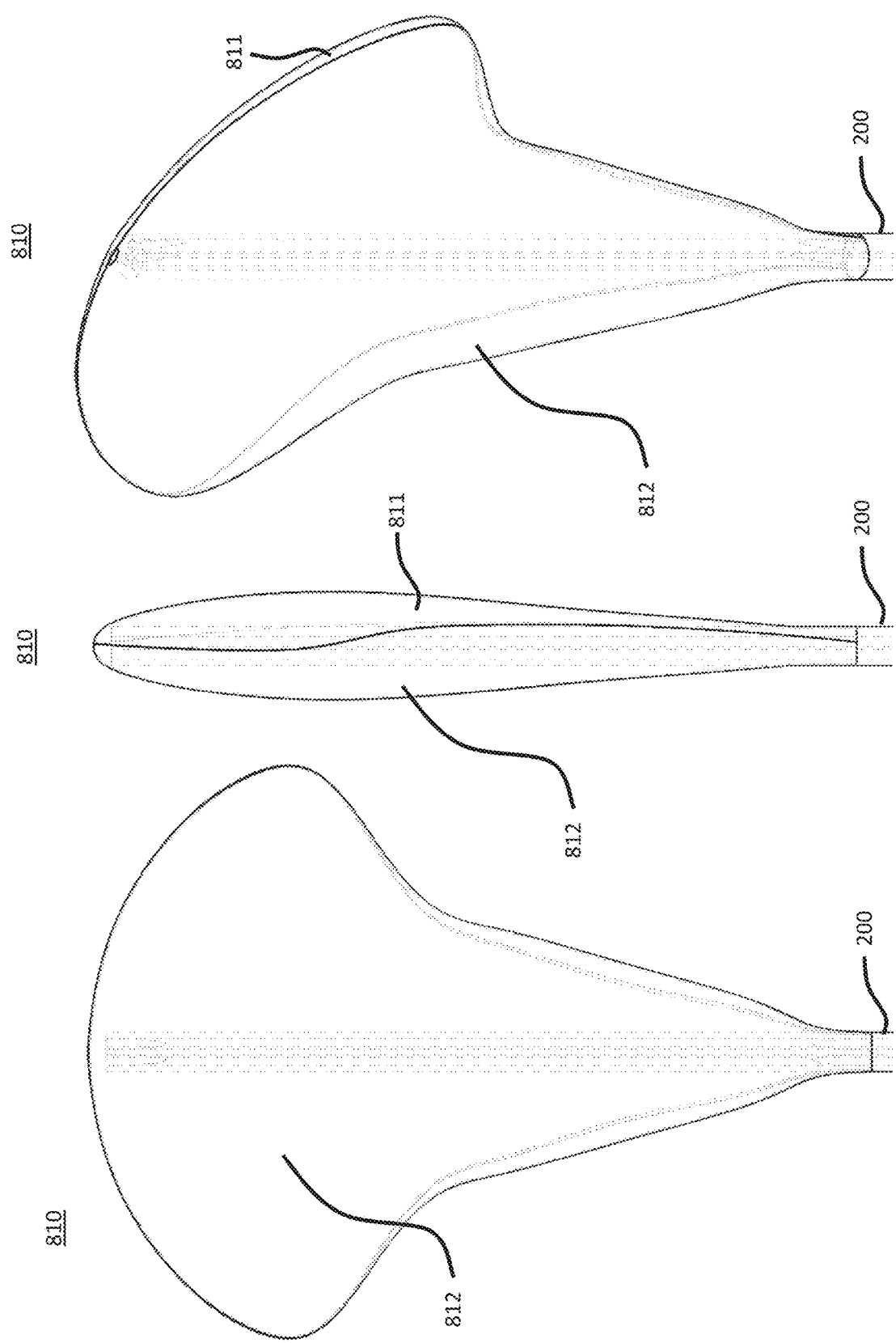
FIG. 26 illustrates front, side, and perspective exterior views of a semi-lunar rigid inflatable member according to an embodiment of the present disclosure.

Each of the above described embodiments reflects an integrated system including a distal member or attachment (110)(710)(810)(601)(614)(901) having a universal tether or shaft (200), a universal base plate (300), the universal connective tubing (400), and the universal control unit (500). The interchangeable 'members' (110)(710)(810)(901) (as shown in FIGS. 10, 21, & 26), the Dual Force Annular Band (900)(901) (as shown in FIG. 44), the pressure mitigating assembly (601) (as shown in FIGS. 34 & 35), the therapeutic fixation assembly (614) (as shown in FIGS. 51, 53, 54, 55), the Dual Force Pressure Mitigating Implant (600) (as shown in FIGS. 30 & 31), and the Dual Force Pressure Coapting Implant (619) (as shown in FIGS. 45 & 46) in all embodiments, are interchangeable distal assemblies with the universal components (200)(300)(400)(500). Those universal components include the universal tether or shaft (200), the universal base plate (300), the universal connective tubing (400), and the universal control unit (500). All of these components (110)(710)(810)(601)(901) combine in combination with a distal tether or shaft component (200) as one integrated system to treat vortical flow FIG. 1 (110)(710)(810)(619), shape (110)(710)(810)(601)(614)(901), and pressure (110)(710)(810)(601)(614) dysfunction in either ventricle (4) of the human heart as a primary therapy or as an adjunct therapy with or without either native or prosthetic atrioventricular valves (7) and/or other prosthetic devices. All of the components, parts, and sub-systems mentioned are a part of this device as an integrated system.

In various embodiments, an integrated implant system may be surgically implanted via transcatheter delivery in the human heart (1)(2)(3) in a transapical manner, via a left side thoracotomy (1218) with a transapical access (5). In various embodiments, the implant system may be implanted in a minimally invasive procedure as described in more detail below. With the apical base plate assembly (300) replaced by the universal splayhook anchor plate (1101), each of the above described embodiments (100)(600)(619)(700)(800)(900) may also be implanted in a true transcatheter manner. This transcatheter method of implant is less invasive and more easily tolerated by patients. The apical base plate assembly (300)(301)(302) is replaced with a universal splayhook anchor plate (1101) that is delivered via a procedural steerable sheath (1200). The universal splayhook anchor plate (1101) is pre-assembled and pre-connected into the proximal end (1105) of the integrated systems shaft (200)(1105) at the central universal ball mount (1103) with the male universal ball connector (1113) coupled inside the shaft (200)(1105).

Figures 58A, 58B:
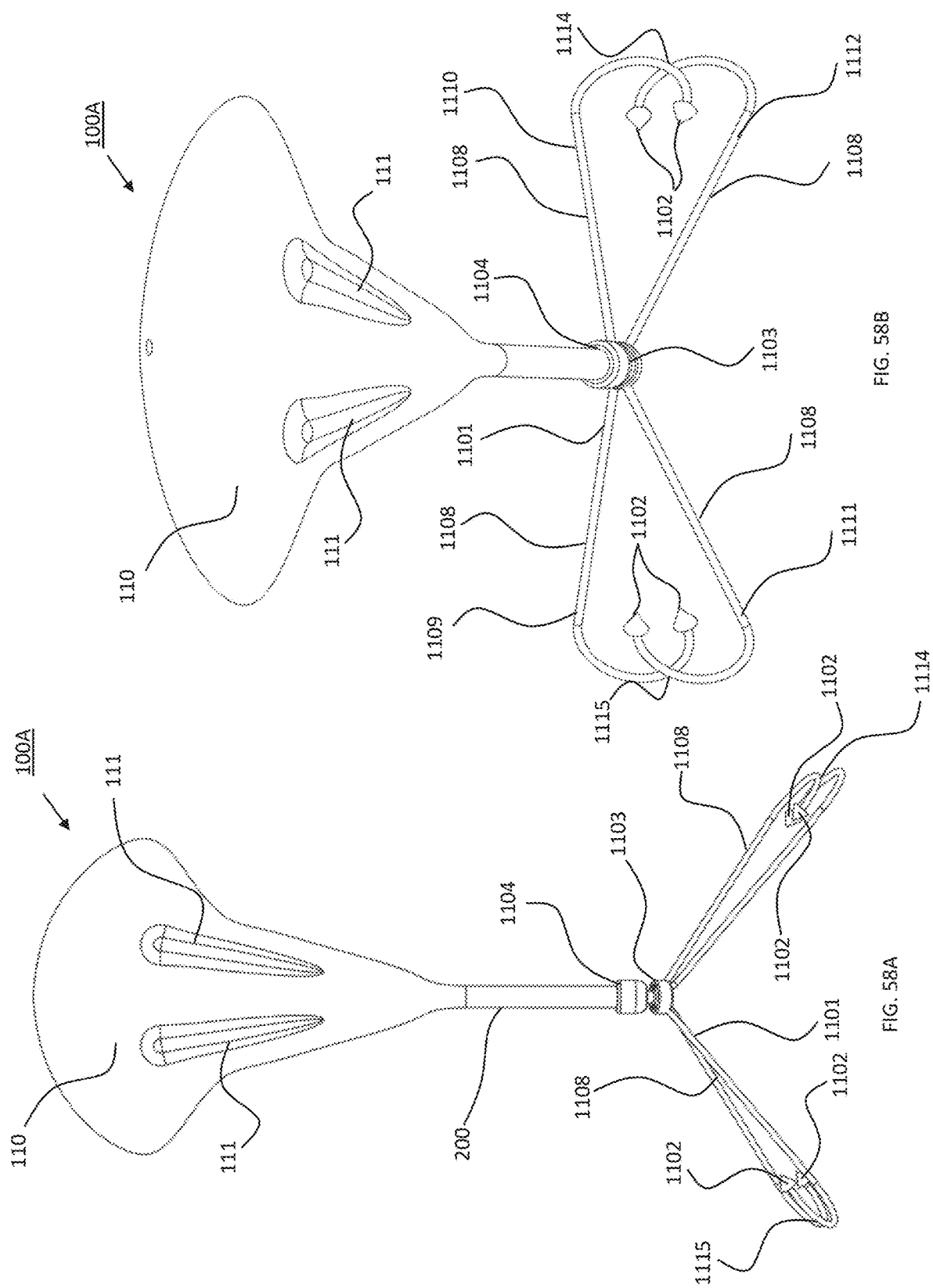
FIGS. 58A and 58B illustrate an intracardiac device coupled to a splayhook anchor plate according to an embodiment of the present disclosure.

FIGS. 58A and 58B illustrate an intracardiac device (100A) coupled to a splayhook anchor plate (1101). As shown in FIGS. 58A and 58B, the shaft (200) transitions into a universal receiver (1104)(1105), located at the proximal end of shaft (200), couples to, is fixed to, and is rotational 360 degrees on and while coupled to the male universal ball connector (1113) on the central universal ball mount (1103), located at the center of the universal splayhook anchor plate (1101). The universal shaft receiver (1104), located at the proximal end of the shaft (200)(1105), connects each of the above described embodiments (100)(600)(619)(700)(800)(900) to the central universal ball mount (1103) and, thus, to the universal splayhook anchor plate (1101). The universal splayhook anchor plate (1101) functions the same way the apical base plate assembly (300) does in that it fixes and holds in place (1104) the shaft (200)(1105) which is fixed to the distal member (110)(601)(614)(710)(810)(910) because the universal splayhook anchor plate (1101) is anchored, fixed, and secured to the medial (1106) and lateral (1107) papillary muscles (10) inside the ventricular chamber. In various embodiments, the design of the universal splayhook anchor plate (1101) and the components used in the assembly are such that it (1101) is mechanically more efficient than the apical base plate assembly (300) because it delivers all of the forces of the atrioventricular pressure gradient and the energy and force associated with it, as described above, directly into the papillary muscles, at their base thereby more mechanically, efficiently, and accurately restores and imparts lost natural and native function and purpose. The universal splayhook anchor plate (1101) is assembled from the following components; the central universal ball mount (1103), the male universal ball connector (1113) that the universal shaft receiver (1104) couples and fixates onto (1113), and the four splayhook fixation wires (1108), a right upper splay hook fixation wire (1110) & left upper splayhook fixation wire (1109) and a right lower splayhook fixation wire (1112) & left lower splayhook fixation wire (1111). On the distal end of each splayhook fixation wire (1108) is a barbed splayhook tissue anchor (1102) which anchors or fixates each individual splayhook fixation wire (1108), the barbed splayhook tissue anchor (1102) being the distal component of this wire and being fixated to the wire (1108), securely into the papillary muscles (10), both medial (1106) and lateral (1107), seated or secured into the tissue by the tension and pull between the opposing medial (1106) and lateral (1107) papillary muscles (10). The splayhook fixation wires (1108) extend in a reverse taper from the central universal ball mount (1103) with the right upper splayhook fixation wire (1110) crossing above (1114) the right lower splayhook fixation wire (1112) and the left lower splayhook fixation wire (1111) crossing above (1115) the left upper splayhook fixation wire (1109) thereby creating a right pressure opening crossing point (1114) and a left pressure opening crossing point (1115). The distal ends, at the pressure opening crossing points (1114) (1115), of the splayhook fixation wires (1108) now open under direct pressure at the right (1114) and left (1115) pressure opening crossing points (1114) (1115) and will close from memory, at the same points (1114)(1115), immediately after the papillary muscles (10) pass through the this open channel. The open channel is created at and in the right pressure opening crossing point (1114) by the right upper and lower splayhooks fixation wires (1110)(1112) being pressed directly into and against the medial papillary muscle (1106) by steering the procedural sheath distal end (1201) toward the medial papillary muscle (1106). This opens the channel by pressing the right pressure opening point (1114) directly against the medial papillary muscle (1106) causing the right upper and lower splayhook fixation wires (1110) (1112) to move in opposite directions creating an opening or a channel through which the medial papillary muscle (1106) passes until the memory causes right upper and lower splayhook fixation wires (1110) (1112) to close, as no structure is holding them open because the medial papillary muscle (1106) has passed through the channel. This procedure is now repeated, on the lateral papillary muscle (1107) with the left pressure opening crossing point (1115). The open channel is created at and in the left pressure opening crossing point (1115) by the left upper and lower splayhooks fixation wires (1109)(1111) being pressed directly into and against the lateral papillary muscle (1107) by steering the procedural sheath distal end (1201) toward the medial papillary muscle (1107). This opens the channel by pressing the left pressure opening point (1115) directly against the lateral papillary muscle (1107) causing the left upper and lower splayhook fixation wires (1109) (1111) to move in opposite directions creating an opening or a channel through which the lateral papillary muscle (1107) passes until the memory causes left upper and lower splayhook fixation wires (1109) (1111) to close, as no structure is holding them open because the lateral papillary muscle (1107) has passed through the channel.

Figure 59:
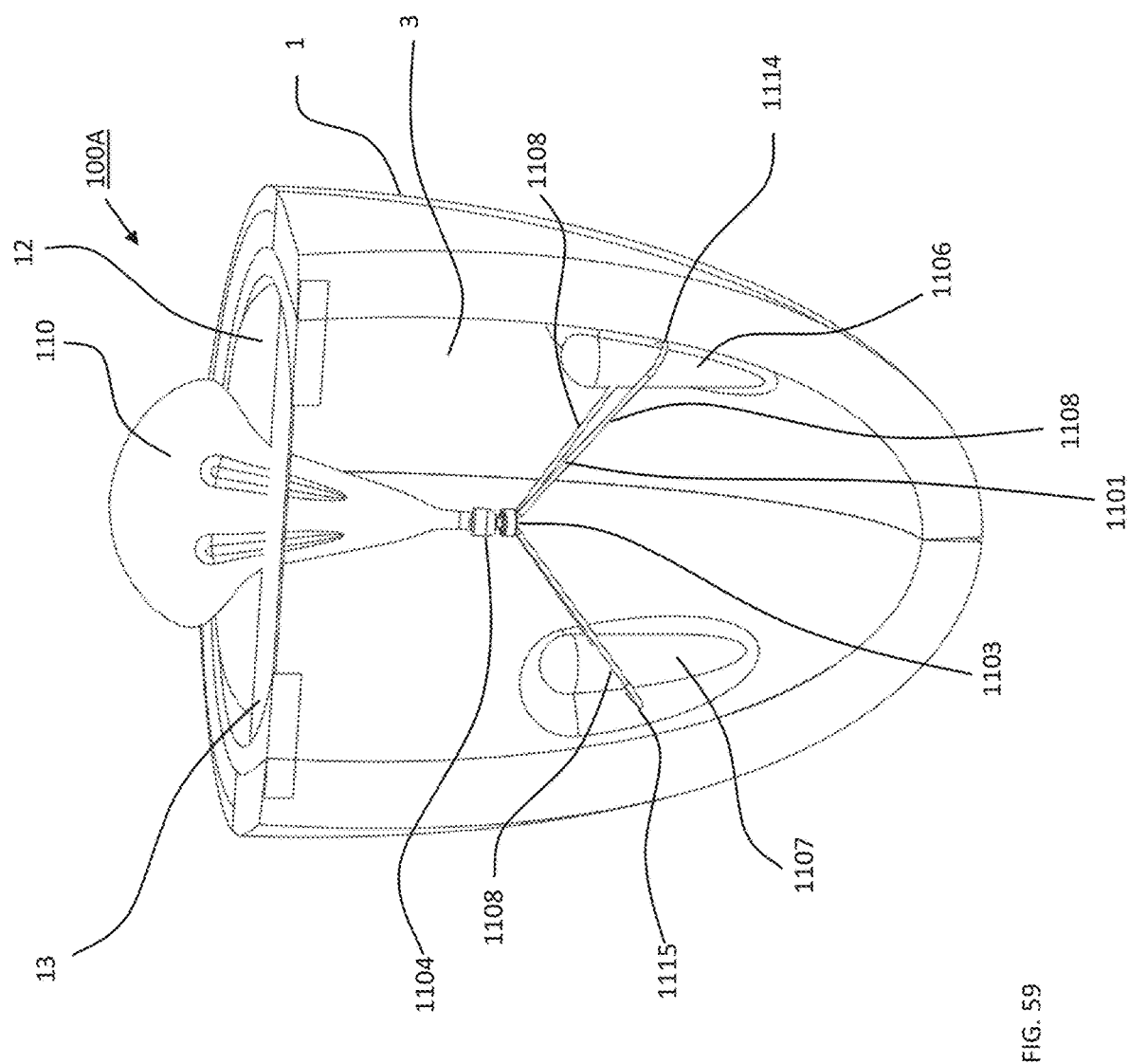
FIG. 59 illustrates an intracardiac device having a splayhook anchor plate attached to the lateral and medial papillary muscles according to an embodiment of the present disclosure.

FIG. 59 illustrates an intracardiac device (100A) placed within a heart chamber. Tension is created between the connection (1102) at either end (1107)(1106) of the universal splayhook anchor plate (1101), the lateral papillary muscle (1107) on one end and the medial papillary muscle (1106) on the other end, which cause the barbed splayhook tissue anchor points (1102) to press in (10), anchor (10), and seat (10) into the respective papillary muscles (1107)(1106). The anterior and posterior valve leaflets 'grabbing, flexing, and pulling' on the member during systole and releasing during diastole will, additionally, cause the splayhooked barbed anchor points (1102) to press in (10), anchor into (10), and seat properly (10) into the respective papillary muscles (1107)(1106). The member (110), in any shape or embodiment, intercepts atrial (2) blood and re-vectors (111) it to assist, enhance, or restore the vortex, vortical flow, and natural physiologic blood flow vector passing blood over, across, and off of the valve leaflets and into the ventricle (3) and it captures (112) the native atrioventricular pressure gradient, or the ventricular energy and force, utilizing the valvular (12)(13) and subvalvular structures (11) as they coapt or seal (12)(13)(112) and thus 'grab, flex, and pull' (112) on the member (110) in systole. The 'grabbing, flexing, and pulling' (more precisely described as atrioventricular pressure gradient forces acting on exposed area of the member (110) at the line of coaptation (112)) by the valvular (7)(12)(13) and subvalvular structures (9)(10)(11), mechanically replaces and imparts the disturbed or lost native valvular and subvalvular force (driven by the systolic atrioventricular pressure gradient) interaction with the ventricle (3), the ventricular structures (4)(5)(7), the septal wall (6), and ventricular walls (4) by transducting, meaning the capture, collection, and transfer of existing native energy & force, this native force via the universal splayhook anchor plate (1101), fixed to and in physical contact with medial (1106) and lateral (1107) papillary muscles (10), and therefor with the, the ventricle (3), ventricular structures (4)(5)(6)(7), and ventricular wall (4). This is one systemic function and/or aspect of this transcatheter device within an integrated system.

Figure 60:
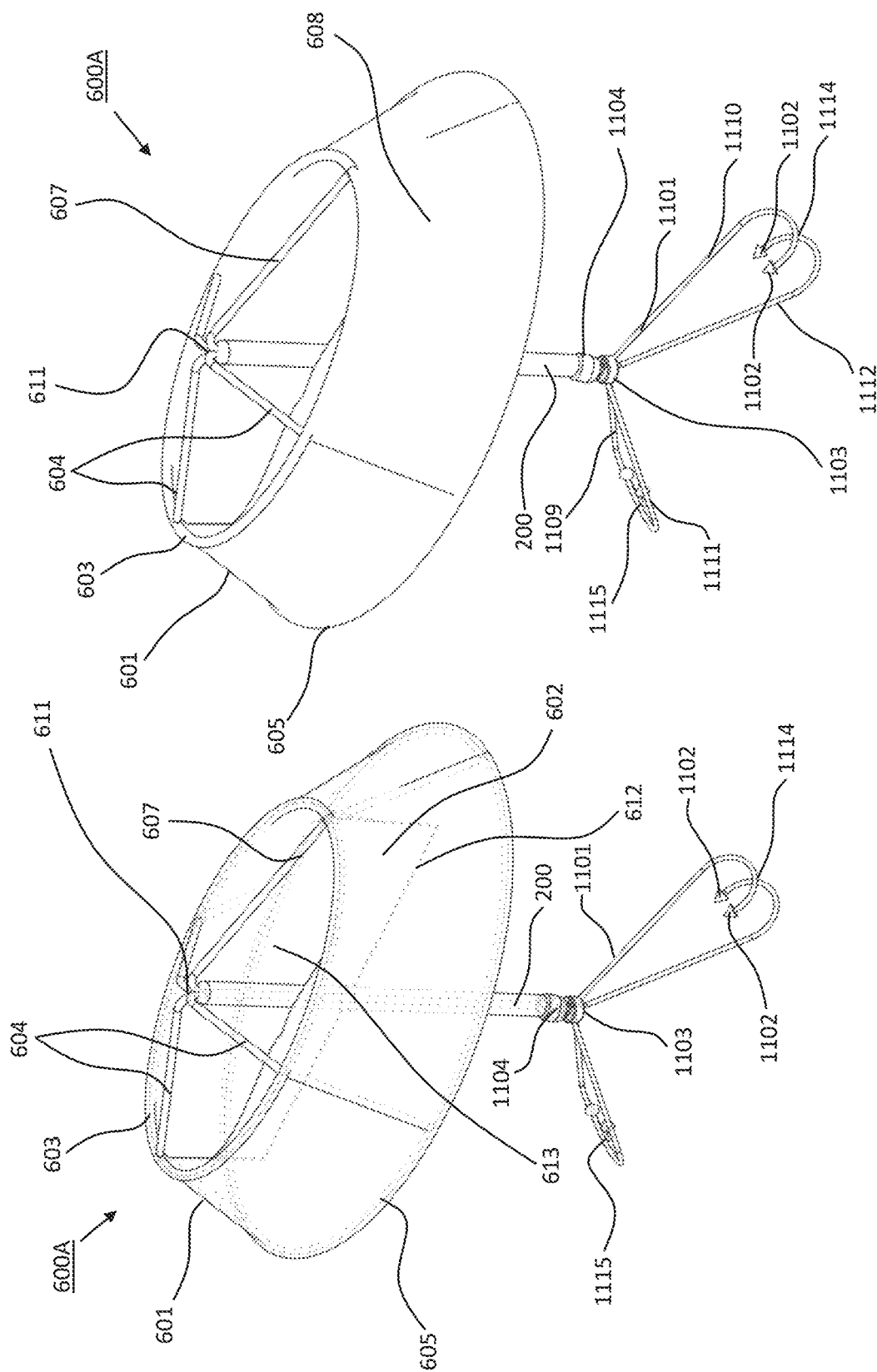
FIGS. 60A and 60B illustrate an intracardiac device coupled to a splayhook anchor plate according to an embodiment of the present disclosure.

In various embodiments, the splayhook anchor plate (1101) may be coupled to any of the intracardiac devices described herein to thereby anchor and/or position the intracardiac device within a heart chamber. The splayhook anchor plate (1101) may be suitable for minimally invasive delivery of any of the intracardiac devices described herein via a catheter as is known in the art. For example, FIGS. 60A and 60B illustrate an intracardiac device (600A) coupled to a splayhook anchor plate (1101). The splayhook anchor plates (1101) illustrated in FIGS. 60A and 60B are substantially similar to those illustrated in FIGS. 57A and 57B.

Figure 61:
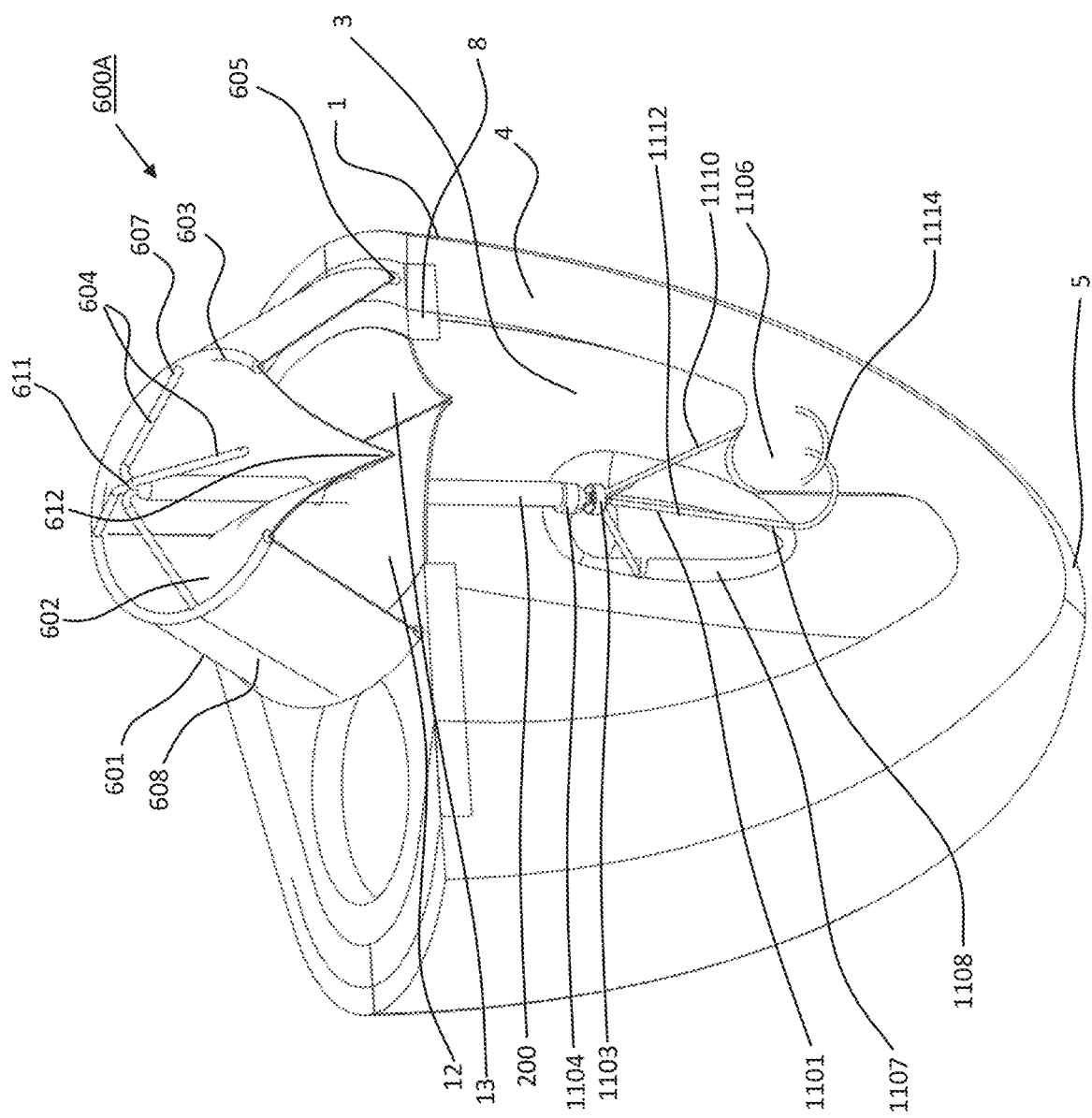
FIG. 61 illustrates an intracardiac device having a splayhook anchor plate attached to the lateral and medial papillary muscles according to an embodiment of the present disclosure.

FIG. 61 illustrates an intracardiac device (600A) having a splayhook anchor plate (1101) attached to the lateral (1107) and medial (1106) papillary muscles. The splayhook anchor plate (1101) shown in FIG. 61 is attached to the heart chamber via the papillary muscles in a substantially similar manner to that shown in FIG. 59.

Figures 62A, 62B:
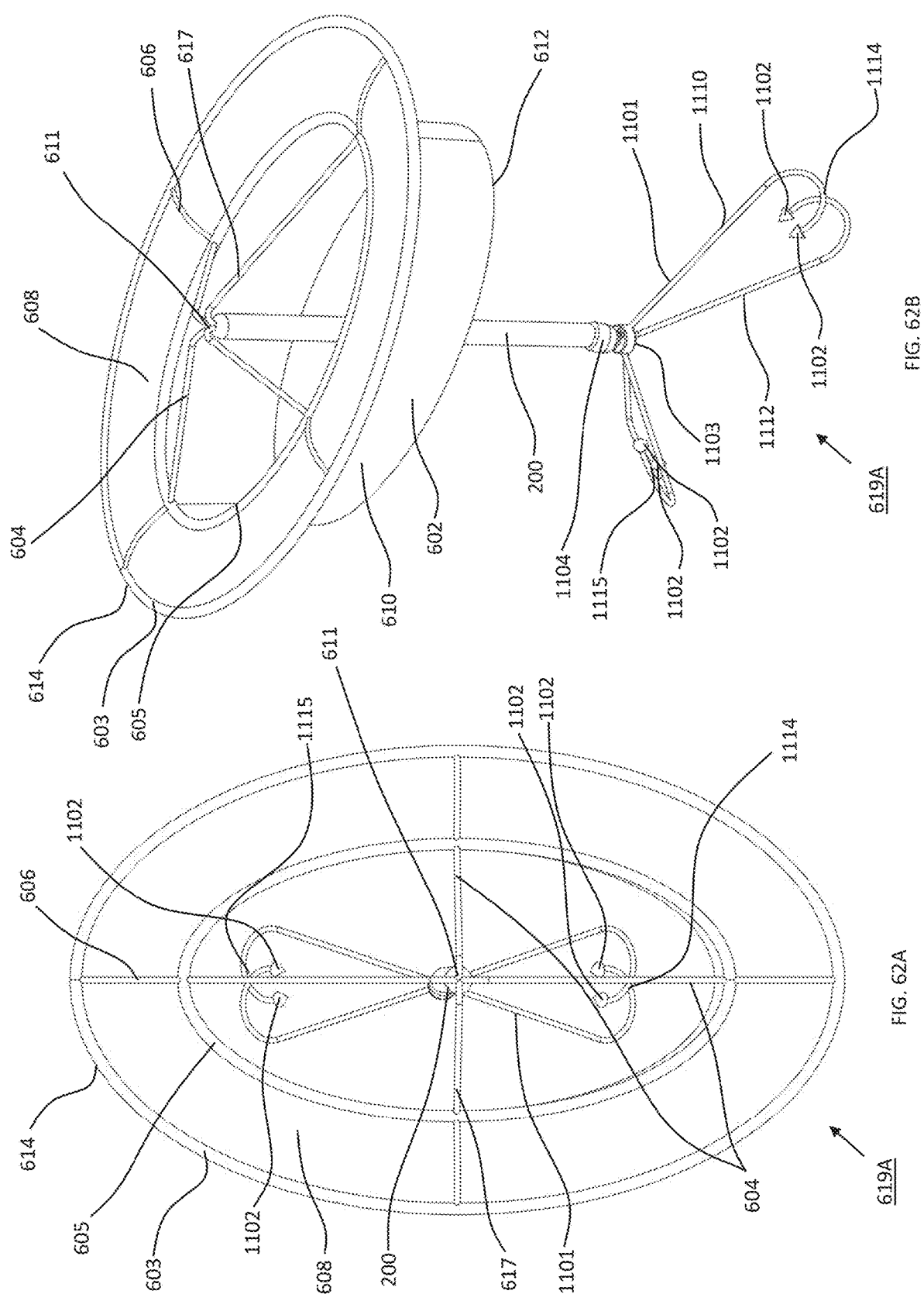
FIGS. 62A and 62B illustrate an intracardiac device coupled to a splayhook anchor plate according to an embodiment of the present disclosure.

In another example, FIGS. 62A and 62B illustrate an intracardiac device (619A) coupled to a splayhook anchor plate (1101). The splayhook anchor plates (1101) illustrated in FIGS. 62A and 62B are substantially similar to those illustrated in FIGS. 57A and 57B.

Figure 63:
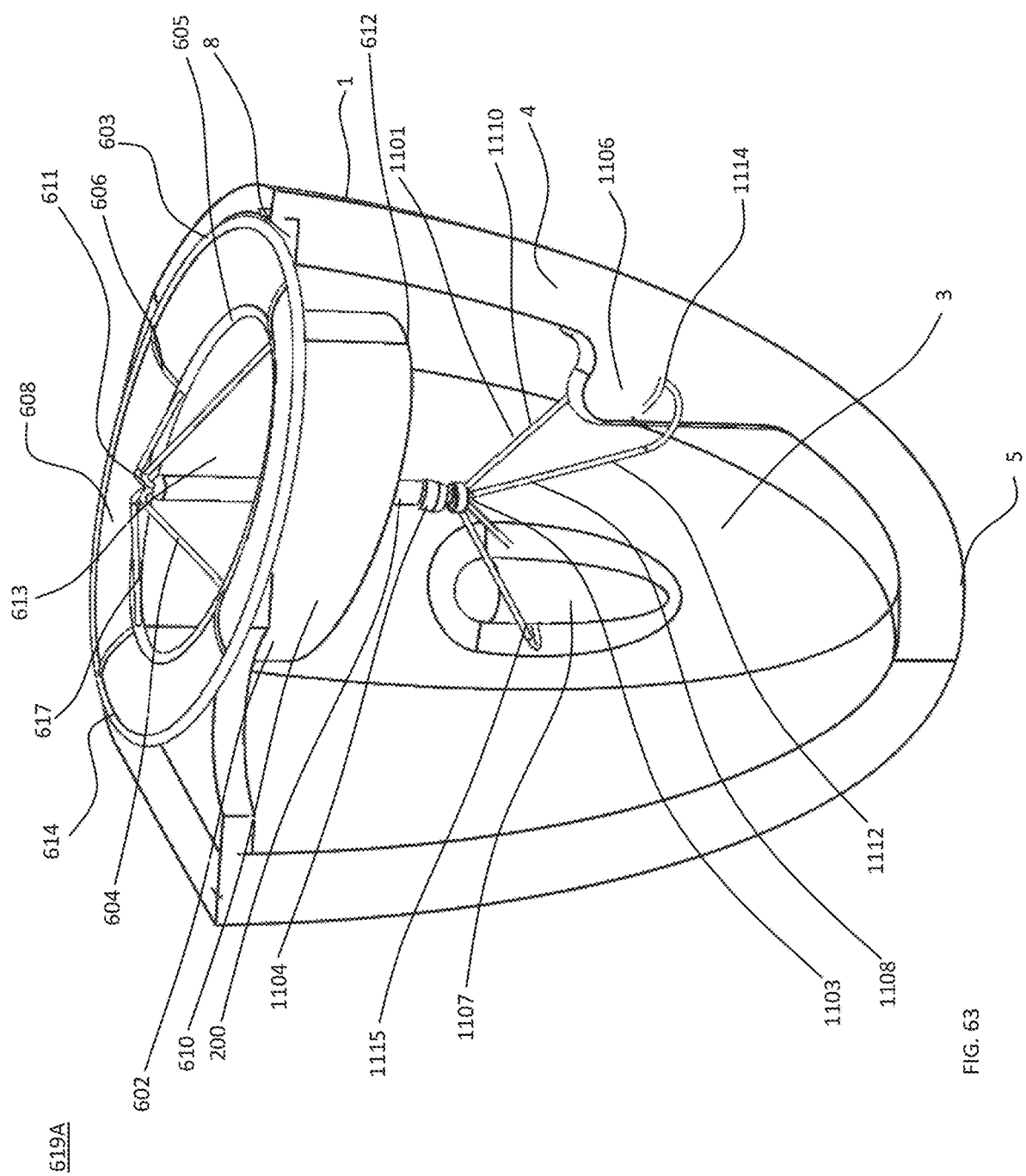
FIG. 63 illustrates an intracardiac device having a splayhook anchor plate attached to the lateral and medial papillary muscles according to an embodiment of the present disclosure.

FIG. 63 illustrates an intracardiac device (619A) having a splayhook anchor plate (1101) attached to the lateral (1107) and medial (1106) papillary muscles. The splayhook anchor plate (1101) shown in FIG. 63 is attached to the heart chamber via the papillary muscles in a substantially similar manner to that shown in FIGS. 59 and 61.

Figure 4:
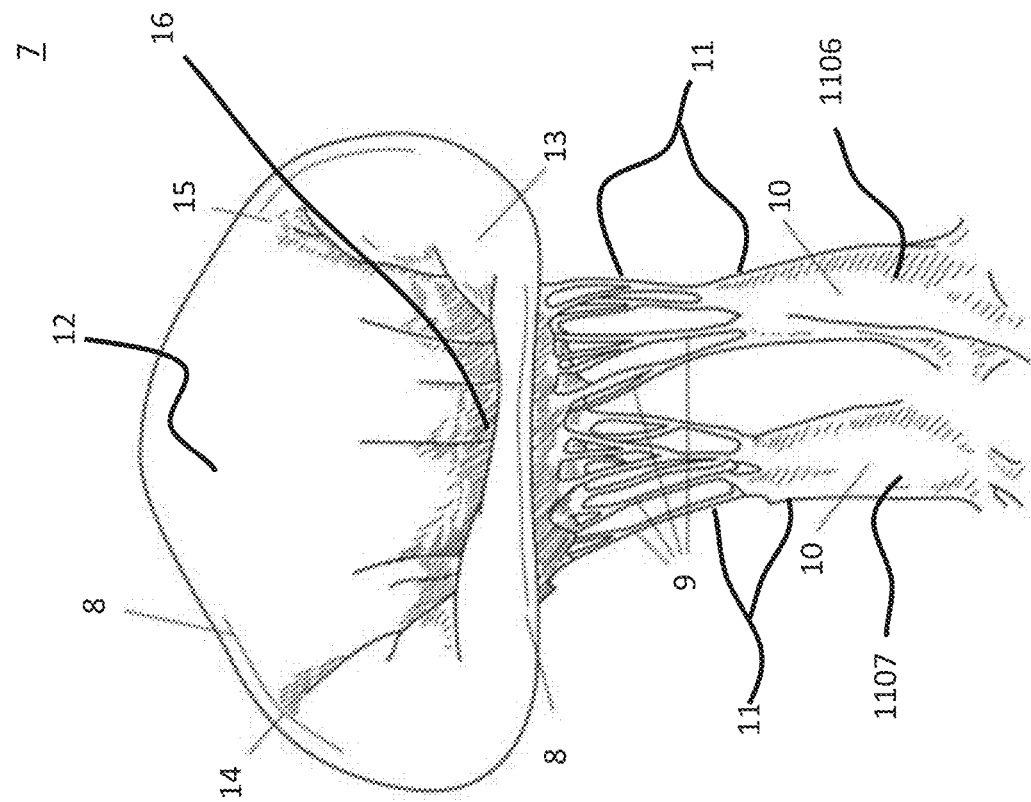
FIG. 4 illustrates the structures of the human mitral valve according to an embodiment of the present disclosure.
Figure 5:
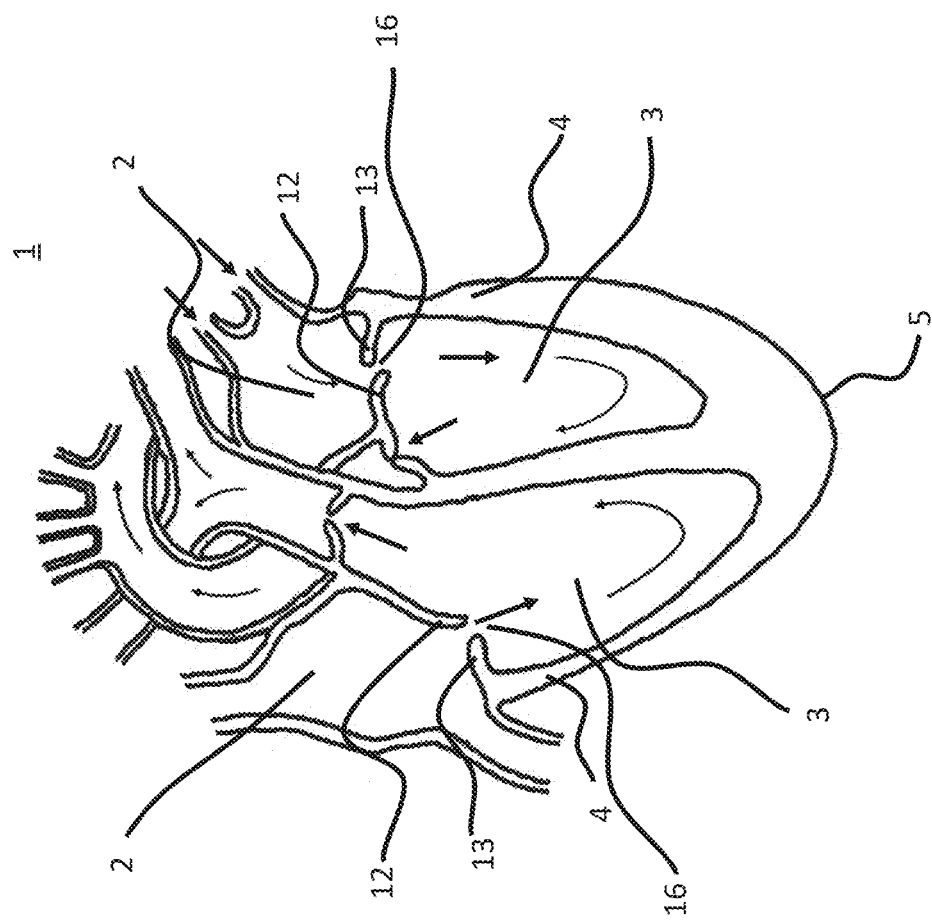
FIG. 5 illustrates the hemodynamic flow patterns of the human heart according to an embodiment of the present disclosure.

A transcatheter procedure utilizing standard transcatheter access approaches, those being defined as the transfemoral (1216), transvenous (1215), and subclavian or transjugular (1217) approaches, and standard medical transcatheter techniques, may be used to implant all of the embodiments (100)(600)(619)(700)(800)(900) of the transfemoral integrated system. The access site to the blood vessel may be through any clinically relevant location with the primary locations being a percutaneous femoral vein access (1215), a subclavian access (1217), or a jugular access (1217). An introducer sheath is then inserted into the selected vessel. Through the sheath, a guidewire, dilator, and steerable or preformed sheath is used to guide the distal end of both the guidewire and the sheath to the FIG. 3 fossa ovalis (1203). The sheath, dilator and guidewire can be maneuvered easily to the fossa ovalis (1203) under fluoroscopy or echocardiography imaging. The fossa ovalis (1203) is a naturally occurring depression in the right atrium (2) in the interatrial septal wall (1204) and is a common, well known, standard anatomical landmark to medical professionals. By FIG. 3 puncturing the thin membrane covering over the fossa ovalis (1203), the left atrium (2) can be accessed from the right atrium (2). Various techniques exist for puncturing the membrane including a needle, a Brockenbrough needle, a radio frequency catheter, and or a sharpened guidewire are commonly used. Once the septum (1204) is punctured the site can be dilated up, or enlarged, to accommodate the implant or device delivery sheath size and to place the steerable procedural sheath (1200) inside the left atrium (2). The transeptal (1203) puncture allows access to the left atrium (2) and the steerable procedural sheath (1200) is then guided, antegrade (meaning in the direction of blood flow), through the mitral (7) or atrioventricular valve (7) and into the left ventricle (3). In the left ventricle (3) the FIG. 4 medial (1106) and lateral (1107) papillary muscles (10) are visualized. The steerable procedural sheath (1200) is directed or maneuvered in between the lateral (1107) and medial (1106) papillary muscles (10) and the advance is then stopped. A universal splayhook anchor plate (1101) is fully extended from the distal end of the introducing steerable sheath (1201), that retraction and extension stopping at the central universal ball mount (1103), the point at which the universal shaft receiver (1104) is coupled (1103)(1113)(1104)(1105) to the shaft (200). The shaft (200) and member (110) or distal integrated system attachment (601)(614)(710)(810)(910) still remains housed within the steerable procedural delivery sheath (1200) and is connected and coupled (1103)(1113)(1104) to the universal splayhook anchor plate (1101). FIG. 57 The universal splayhook anchor plate (1101) is exposed and the medial papillary muscle (1106) is captured by steering the procedural steerable sheath (1200) to the medial papillary muscle (1106) and applying direct pressure on the right pressure opening crossing point (1114). The right pressure opening crossing point (1114) opens, under direct pressure, and a channel is created as the right upper and lower splayhook fixation wires (1110) (1112) move in opposite directions allowing the medial papillary muscle (1106) to pass through the channel and then the memory closes the right pressure opening crossing point (1114). The procedure is now repeated on the lateral papillary muscle (1107). The lateral papillary muscle (1107) is captured by steering the procedural steerable sheath (1200) to the lateral papillary muscle (1107) and applying direct pressure on the left pressure opening crossing point (1115). The left pressure opening crossing point (1115) opens, under direct pressure, and a channel is created as the left upper and lower splayhook fixation wires (1109) (1111) move in opposite directions allowing the lateral papillary muscle (1107) to pass through the channel and then the memory closes the left pressure opening crossing point (1115). The barbed splayhook tissue anchors (1102) on the distal ends of the splayhook fixation wires (1110)(1112)(1109)(1111), which splay and open (1115)(1114) under direct pressure, thus allowing the papillary muscles (10)(1106)(1107) to pass though the splayed or opened channel. The barbed splayhook tissue anchor points (1102) press into (10), anchor into (10), and seat properly (10) into the respective papillary muscles (10)(1107)(1106) thus securing the universal splayhook anchor plate (1101). The procedural steerable sheath (1200) is then retracted from the central universal ball mount (1103), where it had been halted to capture and anchor the papillary muscles (1106)(1107), leaving universal splayhook anchor plate (1101), from the universal ball mount (1103), and the shaft (200) with the integrated system distal attachment or member (100)(600)(619)(700)(800)(900) deployed or released from the introducing sheath (1200) as it is retracted. The integrated system distal attachment (100)(600)(619)(700)(800)(900) or member (100)(600)(619)(700)(800)(900) is deployed or released in position, either within the atrioventricular valve orifice (7)(16) or on the atrial (2) annulus (8), depending upon the embodiment being implanted. The multi-lumen tubing (400) is lead from the atrial (2) side of the implant through the fossa ovalis (1203) and to the sub-clavian (1217) or jugular (1217) access site. Near the access site a small incision is made at an appropriate site for the subcutaneous control unit (500) to be placed. A pocket is formed in the tissue and the multi-lumen tubing is tunneled to the site for the subcutaneous control unit (500). The tubing (400) is then connected to the control unit (500). The system may be fluidically connected and can have a final flush via the control unit access sites. Final adjustments can then be made to the implanted system (100)(600)(619)(700)800(900) via the axially adjustable shaft (200)(202)(206). Typically, a non-coring needle is used to puncture into the control unit (500) to adjust or dial in the level of force transduction therapy or final fill volume of the device.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In various alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An implant for altering physiological intracardiac flow, the implant comprising:
    a housing structure including a central member having a proximal end and a distal end, a plurality of struts extending radially away from the distal end of the central member, a first ring having a first diameter operably coupled to the plurality of struts, and a second ring operably coupled to the plurality of struts, the central member defining a longitudinal axis, the first ring and the second ring each defining a plane that is perpendicular to the longitudinal axis, the first ring disposed distally to the second ring;
    a skirt extending between the first ring and the second ring, the skirt extending around a circumference of the first ring and a circumference of the second ring; and
    a one-way valve disposed within the skirt, the one-way valve including a surface having a first end and a second end, the first end coupled around the circumference of the first ring, the one-way valve tapering from the first end towards the proximal end of the central member, the one-way valve having the first diameter at the first end and a second diameter at the second end, wherein the second diameter is smaller than the first diameter.

2. The implant of claim 1, wherein the one-way valve comprises a duck bill shape.

3. The implant of claim 1, wherein the one-way valve is configured such that when a force in a proximal direction is applied to the one-way valve from a distal side thereof, the one-way valve opens to permit flow of blood.

4. The implant of claim 1, wherein the one-way valve is configured such that when a force in a distal direction is applied to the one-way valve from a proximal side thereof, the one-way valve is sealed.

5. The implant of claim 1, wherein the housing structure comprises nitinol.

6. The implant of claim 1, wherein the housing structure is self-expanding.

7. The implant of claim 1, wherein the skirt comprises a polymer.

8. The implant of claim 1, wherein the skirt comprises a non-thrombotic material.

9. The implant of claim 1, wherein the one-way valve comprises a polymer selected from the group consisting of: expanded polytetrafluoroethylene (ePTFE), polyethylene terephthalate (PET), polytetrafluoroethylene impregnated PET, polyurethane (PU), silicone, and polyurethane copolymer.

10. The implant of claim 1, wherein each of the plurality of struts comprises a radial portion and a proximal portion.

11. The implant of claim 10, wherein the proximal portion is disposed at an angle to the radial portion.

12. The implant of claim 11, wherein the angle is an obtuse angle.

13. The implant of claim 1, wherein the second ring comprises a shape selected from the group consisting of: circular, oval, saddle-shaped, and D-shaped.

14. The implant of claim 1, wherein the second ring comprises one or more barbs.

15. A system for altering physiological intracardiac flow, the system comprising:
    the implant of claim 1;
    a base plate assembly configured to attach to an apex of the heart;
    a shaft comprising one or more lumens operably coupled to the central member and the base plate assembly;
    a tube having one or more lumens operably coupled to the base plate assembly; and
    a control unit coupled to the base plate assembly via the tube, the control unit having one or more sealed chambers configured to control a volume of fluid in the one or more lumens.

16. The system of claim 15, wherein the base plate assembly comprises a curved shape.

17. The system of claim 15, further comprising an inflatable bladder operably coupled along the shaft.

18. The system of claim 17, wherein the inflatable bladder is disposed adjacent to the implant.

19. The system of claim 17, wherein the inflatable bladder comprises one or more flow-directing ribs configured to alter hemodynamic flow into a ventricle.

20. The system of claim 15, wherein the shaft is axially adjustable.

* * * * *